(12) United States Patent
Nagata et al.

(10) Patent No.: US 6,800,289 B2
(45) Date of Patent: Oct. 5, 2004

(54) STRAIN OF THE WESTERN EQUINE ENCEPHALITIS VIRUS

(75) Inventors: Leslie P. Nagata, Medicine Hat (CA); Jonathon P. Wong, Medicine Hat (CA)

(73) Assignee: Her Majesty the Queen in right of Canada, as represented by the Minister of National Defence, Ottawa (CA)

( * ) Notice: Subject to any disclaimer, the term of this patent is extended or adjusted under 35 U.S.C. 154(b) by 220 days.

(21) Appl. No.: 10/023,649

(22) Filed: Dec. 21, 2001

(65) Prior Publication Data

US 2003/0143201 A1 Jul. 31, 2003

Related U.S. Application Data

(60) Provisional application No. 60/256,948, filed on Dec. 21, 2000.

(51) Int. Cl.[7] .................................................. A61K 39/21
(52) U.S. Cl. ..................................... 424/207.1; 435/91.1
(58) Field of Search ........................ 424/207.1; 435/91.1

(56) References Cited

PUBLICATIONS

Hahn et al., "Western equine encephalitis virus is a recombinant virus," Proc. Natl. Acad. Sci. USA vol. 85, pp. 5997–6001 (Aug. 1988).

Weaver et al., "A comparison of the Nuecleotide Sequences of Eastern and Western Equine Encephaloyeltiis Viruses with those of other Alphaviruses and Related RNA Viruses," 197 Virology 375–390 (1993).

Weaver et al., "Recombinational History of Molecular Evolution of Western Equine Encephalomyelitis Complex Alphaviruese," Journal of Virolgy, vol. 71, No. 1.pp. 613–623_(1997).

*Primary Examiner*—Ali R. Salimi
(74) *Attorney, Agent, or Firm*—Rader, Fishman & Grauer PLLC

(57) ABSTRACT

This invention relates to the development of a mammalian expression vector, under which expression of the structural genes of western equine encephalitis virus have been placed under the control of an eucaryotic promoter. When the recombinant vector is administered to mammalian cell culture or using a cell-free transcription/translation system, in vitro, authentic structural proteins of western equine encephalitis virus are produced as verified by reactivity with monoclonal antibodies developed to western equine encephalitis virus. When the recombinant DNA molecule is administered in vivo, a protective immune response is induced, thereby enhancing protection of the individual against subsequent infection by western equine encephalitis virus. In a similar manner, DNA vaccines to related alphaviruses (Venezuelan and eastern equine encephalitis viruses) could also be developed.

1 Claim, 11 Drawing Sheets

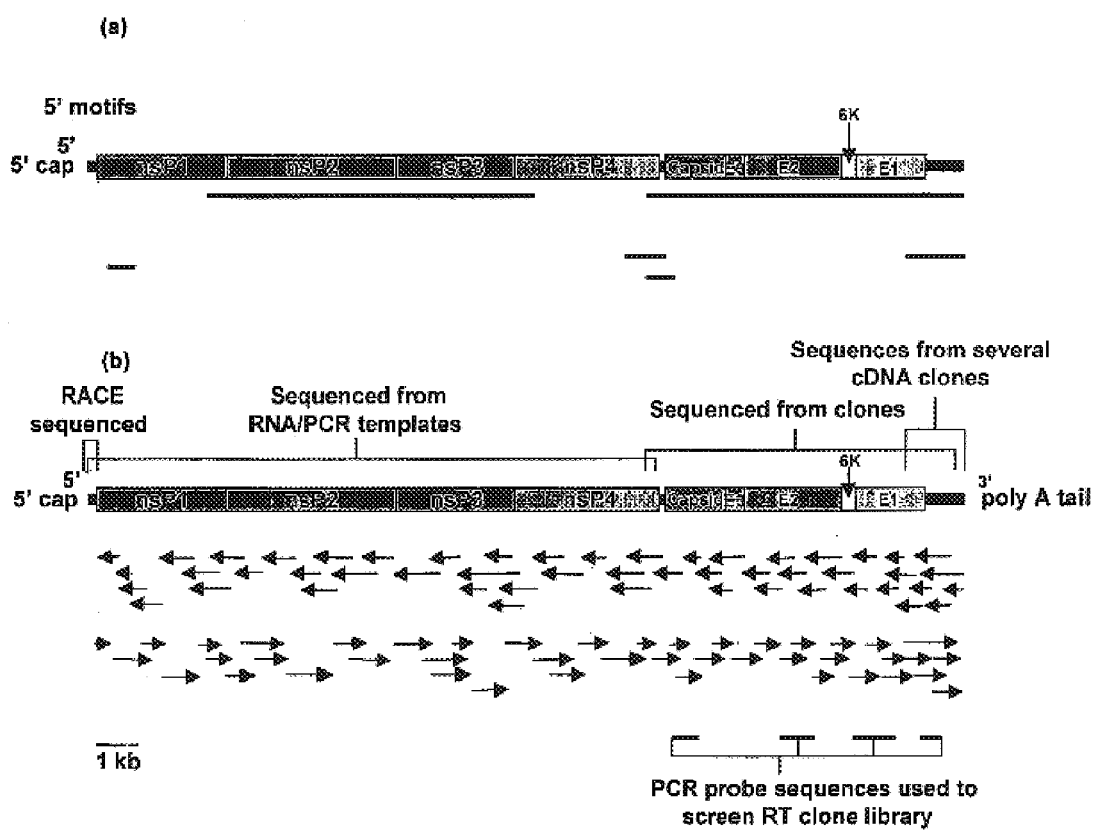

Figure 2 Multiple sequence alignment (a)
```
1   ATAGGGCATGGTATAGAGGCACCT ACCCTACAAAC A AATC   CBA87
1   ------------------------ACCCTA CAAAC T AATC   71V-1658
1   ATAGGGTATGGTGTAGAGGCAACC ACCCTA TTTC C --A C C   EEE
1   ATGGGCGGCGCAAGAGAGAAGCCC AAA C C A ATT----A C C   VEE 41  GATCCAATATGGAAAGAATTCACGTTGACTTAGA C GCTGA   CBA87
17  GATCCAATATGGAAAGAATTCACGTTGACTTAGA C GCTGA   71V-1658
39  T A T CCAA A ATGGA G A A AGTTCA T GTTGAC T TAGA C G C A GA   EEE
37  T A C CCAA A ATGGA G A A AGTTCACGTTGAC A T C G A G G A A G A   VEE 81  CAGCCC A TATGTCAAGT                            CBA87
57  CAGCCC G TATGTCAAGTC GTTACAGCGGA CGTTTCCACA A   71V-1658
79  CAGCCC A T TC G TCAAGT C A C T G CA A A G A TGC T T T CCACA T   EEE
77  CAGCCC A T TCC T CA G AG C T T TACA C GGAGC T T C C G C A G   VEE 97  TTTGAGAT C GAAGCAA G GCAGGTCACTGACAATGACCATG   71V-1658
119 TTTGAGA T A GAAGCAA C GCAGGTCACTGAC AATGACCATG   EEE
117 TTTGAG G T A G AAGC C A AGCAGGTCACTGA T AATGACCATG   VEE 137 C C AATGCCAGAGCGTTTTCGCATGTGGC AACAAAGCTCAT   71V-1658
159 C T AATGC T AG G GCGTTTTCGCA C C T AG C T A C T AAGCTC A T   EEE
157 C T AATGCCAGAGCGTTTTCGCAT C TGG C TT C AAA A C T G A T   VEE 177 TGAGA G CGAAGTCGACCGGGACCAAGTTATCTTGGACAT   71V-1658
199 TGA G G G A GAAGTGGA T ACA G ACCA G GT G ATC C T GGA T A T T   EEE
197 C G A A A C G A G G T G G ACC C ATC C G A CACG A T C C T T GACAT T   VEE
```

(b)
```
CTCGATAT G GGCTTCCG C CGTAGG C TCAAG      71V-1658
C C T GATATA GG G C T T C C G CGT A GG T C C A G G      WEE-5614
CTCGATAT A GG A TT G C G T C G CC G AA T T A AG      EEE
``` a. The 5' terminus of WEE CBA87 (1-97), WEE 71V-1658 (25-240), EEE (1-238) and VEE (1-236) via Clustal module of DNAStar. Areas where sequences differ are boxed.

b. Hypervariable region identified in nsP1. Alignment of WEE 71V-1658 (1420-1449), WEE 1654 (65-94) and EEE (1415-1444) is shown.

Figure 3 Stem loop structures in the 5' NTR

Hairpin structures were identified using the RNA folding program of the Genequest module (DNASTAR).

a. Structures for WEE (CBA87/71V-1658) sequence (1-192).
b. Structures for EEE (1-192).
Minimal free energy values are shown for the different structures.

(a) Double stem loop structures in SIN.

(b) Double stem loop structures in 3' NTR of WEE. Residues in the SIN-like 40 nt repeat are shaded.

(c) Stem loop structures in EEE.

Figure 4  Stem loop structures in the 3' NTR

Figure 5    Phylogenetic relationship of the WEE nonstructural region
            compared to other alphaviruses a) nsP1
- EEE
- 71V-1658
- VEE
- SIN
- ONN
- SF
- RR b) nsP4
- EEE
- 71V-1658
- VEE
- SIN
- RR
- SF
- ONN c) nsP1-4
- EEE
- 71V-1658
- VEE
- SIN
- ONN
- SF
- RR

Figure 6    Expression of WEE structural genes in cell culture

One µg of plasmid DNA was transfected into Vero cells. After 31 hrs incubation, the cells were histochemically stained using a monoclonal antibody to WEE (11D2).
a. pCXH-3; b. pCI (control plasmid).

Figure 7 In vitro transcription and translation of WEE expression vectors

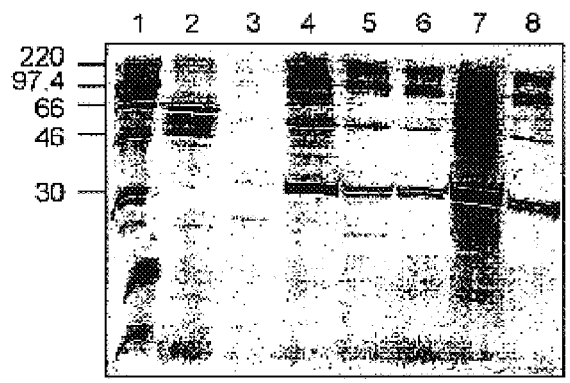

Qiagen purified vectors containing the WEE 26S insert were expressed *in vitro* using the TNT system and [$^{35}$S]-methionine labelling. Three μL aliquots of each samples were run by SDS-PAGE on a 12% gel.
Lane: 1) Rainbow $^{14}$C-labelled marker; 2) Luciferase translation control; 3) pVAX; 4) pVHX-6; 5)pCXH-3; 6) pcDWXH-7; 7) pcDWHX-45; 8) pXTR2-4.

Figure 8  WEE mouse infectivity model

Groups of 4 mice were inoculated intranasally with 50 µL of virus (approximately $10^4$ PFU). The mice were monitored for 12 days, and the % survival graphed.

Figure 9  Protection using ballistic delivery of pCXH-3

■ pCI
● pCHX3
△ pCHX3 x 2

% Survival vs Days Post Infection

Groups of 4 mice were immunized with one or two doses (2 x 1.25 µg) of either pCI or pCXH-3. The interval between boosters (2 doses) or challenge was 3 weeks. The mice were challenged intranasally with 50 µL of WEE Fleming (1.25 x $10^4$ PFU). The mice were monitored for 12 days, and the % survival graphed.

Figure 10    Protection using ballistic delivery of pVHX-6

- ● pVHX-6
- ■ pVAX

% Survival vs Days Post Infection

Groups of 4 mice were immunized with four doses (2 x 1.25 µg) of pVAX or pVXH-6. The interval between boosters or challenge was 2 weeks. The mice were challenged intranasally with 50 µL of WEE Fleming (1.25 x $10^4$ PFU). The mice were monitored for 14 days, and the % survival graphed.

Figure 11  Protection using ballistic delivery of pVHX-6

| Symbol | Legend |
|---|---|
| ◆ | Control |
| ■ | WEE inactivated |
| △ | pVAX 3x |
| □ | pVHX-6 3x |
| ▽ | pVAX 4x |
| ● | pVHX-6 4x |

Groups of 5-8 mice were immunized with three or four doses (2 x 1.25 µg) of pVAX or pVXH-6. The interval between boosters or challenge was 2 weeks.
The mice were challenged intranasally with 50 µL of WEE Fleming (1.7 x 10$^4$ PFU).
Untreated control and WEE inactivated control (3 doses) groups were also included.
The mice were monitored for 14 days, and the % survival graphed.

SEQUENCE LISTING

<160> NUMBER OF SEQ ID NOS: 49

<210> SEQ ID NO 1
<211> LENGTH: 11484
<212> TYPE: DNA
<213> ORGANISM: Western equine encephalomyelitis virus - strain 71V-1658
<220> FEATURE:
<221> NAME/KEY: CDS
<222> LOCATION: (25)..(7428)
<223> OTHER INFORMATION: 5' UTR <1 .. 24
<220> FEATURE:
<221> NAME/KEY: CDS
<222> LOCATION: (7473)..(11183)
<223> OTHER INFORMATION: encodes nucleocapsid, E3, E2, 6K and E1 proteins

<400> SEQUENCE: 1

```
acccctacaaa ctaatcgatc caat atg gaa aga att cac gtt gac tta gat         51
                              Met Glu Arg Ile His Val Asp Leu Asp
                               1               5 gct gac agc ccg tat gtc aag tcg tta cag cgg acg ttt cca caa ttt         99
Ala Asp Ser Pro Tyr Val Lys Ser Leu Gln Arg Thr Phe Pro Gln Phe
 10              15                  20                  25 gag atc gaa gca agg cag gtc act gac aat gac cat gcc aat gcc aga        147
Glu Ile Glu Ala Arg Gln Val Thr Asp Asn Asp His Ala Asn Ala Arg
                 30                  35                  40 gcg ttt tcg cat gtg gca aca aag ctc att gag agc gaa gtc gac cgg        195
Ala Phe Ser His Val Ala Thr Lys Leu Ile Glu Ser Glu Val Asp Arg
             45                  50                  55 gac caa gtt atc ttg gac att gga agt gcg ccc gtc aga cat gca cat        243
Asp Gln Val Ile Leu Asp Ile Gly Ser Ala Pro Val Arg His Ala His
         60                  65                  70 tcc aat cac cgc tat cat tgt atc tgc cct atg ata agc gct gaa gac        291
Ser Asn His Arg Tyr His Cys Ile Cys Pro Met Ile Ser Ala Glu Asp
     75                  80                  85 ccg gac aga cta caa cgg tat gca gaa aga ctt aag aaa agt gac att        339
Pro Asp Arg Leu Gln Arg Tyr Ala Glu Arg Leu Lys Lys Ser Asp Ile
 90                  95                 100                 105 acc gac aag aac ata gcc tct aag gcg gca gac ctg ctg gaa gtc atg        387
Thr Asp Lys Asn Ile Ala Ser Lys Ala Ala Asp Leu Leu Glu Val Met
                110                 115                 120 tca aca cca gac gca gag act cca tct ctg tgt atg cac aca gac gcc        435
Ser Thr Pro Asp Ala Glu Thr Pro Ser Leu Cys Met His Thr Asp Ala
                125                 130                 135 acg tgt agg tac ttt gga agt gta gca gta tac caa gat gtg tac gca        483
Thr Cys Arg Tyr Phe Gly Ser Val Ala Val Tyr Gln Asp Val Tyr Ala
                140                 145                 150
```

-continued

| | | |
|---|---|---|
| gtc cat gca ccg aca tca atc tac cac cag gcg ctt aaa gga gtt agg<br>Val His Ala Pro Thr Ser Ile Tyr His Gln Ala Leu Lys Gly Val Arg<br>    155                            160                          165 | 531 |

```
gtc cat gca ccg aca tca atc tac cac cag gcg ctt aaa gga gtt agg      531
Val His Ala Pro Thr Ser Ile Tyr His Gln Ala Leu Lys Gly Val Arg
    155                 160                 165 aca att tac tgg ata ggc ttt gac acg acc cct ttt atg tac aaa aac      579
Thr Ile Tyr Trp Ile Gly Phe Asp Thr Thr Pro Phe Met Tyr Lys Asn
170                 175                 180                 185 atg gca ggt tcc tac cct act tac aac acg aac tgg gct gac gag aga      627
Met Ala Gly Ser Tyr Pro Thr Tyr Asn Thr Asn Trp Ala Asp Glu Arg
                190                 195                 200 gta ttg gaa gca cgt aac att ggc ctc ggt aac tca gat ctt cag gag      675
Val Leu Glu Ala Arg Asn Ile Gly Leu Gly Asn Ser Asp Leu Gln Glu
            205                 210                 215 agc agg ctt gga aaa ctc tca atc ctt agg aag aag agg ctc caa cct      723
Ser Arg Leu Gly Lys Leu Ser Ile Leu Arg Lys Lys Arg Leu Gln Pro
        220                 225                 230 act aat aag atc ata ttc tcg gtt ggt tca aca atc tac aca gaa gat      771
Thr Asn Lys Ile Ile Phe Ser Val Gly Ser Thr Ile Tyr Thr Glu Asp
    235                 240                 245 aga tca ctg tta cgt agc tgg cat ctt cca aac gtg ttc cac ttg aaa      819
Arg Ser Leu Leu Arg Ser Trp His Leu Pro Asn Val Phe His Leu Lys
250                 255                 260                 265 gga aag tct aac ttc aca ggt aga tgt ggg acc att gtc agc tgt gaa      867
Gly Lys Ser Asn Phe Thr Gly Arg Cys Gly Thr Ile Val Ser Cys Glu
                270                 275                 280 ggg tac gtc atc aaa aag ata acg atc agc cca gga cta tac ggt aaa      915
Gly Tyr Val Ile Lys Lys Ile Thr Ile Ser Pro Gly Leu Tyr Gly Lys
            285                 290                 295 gtt gag aac ttg gcg tcc aca atg cat cgc gag ggt ttc ttg agt tgc      963
Val Glu Asn Leu Ala Ser Thr Met His Arg Glu Gly Phe Leu Ser Cys
        300                 305                 310 aaa gtc aca gat acg ctg cgc ggc gag agg gtt tct ttt gct gtg tgt     1011
Lys Val Thr Asp Thr Leu Arg Gly Glu Arg Val Ser Phe Ala Val Cys
    315                 320                 325 acg tat gta cca gcc aca ctt tgc gat cag atg aca ggg att ctg gca     1059
Thr Tyr Val Pro Ala Thr Leu Cys Asp Gln Met Thr Gly Ile Leu Ala
330                 335                 340                 345 act gac gtt agt gtg gat gac gca caa aaa cta ttg gtt ggg ctc aac     1107
Thr Asp Val Ser Val Asp Asp Ala Gln Lys Leu Leu Val Gly Leu Asn
                350                 355                 360 caa agg att gtc gtc aat ggt agg acg caa aga aat act aac aca atg     1155
Gln Arg Ile Val Val Asn Gly Arg Thr Gln Arg Asn Thr Asn Thr Met
            365                 370                 375 cag aac tat cta tta cca gtc gtc gcc cag gcg ttt tcc agg tgg gcg     1203
Gln Asn Tyr Leu Leu Pro Val Val Ala Gln Ala Phe Ser Arg Trp Ala
        380                 385                 390 cgt gaa cat cgt gcc gac ttg gac gac gag aaa gaa cta ggg gtg cgg     1251
Arg Glu His Arg Ala Asp Leu Asp Asp Glu Lys Glu Leu Gly Val Arg
    395                 400                 405 gag cgc act ctt act atg ggc tgc tgc tgg gct ttc aag acc cag aaa     1299
Glu Arg Thr Leu Thr Met Gly Cys Cys Trp Ala Phe Lys Thr Gln Lys
410                 415                 420                 425 atc aca tcc atc tac aag aag cct ggt acg caa aca att aag aaa gta     1347
Ile Thr Ser Ile Tyr Lys Lys Pro Gly Thr Gln Thr Ile Lys Lys Val
                430                 435                 440 cct gcc gtc ttt gac tca ttt gtg att cca cgc ctt acc agc cac ggg     1395
Pro Ala Val Phe Asp Ser Phe Val Ile Pro Arg Leu Thr Ser His Gly
            445                 450                 455 ctc gat atg ggc ttc cgc cgt agg ctc aag ctg ctg ctt gaa cca act     1443
Leu Asp Met Gly Phe Arg Arg Arg Leu Lys Leu Leu Leu Glu Pro Thr
        460                 465                 470
```

```
gtc aaa ccc gca ccg gct att aca atg gcc gat gtg gag cat ctg cgt    1491
Val Lys Pro Ala Pro Ala Ile Thr Met Ala Asp Val Glu His Leu Arg
475                 480                 485 ggc tta cag caa gaa gct gaa gaa gtg gct gca gcg gaa gag atc aga    1539
Gly Leu Gln Gln Glu Ala Glu Glu Val Ala Ala Ala Glu Glu Ile Arg
490                 495                 500                 505 gaa gcc ctg cca ccc ttg ctc cct gaa ata gaa aaa gag acc gta gag    1587
Glu Ala Leu Pro Pro Leu Leu Pro Glu Ile Glu Lys Glu Thr Val Glu
                510                 515                 520 gca gaa gta gac ctc att atg caa gag gca gga gca ggt agc gtg gag    1635
Ala Glu Val Asp Leu Ile Met Gln Glu Ala Gly Ala Gly Ser Val Glu
            525                 530                 535 aca cca cga gga cac atc agg gtg aca agt tac cca ggc gaa gag aag    1683
Thr Pro Arg Gly His Ile Arg Val Thr Ser Tyr Pro Gly Glu Glu Lys
        540                 545                 550 att ggg tct tac gct ata ctt tca ccc cag gcg gta ttg aat agt gaa    1731
Ile Gly Ser Tyr Ala Ile Leu Ser Pro Gln Ala Val Leu Asn Ser Glu
    555                 560                 565 aaa ctg gcg tgt atc cac cca ttg gcg gaa caa gta ctg gta atg act    1779
Lys Leu Ala Cys Ile His Pro Leu Ala Glu Gln Val Leu Val Met Thr
570                 575                 580                 585 cac aaa ggt agg gca ggg aga tac aaa gtc gag cca tac cac ggt aag    1827
His Lys Gly Arg Ala Gly Arg Tyr Lys Val Glu Pro Tyr His Gly Lys
                590                 595                 600 gtc att gta cca gaa ggg acg gcg gtc cct gtt caa gac ttc cag gca    1875
Val Ile Val Pro Glu Gly Thr Ala Val Pro Val Gln Asp Phe Gln Ala
                605                 610                 615 ttg agt gag agc gct acg atc gtt ttc aac gag agg gag ttc gta aac    1923
Leu Ser Glu Ser Ala Thr Ile Val Phe Asn Glu Arg Glu Phe Val Asn
            620                 625                 630 aga tac ctg cac cac atc gca atc aac gga gga gcg cta aac act gac    1971
Arg Tyr Leu His His Ile Ala Ile Asn Gly Gly Ala Leu Asn Thr Asp
635                 640                 645 gaa gag tac tat aag act gta aag act cag gac aca gac tca gaa tac    2019
Glu Glu Tyr Tyr Lys Thr Val Lys Thr Gln Asp Thr Asp Ser Glu Tyr
650                 655                 660                 665 gtc ttc gat att gac gca cga aag tgt gtt aag cga gaa gac gca ggt    2067
Val Phe Asp Ile Asp Ala Arg Lys Cys Val Lys Arg Glu Asp Ala Gly
                670                 675                 680 ccc ttg tgc cta acc ggt gat ctg gta gat cca cca ttt cac gag ttt    2115
Pro Leu Cys Leu Thr Gly Asp Leu Val Asp Pro Pro Phe His Glu Phe
            685                 690                 695 gcg tac gag agt ctc aag aca cga cca gca gca cct cac aaa gtc cca    2163
Ala Tyr Glu Ser Leu Lys Thr Arg Pro Ala Ala Pro His Lys Val Pro
        700                 705                 710 acc atc gga gtc tat gga gtg cca ggt tca ggt aaa tct gga atc atc    2211
Thr Ile Gly Val Tyr Gly Val Pro Gly Ser Gly Lys Ser Gly Ile Ile
    715                 720                 725 aaa agc gct gtg act aag aaa gat ctg gtt gtg agt gcg aag aag gaa    2259
Lys Ser Ala Val Thr Lys Lys Asp Leu Val Val Ser Ala Lys Lys Glu
730                 735                 740                 745 aac tgc gca gaa atc atc agg gat gta agg agg atg aga cgt atg gat    2307
Asn Cys Ala Glu Ile Ile Arg Asp Val Arg Arg Met Arg Arg Met Asp
                750                 755                 760 gtt gct gct agg act gtc gat tca gtg ctt cta aat ggg gtt aag cac    2355
Val Ala Ala Arg Thr Val Asp Ser Val Leu Leu Asn Gly Val Lys His
            765                 770                 775 ccc gtt aac act ctg tac att gat gag gca ttt gcc tgc cat gca ggg    2403
Pro Val Asn Thr Leu Tyr Ile Asp Glu Ala Phe Ala Cys His Ala Gly
```

|   |   |
|---|---|
| acg ctg ctg gca ctg att gcc atc gtc aaa cct aag aaa gtg gta ttg<br>Thr Leu Leu Ala Leu Ile Ala Ile Val Lys Pro Lys Lys Val Val Leu<br>795                  800                 805 | 2451 |
| tgc ggg gac cca aaa caa tgc ggc ttc ttt aac atg atg tgc ctg aaa<br>Cys Gly Asp Pro Lys Gln Cys Gly Phe Phe Asn Met Met Cys Leu Lys<br>810                 815                820              825 | 2499 |
| gta cat ttt aac cat gac ata tgc act gaa gtg tac cat aaa agc atc<br>Val His Phe Asn His Asp Ile Cys Thr Glu Val Tyr His Lys Ser Ile<br>                830                835              840 | 2547 |
| tct agg agg tgc aca cag act gta acc gcc atc gtc tcc acg ctc ttc<br>Ser Arg Arg Cys Thr Gln Thr Val Thr Ala Ile Val Ser Thr Leu Phe<br>         845                850              855 | 2595 |
| tac gac aag cga atg aag acg gtt aac cca tgt gct gat aaa atc atc<br>Tyr Asp Lys Arg Met Lys Thr Val Asn Pro Cys Ala Asp Lys Ile Ile<br>         860                865              870 | 2643 |
| ata gat acc aca ggg acc aca aag ccg cac aaa gat gat ctg att cta<br>Ile Asp Thr Thr Gly Thr Thr Lys Pro His Lys Asp Asp Leu Ile Leu<br>875                  880                885 | 2691 |
| acc tgt ttc aga gga tgg gtg aaa cag cta cag att gac tac aaa aat<br>Thr Cys Phe Arg Gly Trp Val Lys Gln Leu Gln Ile Asp Tyr Lys Asn<br>890                  895               900              905 | 2739 |
| cac gaa atc atg act gcg gct gca tcg caa gga ctt acg cgg aaa ggc<br>His Glu Ile Met Thr Ala Ala Ala Ser Gln Gly Leu Thr Arg Lys Gly<br>                910                915              920 | 2787 |
| gtt tat gct gtc agg tac aaa gtc aac gag aat cca ctc tac tcg cag<br>Val Tyr Ala Val Arg Tyr Lys Val Asn Glu Asn Pro Leu Tyr Ser Gln<br>         925                930              935 | 2835 |
| act tct gag cac gtg aac gtg tta ctt aca cgc aca gaa aaa cgc att<br>Thr Ser Glu His Val Asn Val Leu Leu Thr Arg Thr Glu Lys Arg Ile<br>         940                945              950 | 2883 |
| gtc tgg aag acg cta gct ggt gat ccc tgg ata aag aca ctt aca gct<br>Val Trp Lys Thr Leu Ala Gly Asp Pro Trp Ile Lys Thr Leu Thr Ala<br>955                  960                965 | 2931 |
| aaa tat ccc ggg gat ttc acg gct tca ttg gac gac tgg cag cgc gaa<br>Lys Tyr Pro Gly Asp Phe Thr Ala Ser Leu Asp Asp Trp Gln Arg Glu<br>970                  975               980              985 | 2979 |
| cac gac gcc att atg gca cgc gtt ctt gat aag ccg cag aca gct gat<br>His Asp Ala Ile Met Ala Arg Val Leu Asp Lys Pro Gln Thr Ala Asp<br>                990                995             1000 | 3027 |
| gtg ttc cag aat aag gtg aac gtc tgc tgg gcg aag gct tta gag<br>Val Phe Gln Asn Lys Val Asn Val Cys Trp Ala Lys Ala Leu Glu<br>               1005             1010             1015 | 3072 |
| cca gtc ttg gcc acg gcc aac att gtg ctg acg aga cag cag tgg<br>Pro Val Leu Ala Thr Ala Asn Ile Val Leu Thr Arg Gln Gln Trp<br>              1020             1025            1030 | 3117 |
| gag acg ttg cac cca ttc aag cat gac aga gcg tac tca cct gaa<br>Glu Thr Leu His Pro Phe Lys His Asp Arg Ala Tyr Ser Pro Glu<br>              1035             1040            1045 | 3162 |
| atg gca ctg aac ttc ttt tgc acc agg ttc ttt gga gta gac ctg<br>Met Ala Leu Asn Phe Phe Cys Thr Arg Phe Phe Gly Val Asp Leu<br>              1050             1055            1060 | 3207 |
| gac agt ggg tta ttt tcc gct cct acc gtc gca ctt act tac agg<br>Asp Ser Gly Leu Phe Ser Ala Pro Thr Val Ala Leu Thr Tyr Arg<br>              1065             1070            1075 | 3252 |
| gat cag cac tgg gat aac tcg cca ggg aag aac atg tat ggg ctt<br>Asp Gln His Trp Asp Asn Ser Pro Gly Lys Asn Met Tyr Gly Leu<br>              1080             1085            1090 | 3297 |
| aat aga gag gta gca aag gag ttg tca cgg cga tat ccg tgc atc | 3342 |

|  |  |  |  |  |  |  |  |  |  |  |  |  |
|--|--|--|--|--|--|--|--|--|--|--|--|--|
| Asn | Arg | Glu | Val | Ala | Lys | Glu | Leu | Ser | Arg | Arg | Tyr | Pro | Cys | Ile |
|  |  |  | 1095 |  |  |  | 1100 |  |  |  | 1105 |  |

```
aca aaa gcg gtt gac aca ggc agg gta gct gat ata agg aat aat          3387
Thr Lys Ala Val Asp Thr Gly Arg Val Ala Asp Ile Arg Asn Asn
        1110                1115                1120 acc atc aag gac tac tct cca aca att aat gtg gtt cca tta aat          3432
Thr Ile Lys Asp Tyr Ser Pro Thr Ile Asn Val Val Pro Leu Asn
        1125                1130                1135 cgc cgg ttg ccc cac tcg ttg atc gtt gac cac aaa gga cag ggt          3477
Arg Arg Leu Pro His Ser Leu Ile Val Asp His Lys Gly Gln Gly
        1140                1145                1150 aca act gat cac agc gga ttc cta tct aag atg aag ggc aaa tct          3522
Thr Thr Asp His Ser Gly Phe Leu Ser Lys Met Lys Gly Lys Ser
        1155                1160                1165 gtg ttg gtg atc ggc gat cct atc agc att cca ggg aag aaa gta          3567
Val Leu Val Ile Gly Asp Pro Ile Ser Ile Pro Gly Lys Lys Val
        1170                1175                1180 gag tcc atg ggt cca ttg ccc act aat acc atc agg tgt gat ctc          3612
Glu Ser Met Gly Pro Leu Pro Thr Asn Thr Ile Arg Cys Asp Leu
        1185                1190                1195 gat ttg gga ata cct agc cat gtc ggt aaa tat gac att atc ttt          3657
Asp Leu Gly Ile Pro Ser His Val Gly Lys Tyr Asp Ile Ile Phe
        1200                1205                1210 gtc aat gtt agg acc ccg tac agg aac cat cac tac caa cag tgc          3702
Val Asn Val Arg Thr Pro Tyr Arg Asn His His Tyr Gln Gln Cys
        1215                1220                1225 gag gat cac gct atc cac cac agc atg cta acg tgt aag gct gtc          3747
Glu Asp His Ala Ile His His Ser Met Leu Thr Cys Lys Ala Val
        1230                1235                1240 cac cac ctg aac act ggc gga aca tgt gtg gct ata ggg tat ggg          3792
His His Leu Asn Thr Gly Gly Thr Cys Val Ala Ile Gly Tyr Gly
        1245                1250                1255 ctt gct gat cgc gca acc gag aat atc atc act gcg gtg gca cgc          3837
Leu Ala Asp Arg Ala Thr Glu Asn Ile Ile Thr Ala Val Ala Arg
        1260                1265                1270 tca ttt agg ttt acc cgt gtc tgt cag cct aag aac act gcc gaa          3882
Ser Phe Arg Phe Thr Arg Val Cys Gln Pro Lys Asn Thr Ala Glu
        1275                1280                1285 aat act gag gtt ctc ttc gtg ttc ttc ggc aag gac aac ggc aac          3927
Asn Thr Glu Val Leu Phe Val Phe Phe Gly Lys Asp Asn Gly Asn
        1290                1295                1300 cac aca cat gac cag gac aga ctc ggt gta gtg ctt gac aac atc          3972
His Thr His Asp Gln Asp Arg Leu Gly Val Val Leu Asp Asn Ile
        1305                1310                1315 tat caa ggg tca acc agg tac gag gca ggg aga gct cca gcg tac          4017
Tyr Gln Gly Ser Thr Arg Tyr Glu Ala Gly Arg Ala Pro Ala Tyr
        1320                1325                1330 aga gtg atc aga ggt gac att agc aag agc gct gac caa gct atc          4062
Arg Val Ile Arg Gly Asp Ile Ser Lys Ser Ala Asp Gln Ala Ile
        1335                1340                1345 gtt aat gct gct aat agc aaa ggt caa cca ggt tcc gga gtg tgc          4107
Val Asn Ala Ala Asn Ser Lys Gly Gln Pro Gly Ser Gly Val Cys
        1350                1355                1360 ggt gca ctg tac cga aaa tgg ccg gct gct ttt gat aga cag cca          4152
Gly Ala Leu Tyr Arg Lys Trp Pro Ala Ala Phe Asp Arg Gln Pro
        1365                1370                1375 ata gct gtc ggg acg gct aga ctt gtg aag cac gaa ccg ctc atc          4197
Ile Ala Val Gly Thr Ala Arg Leu Val Lys His Glu Pro Leu Ile
        1380                1385                1390
```

```
ata cat gct gta gga ccc aat ttt tct aag atg ccg gaa ccg gag     4242
Ile His Ala Val Gly Pro Asn Phe Ser Lys Met Pro Glu Pro Glu
            1395            1400            1405 ggc gac ctt aag ctc gca gct gcc tac atg agc ata gcg tcc atc     4287
Gly Asp Leu Lys Leu Ala Ala Ala Tyr Met Ser Ile Ala Ser Ile
    1410            1415            1420 gtc aac gct gag cgg att aca aaa ata tca gta ccg cta ctg tca     4332
Val Asn Ala Glu Arg Ile Thr Lys Ile Ser Val Pro Leu Leu Ser
1425            1430            1435 acc ggc atc tat tct ggt ggc aaa gat cga gtg atg caa tca ttg     4377
Thr Gly Ile Tyr Ser Gly Gly Lys Asp Arg Val Met Gln Ser Leu
        1440            1445            1450 cat cac ctg ttc act gct ttc gac act acg gat gcc gat gtc acc     4422
His His Leu Phe Thr Ala Phe Asp Thr Thr Asp Ala Asp Val Thr
            1455            1460            1465 ata tat tgc ttg gat aaa caa tgg gag acc agg ata atc gag gcc     4467
Ile Tyr Cys Leu Asp Lys Gln Trp Glu Thr Arg Ile Ile Glu Ala
    1470            1475            1480 att cac cgc aaa gaa agc gtc gaa att ctg gat gat gac aag cca     4512
Ile His Arg Lys Glu Ser Val Glu Ile Leu Asp Asp Asp Lys Pro
1485            1490            1495 gta gac att gac ttg gtc agg gtc cac cca aac agc tct ttg gca     4557
Val Asp Ile Asp Leu Val Arg Val His Pro Asn Ser Ser Leu Ala
        1500            1505            1510 ggc aga cca ggt tac tcc gtc aat gag ggc aag ttg tat tca tac     4602
Gly Arg Pro Gly Tyr Ser Val Asn Glu Gly Lys Leu Tyr Ser Tyr
            1515            1520            1525 ctg gaa ggt aca cga ttc cat cag acc gcc aag gac att gcc gaa     4647
Leu Glu Gly Thr Arg Phe His Gln Thr Ala Lys Asp Ile Ala Glu
    1530            1535            1540 atc cat gca atg tgg ccc aac aaa tct gag gct aat gag cag att     4692
Ile His Ala Met Trp Pro Asn Lys Ser Glu Ala Asn Glu Gln Ile
1545            1550            1555 tgc ttg tac atc ctg ggg gag agt atg tcc agc atc cgc tcc aaa     4737
Cys Leu Tyr Ile Leu Gly Glu Ser Met Ser Ser Ile Arg Ser Lys
        1560            1565            1570 tgc cca gta gag gag tca gag gcg tct gct cca cct cac aca ctt     4782
Cys Pro Val Glu Glu Ser Glu Ala Ser Ala Pro Pro His Thr Leu
            1575            1580            1585 cca tgc ctg tgt aat tac gct atg acg gct gag cgc gta tac agg     4827
Pro Cys Leu Cys Asn Tyr Ala Met Thr Ala Glu Arg Val Tyr Arg
    1590            1595            1600 ttg cgc tct gcg aag aaa gaa cag ttc gcc gta tgc tca tca ttc     4872
Leu Arg Ser Ala Lys Lys Glu Gln Phe Ala Val Cys Ser Ser Phe
1605            1610            1615 ctg ttg ccg aag tac agg atc aca ggc gtg cag aag cta cag tgc     4917
Leu Leu Pro Lys Tyr Arg Ile Thr Gly Val Gln Lys Leu Gln Cys
        1620            1625            1630 agc aaa cca gtc ctg ttt tca ggc gtc gta cca ccg gct gta cac     4962
Ser Lys Pro Val Leu Phe Ser Gly Val Val Pro Pro Ala Val His
            1635            1640            1645 ccc agg aag tac gcg gaa ata att cta gaa acg cca cca ccg cca     5007
Pro Arg Lys Tyr Ala Glu Ile Ile Leu Glu Thr Pro Pro Pro Pro
    1650            1655            1660 gca acg aca acc gta ata tgt gaa cca act gtg cca gaa cgt ata     5052
Ala Thr Thr Thr Val Ile Cys Glu Pro Thr Val Pro Glu Arg Ile
1665            1670            1675 ccc agt ccg gtg att tct aga gca cca agt gcg gaa tca ctg cta     5097
Pro Ser Pro Val Ile Ser Arg Ala Pro Ser Ala Glu Ser Leu Leu
        1680            1685            1690
```

-continued

| | |
|---|---|
| tcg ctt ggc ggc gtc tcg ttc tct agc tct gcc aca cgc tcg tca<br>Ser Leu Gly Gly Val Ser Phe Ser Ser Ser Ala Thr Arg Ser Ser<br>1695                   1700                   1705 | 5142 |
| acc gcc tgg agc gac tat gac agg cgg ttt gtg gtt aca gct gat<br>Thr Ala Trp Ser Asp Tyr Asp Arg Arg Phe Val Val Thr Ala Asp<br>1710                   1715                   1720 | 5187 |
| gtg cat caa gcg aac acg tct acg tgg agc atc cct agt gct cct<br>Val His Gln Ala Asn Thr Ser Thr Trp Ser Ile Pro Ser Ala Pro<br>1725                   1730                   1735 | 5232 |
| ggc ttg gac gtc cag ctg cct tct gac gtc act gat tcc cac tgg<br>Gly Leu Asp Val Gln Leu Pro Ser Asp Val Thr Asp Ser His Trp<br>1740                   1745                   1750 | 5277 |
| agt att cca agt gca tca ggc ttt gaa gtg aga aca cca tct gta<br>Ser Ile Pro Ser Ala Ser Gly Phe Glu Val Arg Thr Pro Ser Val<br>1755                   1760                   1765 | 5322 |
| cag gac cta act gcg gag tgt gcg aag cct cgt gga ctg gcc gaa<br>Gln Asp Leu Thr Ala Glu Cys Ala Lys Pro Arg Gly Leu Ala Glu<br>1770                   1775                   1780 | 5367 |
| ata atg caa gac ttc aat act gct cct ttc cag ttt ctt tcg gac<br>Ile Met Gln Asp Phe Asn Thr Ala Pro Phe Gln Phe Leu Ser Asp<br>1785                   1790                   1795 | 5412 |
| tac aga cca gta ccg gca cca cgg aga cgc ccc atc cca tca cct<br>Tyr Arg Pro Val Pro Ala Pro Arg Arg Arg Pro Ile Pro Ser Pro<br>1800                   1805                   1810 | 5457 |
| aga tcg acg gct tcc gca cct cca gtt cca aag cca cgc agg act<br>Arg Ser Thr Ala Ser Ala Pro Pro Val Pro Lys Pro Arg Arg Thr<br>1815                   1820                   1825 | 5502 |
| aag tac caa caa cca cca gga gtc gct aga gcg atc tca gaa gcg<br>Lys Tyr Gln Gln Pro Pro Gly Val Ala Arg Ala Ile Ser Glu Ala<br>1830                   1835                   1840 | 5547 |
| gag ttg gac gag tac atc cgt caa cac tcc aac tga cgg tat gaa<br>Glu Leu Asp Glu Tyr Ile Arg Gln His Ser Asn     Arg Tyr Glu<br>1845                   1850                   1855 | 5592 |
| gcg gga gcg tat att ttc tca tcg gaa aca ggc caa ggt cac ctt<br>Ala Gly Ala Tyr Ile Phe Ser Ser Glu Thr Gly Gln Gly His Leu<br>1860                   1865                   1870 | 5637 |
| caa cag aaa tca gta cgt caa tgt aaa cta caa gaa cct ata ttg<br>Gln Gln Lys Ser Val Arg Gln Cys Lys Leu Gln Glu Pro Ile Leu<br>1875                   1880                   1885 | 5682 |
| gat cgg gcc gtc cat gag aag tat tac gcc ccg cgc ctc gat ctc<br>Asp Arg Ala Val His Glu Lys Tyr Tyr Ala Pro Arg Leu Asp Leu<br>1890                   1895                   1900 | 5727 |
| gaa aga gag aaa atg tta cag aag aaa ctg caa tta tgc gcc tct<br>Glu Arg Glu Lys Met Leu Gln Lys Lys Leu Gln Leu Cys Ala Ser<br>1905                   1910                   1915 | 5772 |
| gaa gga aat aga agc agg tat caa tca cga aaa gta gaa aat atg<br>Glu Gly Asn Arg Ser Arg Tyr Gln Ser Arg Lys Val Glu Asn Met<br>1920                   1925                   1930 | 5817 |
| aaa gca att aca gcg gag cga ctc att tct gga ttg ggc aca tat<br>Lys Ala Ile Thr Ala Glu Arg Leu Ile Ser Gly Leu Gly Thr Tyr<br>1935                   1940                   1945 | 5862 |
| cta tca tca gaa gtg aat cct gtc gag tgt tac aga gtc aat tat<br>Leu Ser Ser Glu Val Asn Pro Val Glu Cys Tyr Arg Val Asn Tyr<br>1950                   1955                   1960 | 5907 |
| cct gta cca atc tac tcg tca acg gta att aac agg ttt aca tct<br>Pro Val Pro Ile Tyr Ser Ser Thr Val Ile Asn Arg Phe Thr Ser<br>1965                   1970                   1975 | 5952 |
| gca gag gtc gcg gtt aaa acg tgc aac tta gtt atc caa gag aat<br>Ala Glu Val Ala Val Lys Thr Cys Asn Leu Val Ile Gln Glu Asn | 5997 |

```
                          1980              1985              1990
tac cct aca gta gcc   agt tat tgt ata aca   gat gaa tac gat gcg   6042
Tyr Pro Thr Val Ala   Ser Tyr Cys Ile Thr   Asp Glu Tyr Asp Ala
                1995                  2000                  2005 tat ctt gac atg gtg   gac ggc gca tcg tgc   tgt cta gat aca gcc   6087
Tyr Leu Asp Met Val   Asp Gly Ala Ser Cys   Cys Leu Asp Thr Ala
                2010                  2015                  2020 act ttt tgt ccg gct   aaa ctg aga agc tac   cca aag aag cat agc   6132
Thr Phe Cys Pro Ala   Lys Leu Arg Ser Tyr   Pro Lys Lys His Ser
                2025                  2030                  2035 tat ttg cag cca gag   ata aga tca gcc gtc   cca tcg cct ata cag   6177
Tyr Leu Gln Pro Glu   Ile Arg Ser Ala Val   Pro Ser Pro Ile Gln
                2040                  2045                  2050 aat aca tta caa aat   gta ttg gct gca gct   act aaa agg aat tgc   6222
Asn Thr Leu Gln Asn   Val Leu Ala Ala Ala   Thr Lys Arg Asn Cys
                2055                  2060                  2065 aac gtt acc caa atg   cga gaa tta cct gtc   tta gat tcg gcg gca   6267
Asn Val Thr Gln Met   Arg Glu Leu Pro Val   Leu Asp Ser Ala Ala
                2070                  2075                  2080 ttt aat gtt gat tgt   ttc aag aaa tac gca   tgc aat gat gag tac   6312
Phe Asn Val Asp Cys   Phe Lys Lys Tyr Ala   Cys Asn Asp Glu Tyr
                2085                  2090                  2095 tgg gat acc ttt cgc   gat aac cct att cgg   cta act aca gag aac   6357
Trp Asp Thr Phe Arg   Asp Asn Pro Ile Arg   Leu Thr Thr Glu Asn
                2100                  2105                  2110 gtt acg caa tat gtg   aca aag ctg aaa ggg   ccg aaa gca gca gca   6402
Val Thr Gln Tyr Val   Thr Lys Leu Lys Gly   Pro Lys Ala Ala Ala
                2115                  2120                  2125 ttg ttt gcg aat act   cat aat cta aaa ccg   ttg cag gag ata cca   6447
Leu Phe Ala Asn Thr   His Asn Leu Lys Pro   Leu Gln Glu Ile Pro
                2130                  2135                  2140 atg gat caa ttc gtc   atg gat cta aag aga   gat gtc aaa gtt act   6492
Met Asp Gln Phe Val   Met Asp Leu Lys Arg   Asp Val Lys Val Thr
                2145                  2150                  2155 ccc ggc acg aaa cat   aca gag gag cgg cct   aag gtg cag gtt att   6537
Pro Gly Thr Lys His   Thr Glu Glu Arg Pro   Lys Val Gln Val Ile
                2160                  2165                  2170 cag gct gca gat ccc   ctt gct acc gct tac   ctt tgc ggg atc cat   6582
Gln Ala Ala Asp Pro   Leu Ala Thr Ala Tyr   Leu Cys Gly Ile His
                2175                  2180                  2185 cgg gaa tta gtc cgt   aga ctg aat gcg gtg   ctt ctg cca aat atc   6627
Arg Glu Leu Val Arg   Arg Leu Asn Ala Val   Leu Leu Pro Asn Ile
                2190                  2195                  2200 cat act ctc ttc gac   atg tca gcg gaa gat   ttt gat gcg att att   6672
His Thr Leu Phe Asp   Met Ser Ala Glu Asp   Phe Asp Ala Ile Ile
                2205                  2210                  2215 gct gaa cat ttc cac   cac ggc gac cca gta   ttg gaa acg gac atc   6717
Ala Glu His Phe His   His Gly Asp Pro Val   Leu Glu Thr Asp Ile
                2220                  2225                  2230 gcg tcg ttt gat aaa   agc gaa gac gac gct   atc gcc att tcg gcg   6762
Ala Ser Phe Asp Lys   Ser Glu Asp Asp Ala   Ile Ala Ile Ser Ala
                2235                  2240                  2245 ttg atg atc ctt gag   gac tta ggt gtc gac   caa ccg ctc tta gat   6807
Leu Met Ile Leu Glu   Asp Leu Gly Val Asp   Gln Pro Leu Leu Asp
                2250                  2255                  2260 ttg ata gag gcg gcg   ttc ggc aat atc aca   tct gtg cac cta cct   6852
Leu Ile Glu Ala Ala   Phe Gly Asn Ile Thr   Ser Val His Leu Pro
                2265                  2270                  2275 aca gga acg agg ttt   aaa ttt ggt gcc atg   atg aaa tcc ggt atg   6897
```

```
        Thr Gly Thr Arg Phe Lys Phe Gly Ala Met Met Lys Ser Gly Met
                        2280                2285            2290 ttc tta acg ctg ttt gtc aac aca cta gtc aat atc atg att gct              6942
Phe Leu Thr Leu Phe Val Asn Thr Leu Val Asn Ile Met Ile Ala
                2295                2300                2305 agc aga gta cta cgt gaa cgg tta acc acg tca gcg tgc gcg gcc              6987
Ser Arg Val Leu Arg Glu Arg Leu Thr Thr Ser Ala Cys Ala Ala
                2310                2315                2320 tct atc ggc gac gat aac ata gtg cat ggt gtc gtc tcc gac acc              7032
Ser Ile Gly Asp Asp Asn Ile Val His Gly Val Val Ser Asp Thr
                2325                2330                2335 ttg atg gcg gag aga tgc gcc act tgg ctg aac atg gaa gta aaa              7077
Leu Met Ala Glu Arg Cys Ala Thr Trp Leu Asn Met Glu Val Lys
                2340                2345                2350 att att gat gca gtt att ggt atc aaa gca ccc tac ttc tgt ggg              7122
Ile Ile Asp Ala Val Ile Gly Ile Lys Ala Pro Tyr Phe Cys Gly
                2355                2360                2365 gga ttt atc ctg gtg gac cag ata aca ggc aca gcc tgc aga gtc              7167
Gly Phe Ile Leu Val Asp Gln Ile Thr Gly Thr Ala Cys Arg Val
                2370                2375                2380 gca gac cct cta aaa agg ctt ttt aag ctt gga aaa cca ttg cca              7212
Ala Asp Pro Leu Lys Arg Leu Phe Lys Leu Gly Lys Pro Leu Pro
                2385                2390                2395 gtc gat gat acc caa gac tgc gac cgc cgc cgg gca ctg cat gat              7257
Val Asp Asp Thr Gln Asp Cys Asp Arg Arg Arg Ala Leu His Asp
                2400                2405                2410 gaa gca atg cga tgg aac aga att gga att acg gac gag tta gtg              7302
Glu Ala Met Arg Trp Asn Arg Ile Gly Ile Thr Asp Glu Leu Val
                2415                2420                2425 aag gcc gta gaa tcc aga tac gag atc ata ctg gca ggc ctg atc              7347
Lys Ala Val Glu Ser Arg Tyr Glu Ile Ile Leu Ala Gly Leu Ile
                2430                2435                2440 atc acg tct ctg tcc acg tta gcc gaa agc gtt aag aac ttc aag              7392
Ile Thr Ser Leu Ser Thr Leu Ala Glu Ser Val Lys Asn Phe Lys
                2445                2450                2455 agc ata aga ggg agc cca atc acc ctc tac ggc tga cctaaatagg               7438
Ser Ile Arg Gly Ser Pro Ile Thr Leu Tyr Gly
                2460                2465 tgacgtagta gacacgcacc tacccaccgg caga atg ttt cca tac cct cag            7490
                                     Met Phe Pro Tyr Pro Gln
                                                     2470 ctg aac ttt cca cca gtt tac cct aca aat ccg atg gct tac cga              7535
Leu Asn Phe Pro Pro Val Tyr Pro Thr Asn Pro Met Ala Tyr Arg
                2475                2480                2485 gat cca aac cct cct agg cgc cgc tgg agg ccg ttt cgg ccc ccg              7580
Asp Pro Asn Pro Pro Arg Arg Arg Trp Arg Pro Phe Arg Pro Pro
                2490                2495                2500 ctg gct gct caa atc gaa gat ctt agg agg tcg ata gtc aac ttg              7625
Leu Ala Ala Gln Ile Glu Asp Leu Arg Arg Ser Ile Val Asn Leu
                2505                2510                2515 act ttc aaa caa cga tca cct aat ccg ccg cca ggt cca ccg cca              7670
Thr Phe Lys Gln Arg Ser Pro Asn Pro Pro Pro Gly Pro Pro Pro
                2520                2525                2530 aag aag aag aag agt gct cct aag cca aaa cct act cag cct aaa              7715
Lys Lys Lys Lys Ser Ala Pro Lys Pro Lys Pro Thr Gln Pro Lys
                2535                2540                2545 aag aag aag cag caa gcc aag agg acg aaa cgc aag cct aaa cca              7760
Lys Lys Lys Gln Gln Ala Lys Arg Thr Lys Arg Lys Pro Lys Pro
                2550                2555                2560
```

```
ggg aaa cga caa cgt atg tgt atg aag ttg gag tcg gac aag aca      7805
Gly Lys Arg Gln Arg Met Cys Met Lys Leu Glu Ser Asp Lys Thr
        2565                2570                2575 ttt ccg atc atg ctg aac ggc caa gtg aat gga tat gcc tgc gtt      7850
Phe Pro Ile Met Leu Asn Gly Gln Val Asn Gly Tyr Ala Cys Val
        2580                2585                2590 gtc gga gga agg ctg atg aaa cca ctc cac gtt gaa gga aaa att      7895
Val Gly Gly Arg Leu Met Lys Pro Leu His Val Glu Gly Lys Ile
        2595                2600                2605 gat aat gag caa tta gcg gcc gtg aaa ttg aag aag gct agc atg      7940
Asp Asn Glu Gln Leu Ala Ala Val Lys Leu Lys Lys Ala Ser Met
        2610                2615                2620 tac gac ttg gag tac ggc gac gtt ccc cag aac atg aaa tca gac      7985
Tyr Asp Leu Glu Tyr Gly Asp Val Pro Gln Asn Met Lys Ser Asp
        2625                2630                2635 acg ctg cag tac acc agc gac aaa cca ccg ggc ttc tac aac tgg      8030
Thr Leu Gln Tyr Thr Ser Asp Lys Pro Pro Gly Phe Tyr Asn Trp
        2640                2645                2650 cac cac ggc gca gtc cag tat gag aat ggg aga ttt acc gta ccg      8075
His His Gly Ala Val Gln Tyr Glu Asn Gly Arg Phe Thr Val Pro
        2655                2660                2665 aga gga gtg ggc ggg aaa ggc gac agc gga aga ccg atc ctg gac      8120
Arg Gly Val Gly Gly Lys Gly Asp Ser Gly Arg Pro Ile Leu Asp
        2670                2675                2680 aac aga ggc aga gtt gtg gct att gtt cta gga ggt gca aat gag      8165
Asn Arg Gly Arg Val Val Ala Ile Val Leu Gly Gly Ala Asn Glu
        2685                2690                2695 ggc acg cgt acg gcg ctt tca gtg gtc act tgg aac cag aaa ggg      8210
Gly Thr Arg Thr Ala Leu Ser Val Val Thr Trp Asn Gln Lys Gly
        2700                2705                2710 gtg acc att agg gat acc ccc gaa ggt tct gaa ccg tgg tca cta      8255
Val Thr Ile Arg Asp Thr Pro Glu Gly Ser Glu Pro Trp Ser Leu
        2715                2720                2725 gtt aca gcg cta tgc gtg ctt tcg aat gtc acg ttc cca tgc gac      8300
Val Thr Ala Leu Cys Val Leu Ser Asn Val Thr Phe Pro Cys Asp
        2730                2735                2740 aaa cca ccc gtg tgc tat tca ctg acg cca gaa cga aca ctc gac      8345
Lys Pro Pro Val Cys Tyr Ser Leu Thr Pro Glu Arg Thr Leu Asp
        2745                2750                2755 gtg ctc gaa gag aac gtc gac aat cca aat tac gac acg ctg ctg      8390
Val Leu Glu Glu Asn Val Asp Asn Pro Asn Tyr Asp Thr Leu Leu
        2760                2765                2770 gag aac gtc ttg aaa tgt cca tca cgc cgg ccc aaa cga agc att      8435
Glu Asn Val Leu Lys Cys Pro Ser Arg Arg Pro Lys Arg Ser Ile
        2775                2780                2785 acc gat gac ttc aca ctg acc agt ccc tac ctg ggg ttc tgc ccg      8480
Thr Asp Asp Phe Thr Leu Thr Ser Pro Tyr Leu Gly Phe Cys Pro
        2790                2795                2800 tat tgc aga cac tca acg ccg tgt ttc agc cca ata aaa att gag      8525
Tyr Cys Arg His Ser Thr Pro Cys Phe Ser Pro Ile Lys Ile Glu
        2805                2810                2815 aac gtg tgg gac gaa tct gat gat gga tcg att aga atc cag gtc      8570
Asn Val Trp Asp Glu Ser Asp Asp Gly Ser Ile Arg Ile Gln Val
        2820                2825                2830 tcg gca caa ttc ggc tac aat cag gca ggc act gcg gat gtc acc      8615
Ser Ala Gln Phe Gly Tyr Asn Gln Ala Gly Thr Ala Asp Val Thr
        2835                2840                2845 aaa ttc cgt tac atg tct ttc gac cac gac cat gac atc aag gaa      8660
Lys Phe Arg Tyr Met Ser Phe Asp His Asp His Asp Ile Lys Glu
        2850                2855                2860
```

```
gac agt atg gag aaa ata gct atc agc aca tct gga ccc tgc cgt      8705
Asp Ser Met Glu Lys Ile Ala Ile Ser Thr Ser Gly Pro Cys Arg
        2865            2870            2875 cgt ctt ggc cac aaa ggg tac ttc ctg tta gct caa tgt cct cca      8750
Arg Leu Gly His Lys Gly Tyr Phe Leu Leu Ala Gln Cys Pro Pro
        2880            2885            2890 ggt gac agt gta acc gtc agt atc acg agc gga gca tct gag aat      8795
Gly Asp Ser Val Thr Val Ser Ile Thr Ser Gly Ala Ser Glu Asn
        2895            2900            2905 tca tgc acc gtg gag aaa aag atc agg agg aag ttt gtc ggt aga      8840
Ser Cys Thr Val Glu Lys Lys Ile Arg Arg Lys Phe Val Gly Arg
        2910            2915            2920 gag gag tac ttg ttc cca ccc gtc cat gga aag ctg gta aag tgc      8885
Glu Glu Tyr Leu Phe Pro Pro Val His Gly Lys Leu Val Lys Cys
        2925            2930            2935 cac gtt tac gat cac ttg aag gag acg tct gcc ggg tac ata acc      8930
His Val Tyr Asp His Leu Lys Glu Thr Ser Ala Gly Tyr Ile Thr
        2940            2945            2950 atg cac agg cca ggc cca cac gcg tat aag tcc tat ctg gag gaa      8975
Met His Arg Pro Gly Pro His Ala Tyr Lys Ser Tyr Leu Glu Glu
        2955            2960            2965 gcg tca ggc gaa gtg tac att aaa cca cct tct ggc aag aac gtc      9020
Ala Ser Gly Glu Val Tyr Ile Lys Pro Pro Ser Gly Lys Asn Val
        2970            2975            2980 acc tac gaa tgt aag tgt ggc gac tac agc aca ggt atc gtg agc      9065
Thr Tyr Glu Cys Lys Cys Gly Asp Tyr Ser Thr Gly Ile Val Ser
        2985            2990            2995 acg cga acg aag atg aac ggc tgc act aaa gca aaa cag tgc att      9110
Thr Arg Thr Lys Met Asn Gly Cys Thr Lys Ala Lys Gln Cys Ile
        3000            3005            3010 gcc tac aag agc gac caa acg aaa tgg gtc ttc aac tcg ccg gat      9155
Ala Tyr Lys Ser Asp Gln Thr Lys Trp Val Phe Asn Ser Pro Asp
        3015            3020            3025 ctt att agg cac aca gac cac tca gtg caa ggt aaa ttg cac att      9200
Leu Ile Arg His Thr Asp His Ser Val Gln Gly Lys Leu His Ile
        3030            3035            3040 cca ttc cgc ttg aca ccg aca gtc tgc ccg gtt ccg tta gct cac      9245
Pro Phe Arg Leu Thr Pro Thr Val Cys Pro Val Pro Leu Ala His
        3045            3050            3055 acg cct aca gtc acg aag tgg ttc aaa ggc atc acc ctc cac ctg      9290
Thr Pro Thr Val Thr Lys Trp Phe Lys Gly Ile Thr Leu His Leu
        3060            3065            3070 act gca atg cga cca aca ttg ctg aca acg aga aaa ttg ggg ctg      9335
Thr Ala Met Arg Pro Thr Leu Leu Thr Thr Arg Lys Leu Gly Leu
        3075            3080            3085 cga gca gac gca aca gca gaa tgg att aca ggg tct aca tcc agg      9380
Arg Ala Asp Ala Thr Ala Glu Trp Ile Thr Gly Ser Thr Ser Arg
        3090            3095            3100 aat ttt tct gtg ggg cga gaa ggg ctg gag tac gta tgg ggt aac      9425
Asn Phe Ser Val Gly Arg Glu Gly Leu Glu Tyr Val Trp Gly Asn
        3105            3110            3115 cat gaa cca gtc aga gtc tgg gcc cag gag tcg gca cca ggc gac      9470
His Glu Pro Val Arg Val Trp Ala Gln Glu Ser Ala Pro Gly Asp
        3120            3125            3130 cca cat gga tgg ccg cat gag atc atc atc cac tat tat cat cgg      9515
Pro His Gly Trp Pro His Glu Ile Ile Ile His Tyr Tyr His Arg
        3135            3140            3145 cat cca gtc tac act gtc att gtg ctg tgt ggt gtc gct ctt gct      9560
His Pro Val Tyr Thr Val Ile Val Leu Cys Gly Val Ala Leu Ala
```

-continued

| | | | | | | | | | | | | | | |
|---|---|---|---|---|---|---|---|---|---|---|---|---|---|---|
| | | 3150 | | | | 3155 | | | | 3160 | | | | |
| atc | ctg | gta | ggc | act | gca | tca | tca | gca | gct | tgc | atc | gcc | aaa gca | 9605 |
| Ile | Leu | Val | Gly | Thr | Ala | Ser | Ser | Ala | Ala | Cys | Ile | Ala | Lys Ala | |
| | | 3165 | | | | 3170 | | | | 3175 | | | | |
| aga | aga | gac | tgc | ctg | acg | cca | tac | gcg | ctt | gca | ccg | aac | gca acg | 9650 |
| Arg | Arg | Asp | Cys | Leu | Thr | Pro | Tyr | Ala | Leu | Ala | Pro | Asn | Ala Thr | |
| | | 3180 | | | | 3185 | | | | 3190 | | | | |
| gta | ccc | aca | gca | tta | gcg | gtt | ttg | tgc | tgc | att | cgg | cca | acc aac | 9695 |
| Val | Pro | Thr | Ala | Leu | Ala | Val | Leu | Cys | Cys | Ile | Arg | Pro | Thr Asn | |
| | | 3195 | | | | 3200 | | | | 3205 | | | | |
| gct | gaa | aca | ttt | gga | gaa | act | ttg | aac | cat | ctg | tgg | ttt | aac aac | 9740 |
| Ala | Glu | Thr | Phe | Gly | Glu | Thr | Leu | Asn | His | Leu | Trp | Phe | Asn Asn | |
| | | 3210 | | | | 3215 | | | | 3220 | | | | |
| caa | ccg | ttt | ctc | tgg | gca | cag | ttg | tgc | att | cct | ctg | gca | gcg ctt | 9785 |
| Gln | Pro | Phe | Leu | Trp | Ala | Gln | Leu | Cys | Ile | Pro | Leu | Ala | Ala Leu | |
| | | 3225 | | | | 3230 | | | | 3235 | | | | |
| gtt | att | ctg | ttc | cgc | tgc | ttt | tca | tgc | tgc | atg | cct | ttt | tta ttg | 9830 |
| Val | Ile | Leu | Phe | Arg | Cys | Phe | Ser | Cys | Cys | Met | Pro | Phe | Leu Leu | |
| | | 3240 | | | | 3245 | | | | 3250 | | | | |
| gtt | gca | ggc | gtc | tgc | ctg | ggg | aag | gta | gac | gcc | ttc | gaa | cat gcg | 9875 |
| Val | Ala | Gly | Val | Cys | Leu | Gly | Lys | Val | Asp | Ala | Phe | Glu | His Ala | |
| | | 3255 | | | | 3260 | | | | 3265 | | | | |
| acc | act | gtg | cca | aat | gtt | ccg | ggg | atc | ccg | tat | aag | gcg | ttg gtc | 9920 |
| Thr | Thr | Val | Pro | Asn | Val | Pro | Gly | Ile | Pro | Tyr | Lys | Ala | Leu Val | |
| | | 3270 | | | | 3275 | | | | 3280 | | | | |
| gaa | cgc | gca | ggt | tac | gcg | cca | ctt | aac | ctg | gag | atc | acg | gtc gtc | 9965 |
| Glu | Arg | Ala | Gly | Tyr | Ala | Pro | Leu | Asn | Leu | Glu | Ile | Thr | Val Val | |
| | | 3285 | | | | 3290 | | | | 3295 | | | | |
| tca | tcg | gaa | tta | aca | cct | tca | act | aac | aag | gag | tac | gtg | acc tgc | 10010 |
| Ser | Ser | Glu | Leu | Thr | Pro | Ser | Thr | Asn | Lys | Glu | Tyr | Val | Thr Cys | |
| | | 3300 | | | | 3305 | | | | 3310 | | | | |
| aaa | ttc | cac | aca | gtc | att | cct | tca | cca | caa | gtt | aaa | tgc | tgc ggg | 10055 |
| Lys | Phe | His | Thr | Val | Ile | Pro | Ser | Pro | Gln | Val | Lys | Cys | Cys Gly | |
| | | 3315 | | | | 3320 | | | | 3325 | | | | |
| tcc | ctc | gag | tgc | aag | gca | tcc | tca | aag | gcg | gat | tac | aca | tgc cgc | 10100 |
| Ser | Leu | Glu | Cys | Lys | Ala | Ser | Ser | Lys | Ala | Asp | Tyr | Thr | Cys Arg | |
| | | 3330 | | | | 3335 | | | | 3340 | | | | |
| gtt | ttt | ggc | ggt | gtg | tac | cct | ttc | atg | tgg | gga | ggc | gca | caa tgc | 10145 |
| Val | Phe | Gly | Gly | Val | Tyr | Pro | Phe | Met | Trp | Gly | Gly | Ala | Gln Cys | |
| | | 3345 | | | | 3350 | | | | 3355 | | | | |
| ttc | tgt | gac | agt | gag | aac | aca | caa | ctg | agt | gag | gcg | tac | gtc gag | 10190 |
| Phe | Cys | Asp | Ser | Glu | Asn | Thr | Gln | Leu | Ser | Glu | Ala | Tyr | Val Glu | |
| | | 3360 | | | | 3365 | | | | 3370 | | | | |
| ttc | gct | cca | gac | tgc | act | ata | gat | cac | gca | gtc | gca | cta | aaa gtt | 10235 |
| Phe | Ala | Pro | Asp | Cys | Thr | Ile | Asp | His | Ala | Val | Ala | Leu | Lys Val | |
| | | 3375 | | | | 3380 | | | | 3385 | | | | |
| cac | aca | gct | gct | ctg | aaa | gtc | ggc | ctg | cgt | ata | gta | tac | ggc aac | 10280 |
| His | Thr | Ala | Ala | Leu | Lys | Val | Gly | Leu | Arg | Ile | Val | Tyr | Gly Asn | |
| | | 3390 | | | | 3395 | | | | 3400 | | | | |
| acc | acc | gcg | cac | ctg | gat | acg | ttt | gtc | aat | ggc | gtc | acg | cca ggt | 10325 |
| Thr | Thr | Ala | His | Leu | Asp | Thr | Phe | Val | Asn | Gly | Val | Thr | Pro Gly | |
| | | 3405 | | | | 3410 | | | | 3415 | | | | |
| tcc | tca | cgg | gac | ctg | aag | gtc | ata | gca | ggg | ccg | ata | tca | gcc gct | 10370 |
| Ser | Ser | Arg | Asp | Leu | Lys | Val | Ile | Ala | Gly | Pro | Ile | Ser | Ala Ala | |
| | | 3420 | | | | 3425 | | | | 3430 | | | | |
| ttt | tca | ccc | ttt | gac | cat | aag | gtc | gtc | atc | aga | aag | ggg | ctt gtt | 10415 |
| Phe | Ser | Pro | Phe | Asp | His | Lys | Val | Val | Ile | Arg | Lys | Gly | Leu Val | |
| | | 3435 | | | | 3440 | | | | 3445 | | | | |
| tac | aac | tac | gac | ttc | cct | gag | tat | gga | gct | atg | aaa | cca | gga gcg | 10460 |

-continued

| | | | | | | | | | | | |
|---|---|---|---|---|---|---|---|---|---|---|---|
| Tyr | Asn | Tyr | Asp | Phe | Pro | Glu | Tyr | Gly | Ala | Met | Lys | Pro | Gly | Ala |
| | | 3450 | | | | 3455 | | | | 3460 | | | | |

```
ttc  ggc  gat  att  caa  gca  tcc  tcg  ctt  gat  gct  aca  gac  ata  gta       10505
Phe  Gly  Asp  Ile  Gln  Ala  Ser  Ser  Leu  Asp  Ala  Thr  Asp  Ile  Val
          3465                3470                3475 gcc  cgc  act  gac  ata  cgg  ctg  ctg  aag  cct  tct  gtc  aag  aac  atc       10550
Ala  Arg  Thr  Asp  Ile  Arg  Leu  Leu  Lys  Pro  Ser  Val  Lys  Asn  Ile
          3480                3485                3490 cac  gtc  ccc  tac  acc  caa  gca  gta  tca  ggg  tat  gaa  atg  tgg  aag       10595
His  Val  Pro  Tyr  Thr  Gln  Ala  Val  Ser  Gly  Tyr  Glu  Met  Trp  Lys
          3495                3500                3505 aac  aac  tca  gga  cga  ccc  ctg  caa  gaa  aca  gca  cca  ttt  gga  tgt       10640
Asn  Asn  Ser  Gly  Arg  Pro  Leu  Gln  Glu  Thr  Ala  Pro  Phe  Gly  Cys
          3510                3515                3520 aaa  att  gaa  gtg  gag  cct  ctg  cga  gcg  tct  aac  tgt  gct  tac  ggg       10685
Lys  Ile  Glu  Val  Glu  Pro  Leu  Arg  Ala  Ser  Asn  Cys  Ala  Tyr  Gly
          3525                3530                3535 cac  atc  cct  atc  tcg  att  gac  atc  cct  gat  gca  gct  ttt  gtg  aga       10730
His  Ile  Pro  Ile  Ser  Ile  Asp  Ile  Pro  Asp  Ala  Ala  Phe  Val  Arg
          3540                3545                3550 tca  tca  gaa  tca  cca  aca  att  tta  gaa  gtt  agc  tgc  aca  gta  gca       10775
Ser  Ser  Glu  Ser  Pro  Thr  Ile  Leu  Glu  Val  Ser  Cys  Thr  Val  Ala
          3555                3560                3565 gac  tgc  att  tat  tct  gca  gac  ttt  ggt  ggt  tct  cta  aca  tta  cag       10820
Asp  Cys  Ile  Tyr  Ser  Ala  Asp  Phe  Gly  Gly  Ser  Leu  Thr  Leu  Gln
          3570                3575                3580 tac  aaa  gct  gac  agg  gag  gga  cat  tgt  cca  gtt  cac  tcc  cac  tcc       10865
Tyr  Lys  Ala  Asp  Arg  Glu  Gly  His  Cys  Pro  Val  His  Ser  His  Ser
          3585                3590                3595 acg  aca  gct  gtt  ttg  aag  gaa  gcg  acc  aca  cat  gtg  act  gcc  gta       10910
Thr  Thr  Ala  Val  Leu  Lys  Glu  Ala  Thr  Thr  His  Val  Thr  Ala  Val
          3600                3605                3610 ggc  agc  ata  aca  cta  cat  ttt  agc  aca  tcg  agc  cca  caa  gca  aat       10955
Gly  Ser  Ile  Thr  Leu  His  Phe  Ser  Thr  Ser  Ser  Pro  Gln  Ala  Asn
          3615                3620                3625 ttt  ata  gtt  tcg  cta  tgc  ggc  aag  aag  tcc  acc  tgc  aat  gct  gaa       11000
Phe  Ile  Val  Ser  Leu  Cys  Gly  Lys  Lys  Ser  Thr  Cys  Asn  Ala  Glu
          3630                3635                3640 tgt  aaa  cca  ccg  gcc  gac  cac  ata  att  gga  gaa  cca  cat  aaa  gtc       11045
Cys  Lys  Pro  Pro  Ala  Asp  His  Ile  Ile  Gly  Glu  Pro  His  Lys  Val
          3645                3650                3655 gac  caa  gaa  ttc  cag  gcg  gca  gtt  tcc  aaa  aca  tct  tgg  aac  tgg       11090
Asp  Gln  Glu  Phe  Gln  Ala  Ala  Val  Ser  Lys  Thr  Ser  Trp  Asn  Trp
          3660                3665                3670 ctg  ctt  gca  ctg  ttt  ggg  gga  gca  tca  tcc  ctc  att  gtt  gta  gga       11135
Leu  Leu  Ala  Leu  Phe  Gly  Gly  Ala  Ser  Ser  Leu  Ile  Val  Val  Gly
          3675                3680                3685 ctt  ata  gtg  ttg  gtc  tgc  agc  tct  atg  ctt  ata  aac  aca  cgt  aga       11180
Leu  Ile  Val  Leu  Val  Cys  Ser  Ser  Met  Leu  Ile  Asn  Thr  Arg  Arg
          3690                3695                3700 tga ctgagcgcgg acactgacat agcggtaaaa ctcgatgtac ttccgaggaa            11233
gcgtggtgca taatgccacg cgccgcttga cactaaaact cgatgtattt ccgaggaagc    11293
acagtgcata atgctgtgca gtgtcacatt aatcgtatat cacactacat attaacaaca    11353
ctatatcact tttatgagac tcactatggg tctctaatat acactacaca tattttactt    11413
aaaaacacta tacacacttt ataaattctt ttataatttt tcttttgttt ttattttgtt    11473
tttaaaattt c                                                          11484
```

```
<210> SEQ ID NO 2
<211> LENGTH: 1852
<212> TYPE: PRT
<213> ORGANISM: Western equine encephalomyelitis virus - strain 71V-1658

<400> SEQUENCE: 2

Met Glu Arg Ile His Val Asp Leu Asp Ala Asp Ser Pro Tyr Val Lys
1               5                   10                  15

Ser Leu Gln Arg Thr Phe Pro Gln Phe Glu Ile Glu Ala Arg Gln Val
            20                  25                  30

Thr Asp Asn Asp His Ala Asn Ala Arg Ala Phe Ser His Val Ala Thr
        35                  40                  45

Lys Leu Ile Glu Ser Glu Val Asp Arg Asp Gln Val Ile Leu Asp Ile
    50                  55                  60

Gly Ser Ala Pro Val Arg His Ala His Ser Asn His Arg Tyr His Cys
65                  70                  75                  80

Ile Cys Pro Met Ile Ser Ala Glu Asp Pro Asp Arg Leu Gln Arg Tyr
                85                  90                  95

Ala Glu Arg Leu Lys Lys Ser Asp Ile Thr Asp Lys Asn Ile Ala Ser
            100                 105                 110

Lys Ala Ala Asp Leu Leu Glu Val Met Ser Thr Pro Asp Ala Glu Thr
        115                 120                 125

Pro Ser Leu Cys Met His Thr Asp Ala Thr Cys Arg Tyr Phe Gly Ser
    130                 135                 140

Val Ala Val Tyr Gln Asp Val Tyr Ala Val His Ala Pro Thr Ser Ile
145                 150                 155                 160

Tyr His Gln Ala Leu Lys Gly Val Arg Thr Ile Tyr Trp Ile Gly Phe
                165                 170                 175

Asp Thr Thr Pro Phe Met Tyr Lys Asn Met Ala Gly Ser Tyr Pro Thr
            180                 185                 190

Tyr Asn Thr Asn Trp Ala Asp Glu Arg Val Leu Glu Ala Arg Asn Ile
        195                 200                 205

Gly Leu Gly Asn Ser Asp Leu Gln Glu Ser Arg Leu Gly Lys Leu Ser
    210                 215                 220

Ile Leu Arg Lys Lys Arg Leu Gln Pro Thr Asn Lys Ile Ile Phe Ser
225                 230                 235                 240

Val Gly Ser Thr Ile Tyr Thr Glu Asp Arg Ser Leu Leu Arg Ser Trp
                245                 250                 255

His Leu Pro Asn Val Phe His Leu Lys Gly Lys Ser Asn Phe Thr Gly
            260                 265                 270

Arg Cys Gly Thr Ile Val Ser Cys Glu Gly Tyr Val Ile Lys Lys Ile
        275                 280                 285

Thr Ile Ser Pro Gly Leu Tyr Gly Lys Val Glu Asn Leu Ala Ser Thr
    290                 295                 300

Met His Arg Glu Gly Phe Leu Ser Cys Lys Val Thr Asp Thr Leu Arg
305                 310                 315                 320
Gly Glu Arg Val Ser Phe Ala Val Cys Thr Tyr Val Pro Ala Thr Leu
                325                 330                 335

Cys Asp Gln Met Thr Gly Ile Leu Ala Thr Asp Val Ser Val Asp Asp
            340                 345                 350

Ala Gln Lys Leu Leu Val Gly Leu Asn Gln Arg Ile Val Val Asn Gly
        355                 360                 365

Arg Thr Gln Arg Asn Thr Asn Thr Met Gln Asn Tyr Leu Leu Pro Val
    370                 375                 380
```

-continued

```
Val Ala Gln Ala Phe Ser Arg Trp Ala Arg Glu His Arg Ala Asp Leu
385                 390                 395                 400

Asp Asp Glu Lys Glu Leu Gly Val Arg Glu Arg Thr Leu Thr Met Gly
            405                 410                 415

Cys Cys Trp Ala Phe Lys Thr Gln Lys Ile Thr Ser Ile Tyr Lys Lys
            420                 425                 430

Pro Gly Thr Gln Thr Ile Lys Lys Val Pro Ala Val Phe Asp Ser Phe
            435                 440                 445

Val Ile Pro Arg Leu Thr Ser His Gly Leu Asp Met Gly Phe Arg Arg
        450                 455                 460

Arg Leu Lys Leu Leu Leu Glu Pro Thr Val Lys Pro Ala Pro Ala Ile
465                 470                 475                 480

Thr Met Ala Asp Val Glu His Leu Arg Gly Leu Gln Gln Glu Ala Glu
                485                 490                 495

Glu Val Ala Ala Ala Glu Glu Ile Arg Glu Ala Leu Pro Pro Leu Leu
            500                 505                 510

Pro Glu Ile Glu Lys Glu Thr Val Glu Ala Glu Val Asp Leu Ile Met
            515                 520                 525

Gln Glu Ala Gly Ala Gly Ser Val Glu Thr Pro Arg Gly His Ile Arg
530                 535                 540

Val Thr Ser Tyr Pro Gly Glu Glu Lys Ile Gly Ser Tyr Ala Ile Leu
545                 550                 555                 560

Ser Pro Gln Ala Val Leu Asn Ser Glu Lys Leu Ala Cys Ile His Pro
            565                 570                 575

Leu Ala Glu Gln Val Leu Val Met Thr His Lys Gly Arg Ala Gly Arg
                580                 585                 590

Tyr Lys Val Glu Pro Tyr His Gly Lys Val Ile Val Pro Glu Gly Thr
            595                 600                 605

Ala Val Pro Val Gln Asp Phe Gln Ala Leu Ser Glu Ser Ala Thr Ile
        610                 615                 620

Val Phe Asn Glu Arg Glu Phe Val Asn Arg Tyr Leu His His Ile Ala
625                 630                 635                 640

Ile Asn Gly Gly Ala Leu Asn Thr Asp Glu Glu Tyr Tyr Lys Thr Val
                645                 650                 655

Lys Thr Gln Asp Thr Asp Ser Glu Tyr Val Phe Asp Ile Asp Ala Arg
            660                 665                 670

Lys Cys Val Lys Arg Glu Asp Ala Gly Pro Leu Cys Leu Thr Gly Asp
        675                 680                 685

Leu Val Asp Pro Pro Phe His Glu Phe Ala Tyr Glu Ser Leu Lys Thr
690                 695                 700

Arg Pro Ala Ala Pro His Lys Val Pro Thr Ile Gly Val Tyr Gly Val
705                 710                 715                 720

Pro Gly Ser Gly Lys Ser Gly Ile Ile Lys Ser Ala Val Thr Lys Lys
            725                 730                 735

Asp Leu Val Val Ser Ala Lys Lys Glu Asn Cys Ala Glu Ile Ile Arg
        740                 745                 750

Asp Val Arg Arg Met Arg Met Asp Val Ala Ala Arg Thr Val Asp
            755                 760                 765

Ser Val Leu Leu Asn Gly Val Lys His Pro Val Asn Thr Leu Tyr Ile
770                 775                 780

Asp Glu Ala Phe Ala Cys His Ala Gly Thr Leu Leu Ala Leu Ile Ala
785                 790                 795                 800

Ile Val Lys Pro Lys Lys Val Val Leu Cys Gly Asp Pro Lys Gln Cys
```

-continued

```
            805                 810                 815
Gly Phe Phe Asn Met Met Cys Leu Lys Val His Phe Asn His Asp Ile
            820                 825                 830
Cys Thr Glu Val Tyr His Lys Ser Ile Ser Arg Arg Cys Thr Gln Thr
            835                 840                 845
Val Thr Ala Ile Val Ser Thr Leu Phe Tyr Asp Lys Arg Met Lys Thr
            850                 855                 860
Val Asn Pro Cys Ala Asp Lys Ile Ile Ile Asp Thr Thr Gly Thr Thr
865                 870                 875                 880
Lys Pro His Lys Asp Asp Leu Ile Leu Thr Cys Phe Arg Gly Trp Val
                    885                 890                 895
Lys Gln Leu Gln Ile Asp Tyr Lys Asn His Glu Ile Met Thr Ala Ala
            900                 905                 910
Ala Ser Gln Gly Leu Thr Arg Lys Gly Val Tyr Ala Val Arg Tyr Lys
            915                 920                 925
Val Asn Glu Asn Pro Leu Tyr Ser Gln Thr Ser Glu His Val Asn Val
            930                 935                 940
Leu Leu Thr Arg Thr Glu Lys Arg Ile Val Trp Lys Thr Leu Ala Gly
945                 950                 955                 960
Asp Pro Trp Ile Lys Thr Leu Thr Ala Lys Tyr Pro Gly Asp Phe Thr
                    965                 970                 975
Ala Ser Leu Asp Asp Trp Gln Arg Glu His Asp Ala Ile Met Ala Arg
            980                 985                 990
Val Leu Asp Lys Pro Gln Thr Ala Asp Val Phe Gln Asn Lys Val Asn
            995                 1000                1005
Val Cys Trp Ala Lys Ala Leu Glu Pro Val Leu Ala Thr Ala Asn
    1010                1015                1020
Ile Val Leu Thr Arg Gln Gln Trp Glu Thr Leu His Pro Phe Lys
    1025                1030                1035
His Asp Arg Ala Tyr Ser Pro Glu Met Ala Leu Asn Phe Phe Cys
    1040                1045                1050
Thr Arg Phe Phe Gly Val Asp Leu Asp Ser Gly Leu Phe Ser Ala
    1055                1060                1065
Pro Thr Val Ala Leu Thr Tyr Arg Asp Gln His Trp Asp Asn Ser
    1070                1075                1080
Pro Gly Lys Asn Met Tyr Gly Leu Asn Arg Glu Val Ala Lys Glu
    1085                1090                1095
Leu Ser Arg Arg Tyr Pro Cys Ile Thr Lys Ala Val Asp Thr Gly
    1100                1105                1110
Arg Val Ala Asp Ile Arg Asn Asn Thr Ile Lys Asp Tyr Ser Pro
    1115                1120                1125
Thr Ile Asn Val Val Pro Leu Asn Arg Arg Leu Pro His Ser Leu
    1130                1135                1140
Ile Val Asp His Lys Gly Gln Gly Thr Thr Asp His Ser Gly Phe
    1145                1150                1155
Leu Ser Lys Met Lys Gly Lys Ser Val Leu Val Ile Gly Asp Pro
    1160                1165                1170
Ile Ser Ile Pro Gly Lys Lys Val Glu Ser Met Gly Pro Leu Pro
    1175                1180                1185
Thr Asn Thr Ile Arg Cys Asp Leu Asp Leu Gly Ile Pro Ser His
    1190                1195                1200
Val Gly Lys Tyr Asp Ile Ile Phe Val Asn Val Arg Thr Pro Tyr
    1205                1210                1215
```

-continued

Arg Asn His His Tyr Gln Gln Cys Glu Asp His Ala Ile His His
    1220                1225                1230

Ser Met Leu Thr Cys Lys Ala Val His His Leu Asn Thr Gly Gly
    1235                1240                1245

Thr Cys Val Ala Ile Gly Tyr Gly Leu Ala Asp Arg Ala Thr Glu
    1250                1255                1260

Asn Ile Ile Thr Ala Val Ala Arg Ser Phe Arg Phe Thr Arg Val
    1265                1270                1275

Cys Gln Pro Lys Asn Thr Ala Glu Asn Thr Glu Val Leu Phe Val
    1280                1285                1290

Phe Phe Gly Lys Asp Asn Gly Asn His Thr His Asp Gln Asp Arg
    1295                1300                1305

Leu Gly Val Val Leu Asp Asn Ile Tyr Gln Gly Ser Thr Arg Tyr
    1310                1315                1320

Glu Ala Gly Arg Ala Pro Ala Tyr Arg Val Ile Arg Gly Asp Ile
    1325                1330                1335

Ser Lys Ser Ala Asp Gln Ala Ile Val Asn Ala Ala Asn Ser Lys
    1340                1345                1350

Gly Gln Pro Gly Ser Gly Val Cys Gly Ala Leu Tyr Arg Lys Trp
    1355                1360                1365

Pro Ala Ala Phe Asp Arg Gln Pro Ile Ala Val Gly Thr Ala Arg
    1370                1375                1380

Leu Val Lys His Glu Pro Leu Ile Ile His Ala Val Gly Pro Asn
    1385                1390                1395

Phe Ser Lys Met Pro Glu Pro Glu Gly Asp Leu Lys Leu Ala Ala
    1400                1405                1410

Ala Tyr Met Ser Ile Ala Ser Ile Val Asn Ala Glu Arg Ile Thr
    1415                1420                1425

Lys Ile Ser Val Pro Leu Leu Ser Thr Gly Ile Tyr Ser Gly Gly
    1430                1435                1440

Lys Asp Arg Val Met Gln Ser Leu His His Leu Phe Thr Ala Phe
    1445                1450                1455

Asp Thr Thr Asp Ala Asp Val Thr Ile Tyr Cys Leu Asp Lys Gln
    1460                1465                1470

Trp Glu Thr Arg Ile Ile Glu Ala Ile His Arg Lys Glu Ser Val
    1475                1480                1485

Glu Ile Leu Asp Asp Asp Lys Pro Val Asp Ile Asp Leu Val Arg
    1490                1495                1500

Val His Pro Asn Ser Ser Leu Ala Gly Arg Pro Gly Tyr Ser Val
    1505                1510                1515

Asn Glu Gly Lys Leu Tyr Ser Tyr Leu Glu Gly Thr Arg Phe His
    1520                1525                1530

Gln Thr Ala Lys Asp Ile Ala Glu Ile His Ala Met Trp Pro Asn
    1535                1540                1545

Lys Ser Glu Ala Asn Glu Gln Ile Cys Leu Tyr Ile Leu Gly Glu
    1550                1555                1560

Ser Met Ser Ser Ile Arg Ser Lys Cys Pro Val Glu Glu Ser Glu
    1565                1570                1575

Ala Ser Ala Pro Pro His Thr Leu Pro Cys Leu Cys Asn Tyr Ala
    1580                1585                1590

Met Thr Ala Glu Arg Val Tyr Arg Leu Arg Ser Ala Lys Lys Glu
    1595                1600                1605

-continued

```
Gln Phe Ala Val Cys Ser Ser Phe Leu Leu Pro Lys Tyr Arg Ile
    1610                1615                1620

Thr Gly Val Gln Lys Leu Gln Cys Ser Lys Pro Val Leu Phe Ser
    1625                1630                1635

Gly Val Val Pro Pro Ala Val His Pro Arg Lys Tyr Ala Glu Ile
    1640                1645                1650

Ile Leu Glu Thr Pro Pro Pro Ala Thr Thr Thr Val Ile Cys
    1655                1660                1665

Glu Pro Thr Val Pro Glu Arg Ile Pro Ser Pro Val Ile Ser Arg
    1670                1675                1680

Ala Pro Ser Ala Glu Ser Leu Leu Ser Leu Gly Gly Val Ser Phe
    1685                1690                1695

Ser Ser Ser Ala Thr Arg Ser Ser Thr Ala Trp Ser Asp Tyr Asp
    1700                1705                1710

Arg Arg Phe Val Val Thr Ala Asp Val His Gln Ala Asn Thr Ser
    1715                1720                1725

Thr Trp Ser Ile Pro Ser Ala Pro Gly Leu Asp Val Gln Leu Pro
    1730                1735                1740

Ser Asp Val Thr Asp Ser His Trp Ser Ile Pro Ser Ala Ser Gly
    1745                1750                1755

Phe Glu Val Arg Thr Pro Ser Val Gln Asp Leu Thr Ala Glu Cys
    1760                1765                1770

Ala Lys Pro Arg Gly Leu Ala Glu Ile Met Gln Asp Phe Asn Thr
    1775                1780                1785

Ala Pro Phe Gln Phe Leu Ser Asp Tyr Arg Pro Val Pro Ala Pro
    1790                1795                1800

Arg Arg Arg Pro Ile Pro Ser Pro Arg Ser Thr Ala Ser Ala Pro
    1805                1810                1815

Pro Val Pro Lys Pro Arg Arg Thr Lys Tyr Gln Gln Pro Pro Gly
    1820                1825                1830

Val Ala Arg Ala Ile Ser Glu Ala Glu Leu Asp Glu Tyr Ile Arg
    1835                1840                1845

Gln His Ser Asn
    1850

<210> SEQ ID NO 3
<211> LENGTH: 614
<212> TYPE: PRT
<213> ORGANISM: Western equine encephalomyelitis virus - strain 71V-1658

<400> SEQUENCE: 3

Arg Tyr Glu Ala Gly Ala Tyr Ile Phe Ser Ser Glu Thr Gly Gln Gly
1               5                   10                  15

His Leu Gln Gln Lys Ser Val Arg Gln Cys Lys Leu Gln Glu Pro Ile
                20                  25                  30

Leu Asp Arg Ala Val His Glu Lys Tyr Tyr Ala Pro Arg Leu Asp Leu
            35                  40                  45

Glu Arg Glu Lys Met Leu Gln Lys Lys Leu Gln Leu Cys Ala Ser Glu
        50                  55                  60

Gly Asn Arg Ser Arg Tyr Gln Ser Arg Lys Val Glu Asn Met Lys Ala
65                  70                  75                  80

Ile Thr Ala Glu Arg Leu Ile Ser Gly Leu Gly Thr Tyr Leu Ser Ser
                85                  90                  95

Glu Val Asn Pro Val Glu Cys Tyr Arg Val Asn Tyr Pro Val Pro Ile
                100                 105                 110
```

-continued

```
Tyr Ser Ser Thr Val Ile Asn Arg Phe Thr Ser Ala Glu Val Ala Val
            115                 120                 125
Lys Thr Cys Asn Leu Val Ile Gln Glu Asn Tyr Pro Thr Val Ala Ser
        130                 135                 140
Tyr Cys Ile Thr Asp Glu Tyr Asp Ala Tyr Leu Asp Met Val Asp Gly
145                 150                 155                 160
Ala Ser Cys Cys Leu Asp Thr Ala Thr Phe Cys Pro Ala Lys Leu Arg
                165                 170                 175
Ser Tyr Pro Lys Lys His Ser Tyr Leu Gln Pro Glu Ile Arg Ser Ala
            180                 185                 190
Val Pro Ser Pro Ile Gln Asn Thr Leu Gln Asn Val Leu Ala Ala Ala
        195                 200                 205
Thr Lys Arg Asn Cys Asn Val Thr Gln Met Arg Glu Leu Pro Val Leu
    210                 215                 220
Asp Ser Ala Ala Phe Asn Val Asp Cys Phe Lys Lys Tyr Ala Cys Asn
225                 230                 235                 240
Asp Glu Tyr Trp Asp Thr Phe Arg Asp Asn Pro Ile Arg Leu Thr Thr
                245                 250                 255
Glu Asn Val Thr Gln Tyr Val Thr Lys Leu Lys Gly Pro Lys Ala Ala
            260                 265                 270
Ala Leu Phe Ala Asn Thr His Asn Leu Lys Pro Leu Gln Glu Ile Pro
        275                 280                 285
Met Asp Gln Phe Val Met Asp Leu Lys Arg Asp Val Lys Val Thr Pro
    290                 295                 300
Gly Thr Lys His Thr Glu Glu Arg Pro Lys Val Gln Val Ile Gln Ala
305                 310                 315                 320
Ala Asp Pro Leu Ala Thr Ala Tyr Leu Cys Gly Ile His Arg Glu Leu
                325                 330                 335
Val Arg Arg Leu Asn Ala Val Leu Leu Pro Asn Ile His Thr Leu Phe
            340                 345                 350
Asp Met Ser Ala Glu Asp Phe Asp Ala Ile Ile Ala Glu His Phe His
        355                 360                 365
His Gly Asp Pro Val Leu Glu Thr Asp Ile Ala Ser Phe Asp Lys Ser
    370                 375                 380
Glu Asp Asp Ala Ile Ala Ile Ser Ala Leu Met Ile Leu Glu Asp Leu
385                 390                 395                 400
Gly Val Asp Gln Pro Leu Leu Asp Leu Ile Glu Ala Ala Phe Gly Asn
                405                 410                 415
Ile Thr Ser Val His Leu Pro Thr Gly Thr Arg Phe Lys Phe Gly Ala
            420                 425                 430
Met Met Lys Ser Gly Met Phe Leu Thr Leu Phe Val Asn Thr Leu Val
        435                 440                 445
Asn Ile Met Ile Ala Ser Arg Val Leu Arg Glu Arg Leu Thr Thr Ser
    450                 455                 460
Ala Cys Ala Ala Ser Ile Gly Asp Asp Asn Ile Val His Gly Val Val
465                 470                 475                 480
Ser Asp Thr Leu Met Ala Glu Arg Cys Ala Thr Trp Leu Asn Met Glu
                485                 490                 495
Val Lys Ile Ile Asp Ala Val Ile Gly Ile Lys Ala Pro Tyr Phe Cys
            500                 505                 510
Gly Gly Phe Ile Leu Val Asp Gln Ile Thr Gly Thr Ala Cys Arg Val
        515                 520                 525
```

```
Ala Asp Pro Leu Lys Arg Leu Phe Lys Leu Gly Lys Pro Leu Pro Val
    530                 535                 540

Asp Asp Thr Gln Asp Cys Asp Arg Arg Arg Ala Leu His Asp Glu Ala
545                 550                 555                 560

Met Arg Trp Asn Arg Ile Gly Ile Thr Asp Glu Leu Val Lys Ala Val
                565                 570                 575

Glu Ser Arg Tyr Glu Ile Ile Leu Ala Gly Leu Ile Ile Thr Ser Leu
            580                 585                 590

Ser Thr Leu Ala Glu Ser Val Lys Asn Phe Lys Ser Ile Arg Gly Ser
        595                 600                 605

Pro Ile Thr Leu Tyr Gly
    610

<210> SEQ ID NO 4
<211> LENGTH: 1236
<212> TYPE: PRT
<213> ORGANISM: Western equine encephalomyelitis virus - strain 71V-1658

<400> SEQUENCE: 4

Met Phe Pro Tyr Pro Gln Leu Asn Phe Pro Val Tyr Pro Thr Asn
1               5                   10                  15

Pro Met Ala Tyr Arg Asp Pro Asn Pro Arg Arg Arg Trp Arg Pro
            20                  25                  30

Phe Arg Pro Pro Leu Ala Ala Gln Ile Glu Asp Leu Arg Arg Ser Ile
        35                  40                  45

Val Asn Leu Thr Phe Lys Gln Arg Ser Pro Asn Pro Pro Gly Pro
50                  55                  60

Pro Pro Lys Lys Lys Ser Ala Pro Lys Pro Lys Pro Thr Gln Pro
65                  70                  75                  80

Lys Lys Lys Lys Gln Gln Ala Lys Arg Thr Lys Arg Lys Pro Lys Pro
            85                  90                  95

Gly Lys Arg Gln Arg Met Cys Met Lys Leu Glu Ser Asp Lys Thr Phe
            100                 105                 110

Pro Ile Met Leu Asn Gly Gln Val Asn Gly Tyr Ala Cys Val Val Gly
            115                 120                 125

Gly Arg Leu Met Lys Pro Leu His Val Glu Gly Lys Ile Asp Asn Glu
    130                 135                 140

Gln Leu Ala Ala Val Lys Leu Lys Lys Ala Ser Met Tyr Asp Leu Glu
145                 150                 155                 160

Tyr Gly Asp Val Pro Gln Asn Met Lys Ser Asp Thr Leu Gln Tyr Thr
                165                 170                 175

Ser Asp Lys Pro Pro Gly Phe Tyr Asn Trp His His Gly Ala Val Gln
            180                 185                 190

Tyr Glu Asn Gly Arg Phe Thr Val Pro Arg Gly Val Gly Gly Lys Gly
            195                 200                 205

Asp Ser Gly Arg Pro Ile Leu Asp Asn Arg Gly Arg Val Val Ala Ile
    210                 215                 220

Val Leu Gly Gly Ala Asn Glu Gly Thr Arg Thr Ala Leu Ser Val Val
225                 230                 235                 240

Thr Trp Asn Gln Lys Gly Val Thr Ile Arg Asp Thr Pro Glu Gly Ser
                245                 250                 255

Glu Pro Trp Ser Leu Val Thr Ala Leu Cys Val Leu Ser Asn Val Thr
            260                 265                 270

Phe Pro Cys Asp Lys Pro Pro Val Cys Tyr Ser Leu Thr Pro Glu Arg
            275                 280                 285
```

```
Thr Leu Asp Val Leu Glu Glu Asn Val Asp Asn Pro Asn Tyr Asp Thr
    290                 295                 300

Leu Leu Glu Asn Val Leu Lys Cys Pro Ser Arg Arg Pro Lys Arg Ser
305                 310                 315                 320

Ile Thr Asp Asp Phe Thr Leu Thr Ser Pro Tyr Leu Gly Phe Cys Pro
                325                 330                 335

Tyr Cys Arg His Ser Thr Pro Cys Phe Ser Pro Ile Lys Ile Glu Asn
            340                 345                 350

Val Trp Asp Glu Ser Asp Asp Gly Ser Ile Arg Ile Gln Val Ser Ala
        355                 360                 365

Gln Phe Gly Tyr Asn Gln Ala Gly Thr Ala Asp Val Thr Lys Phe Arg
    370                 375                 380

Tyr Met Ser Phe Asp His Asp His Asp Ile Lys Glu Asp Ser Met Glu
385                 390                 395                 400

Lys Ile Ala Ile Ser Thr Ser Gly Pro Cys Arg Arg Leu Gly His Lys
                405                 410                 415

Gly Tyr Phe Leu Leu Ala Gln Cys Pro Pro Gly Asp Ser Val Thr Val
            420                 425                 430

Ser Ile Thr Ser Gly Ala Ser Glu Asn Ser Cys Thr Val Glu Lys Lys
        435                 440                 445

Ile Arg Arg Lys Phe Val Gly Arg Glu Glu Tyr Leu Phe Pro Pro Val
    450                 455                 460

His Gly Lys Leu Val Lys Cys His Val Tyr Asp His Leu Lys Glu Thr
465                 470                 475                 480

Ser Ala Gly Tyr Ile Thr Met His Arg Pro Gly Pro His Ala Tyr Lys
                485                 490                 495

Ser Tyr Leu Glu Glu Ala Ser Gly Glu Val Tyr Ile Lys Pro Pro Ser
            500                 505                 510

Gly Lys Asn Val Thr Tyr Glu Cys Lys Cys Gly Asp Tyr Ser Thr Gly
        515                 520                 525

Ile Val Ser Thr Arg Thr Lys Met Asn Gly Cys Thr Lys Ala Lys Gln
    530                 535                 540

Cys Ile Ala Tyr Lys Ser Asp Gln Thr Lys Trp Val Phe Asn Ser Pro
545                 550                 555                 560

Asp Leu Ile Arg His Thr Asp His Ser Val Gln Gly Lys Leu His Ile
                565                 570                 575

Pro Phe Arg Leu Thr Pro Thr Val Cys Pro Val Pro Leu Ala His Thr
            580                 585                 590

Pro Thr Val Thr Lys Trp Phe Lys Gly Ile Thr Leu His Leu Thr Ala
        595                 600                 605

Met Arg Pro Thr Leu Thr Thr Arg Lys Leu Gly Leu Arg Ala Asp
    610                 615                 620

Ala Thr Ala Glu Trp Ile Thr Gly Ser Thr Ser Arg Asn Phe Ser Val
625                 630                 635                 640

Gly Arg Glu Gly Leu Glu Tyr Val Trp Gly Asn His Glu Pro Val Arg
                645                 650                 655

Val Trp Ala Gln Glu Ser Ala Pro Gly Asp Pro His Gly Trp Pro His
            660                 665                 670

Glu Ile Ile Ile His Tyr Tyr His Arg His Pro Val Tyr Thr Val Ile
        675                 680                 685

Val Leu Cys Gly Val Ala Leu Ala Ile Leu Val Gly Thr Ala Ser Ser
    690                 695                 700
```

-continued

Ala Ala Cys Ile Ala Lys Ala Arg Arg Asp Cys Leu Thr Pro Tyr Ala
705                 710                 715                 720

Leu Ala Pro Asn Ala Thr Val Pro Thr Ala Leu Ala Val Leu Cys Cys
            725                 730                 735

Ile Arg Pro Thr Asn Ala Glu Thr Phe Gly Glu Thr Leu Asn His Leu
            740                 745                 750

Trp Phe Asn Asn Gln Pro Phe Leu Trp Ala Gln Leu Cys Ile Pro Leu
            755                 760                 765

Ala Ala Leu Val Ile Leu Phe Arg Cys Phe Ser Cys Cys Met Pro Phe
770                 775                 780

Leu Leu Val Ala Gly Val Cys Leu Gly Lys Val Asp Ala Phe Glu His
785                 790                 795                 800

Ala Thr Thr Val Pro Asn Val Pro Gly Ile Pro Tyr Lys Ala Leu Val
                805                 810                 815

Glu Arg Ala Gly Tyr Ala Pro Leu Asn Leu Glu Ile Thr Val Val Ser
            820                 825                 830

Ser Glu Leu Thr Pro Ser Thr Asn Lys Glu Tyr Val Thr Cys Lys Phe
            835                 840                 845

His Thr Val Ile Pro Ser Pro Gln Val Lys Cys Cys Gly Ser Leu Glu
    850                 855                 860

Cys Lys Ala Ser Ser Lys Ala Asp Tyr Thr Cys Arg Val Phe Gly Gly
865                 870                 875                 880

Val Tyr Pro Phe Met Trp Gly Gly Ala Gln Cys Phe Cys Asp Ser Glu
            885                 890                 895

Asn Thr Gln Leu Ser Glu Ala Tyr Val Glu Phe Ala Pro Asp Cys Thr
            900                 905                 910

Ile Asp His Ala Val Ala Leu Lys Val His Thr Ala Ala Leu Lys Val
    915                 920                 925

Gly Leu Arg Ile Val Tyr Gly Asn Thr Thr Ala His Leu Asp Thr Phe
    930                 935                 940

Val Asn Gly Val Thr Pro Gly Ser Ser Arg Asp Leu Lys Val Ile Ala
945                 950                 955                 960

Gly Pro Ile Ser Ala Ala Phe Ser Pro Phe Asp His Lys Val Val Ile
                965                 970                 975

Arg Lys Gly Leu Val Tyr Asn Tyr Asp Phe Pro Glu Tyr Gly Ala Met
            980                 985                 990

Lys Pro Gly Ala Phe Gly Asp Ile Gln Ala Ser Ser Leu Asp Ala Thr
    995                 1000                1005

Asp Ile Val Ala Arg Thr Asp Ile Arg Leu Leu Lys Pro Ser Val
    1010                1015                1020

Lys Asn Ile His Val Pro Tyr Thr Gln Ala Val Ser Gly Tyr Glu
    1025                1030                1035

Met Trp Lys Asn Asn Ser Gly Arg Pro Leu Gln Glu Thr Ala Pro
    1040                1045                1050

Phe Gly Cys Lys Ile Glu Val Glu Pro Leu Arg Ala Ser Asn Cys
    1055                1060                1065

Ala Tyr Gly His Ile Pro Ile Ser Ile Asp Ile Pro Asp Ala Ala
    1070                1075                1080

Phe Val Arg Ser Ser Glu Ser Pro Thr Ile Leu Glu Val Ser Cys
    1085                1090                1095

Thr Val Ala Asp Cys Ile Tyr Ser Ala Asp Phe Gly Gly Ser Leu
    1100                1105                1110

Thr Leu Gln Tyr Lys Ala Asp Arg Glu Gly His Cys Pro Val His

-continued

```
                    1115                1120                1125

Ser His Ser Thr Thr Ala Val Leu Lys Glu Ala Thr Thr His Val
        1130                1135                1140

Thr Ala Val Gly Ser Ile Thr Leu His Phe Ser Thr Ser Ser Pro
        1145                1150                1155

Gln Ala Asn Phe Ile Val Ser Leu Cys Gly Lys Lys Ser Thr Cys
        1160                1165                1170

Asn Ala Glu Cys Lys Pro Pro Ala Asp His Ile Ile Gly Glu Pro
        1175                1180                1185

His Lys Val Asp Gln Glu Phe Gln Ala Ala Val Ser Lys Thr Ser
        1190                1195                1200

Trp Asn Trp Leu Leu Ala Leu Phe Gly Gly Ala Ser Ser Leu Ile
        1205                1210                1215

Val Val Gly Leu Ile Val Leu Val Cys Ser Ser Met Leu Ile Asn
        1220                1225                1230

Thr Arg Arg
        1235

<210> SEQ ID NO 5
<211> LENGTH: 4150
<212> TYPE: DNA
<213> ORGANISM: Western equine encephalomyelitis virus - strain 71V-1658
<220> FEATURE:
<221> NAME/KEY: CDS
<222> LOCATION: (159)..(3869)
<223> OTHER INFORMATION: vector sequence 1-9; 5' SacI primer 9-20; 3'
      end of NS4 gene 16-1
      14; intragenic region 115-158; polyprotein (C-E3-E2-6K-E1) 159-38
      56; pcDW-XH7 nontranslated region 3857-4150

<400> SEQUENCE: 5
ggccctctag agctcatact ggcaggcctg atcatcacgt ctctgtccac gttagccgaa      60
agcgttaaga acttcaagag cataagaggg agcccaatca ccctctacgg ctgacctaaa    120
taggtgacgt agtagacacg cacctaccca ccggcaga atg ttt cca tac cct cag    176
                                            Met Phe Pro Tyr Pro Gln
                                              1               5 ctg aac ttt cca cca gtt tac cct aca aat ccg atg gct tac cga gat      224
Leu Asn Phe Pro Pro Val Tyr Pro Thr Asn Pro Met Ala Tyr Arg Asp
            10                  15                  20 cca aac cct cct agg cgc cgc tgg agg ccg ttt cgg ccc ccg ctg gct      272
Pro Asn Pro Pro Arg Arg Arg Trp Arg Pro Phe Arg Pro Pro Leu Ala
        25                  30                  35 gct caa atc gaa gat ctt agg agg tcg ata gtc aac ttg act ttc aaa      320
Ala Gln Ile Glu Asp Leu Arg Arg Ser Ile Val Asn Leu Thr Phe Lys
    40                  45                  50 caa cga tca cct aat ccg ccg cca ggt cca ccg cca aag aag aag aag      368
Gln Arg Ser Pro Asn Pro Pro Pro Gly Pro Pro Pro Lys Lys Lys Lys
55                  60                  65                  70 agt gct cct aag cca aaa cct act cag cct aaa aag aag aag cag caa      416
Ser Ala Pro Lys Pro Lys Pro Thr Gln Pro Lys Lys Lys Lys Gln Gln
            75                  80                  85 gcc aag agg acg aaa cgc aag cct aaa cca ggg aaa cga caa cgt atg      464
Ala Lys Arg Thr Lys Arg Lys Pro Lys Pro Gly Lys Arg Gln Arg Met
        90                  95                 100 tgt atg aag ttg gag tcg gac aag aca ttt ccg atc atg ctg aac ggc      512
Cys Met Lys Leu Glu Ser Asp Lys Thr Phe Pro Ile Met Leu Asn Gly
    105                 110                 115 caa gtg aat gga tat gcc tgc gtt gtc gga gga agg ctg atg aaa cca      560
Gln Val Asn Gly Tyr Ala Cys Val Val Gly Gly Arg Leu Met Lys Pro
```

-continued

```
              120                 125                 130
ctc cac gtt gaa gga aaa att gat aat gag caa tta gcg gcc gtg aaa    608
Leu His Val Glu Gly Lys Ile Asp Asn Glu Gln Leu Ala Ala Val Lys
135                 140                 145                 150 ttg aag aag gct agc atg tac gac ttg gag tac ggc gac gtt ccc cag    656
Leu Lys Lys Ala Ser Met Tyr Asp Leu Glu Tyr Gly Asp Val Pro Gln
                155                 160                 165 aac atg aaa tca gac acg ctg cag tac acc agc gac aaa cca ccg ggc    704
Asn Met Lys Ser Asp Thr Leu Gln Tyr Thr Ser Asp Lys Pro Pro Gly
            170                 175                 180 ttc tac aac tgg cac cac ggc gca gtc cag tat gag aat ggg aga ttt    752
Phe Tyr Asn Trp His His Gly Ala Val Gln Tyr Glu Asn Gly Arg Phe
        185                 190                 195 acc gta ccg aga gga gtg ggc ggg aaa ggc gac agc gga aga ccg atc    800
Thr Val Pro Arg Gly Val Gly Gly Lys Gly Asp Ser Gly Arg Pro Ile
    200                 205                 210 ctg gac aac aga ggc aga gtt gtg gct att gtt cta gga ggt gca aat    848
Leu Asp Asn Arg Gly Arg Val Val Ala Ile Val Leu Gly Gly Ala Asn
215                 220                 225                 230 gag ggc acg cgt acg gcg ctt tca gtg gtc act tgg aac cag aaa ggg    896
Glu Gly Thr Arg Thr Ala Leu Ser Val Val Thr Trp Asn Gln Lys Gly
                235                 240                 245 gtg acc att agg gat acc ccc gaa ggt tct gaa ccg tgg tca cta gtt    944
Val Thr Ile Arg Asp Thr Pro Glu Gly Ser Glu Pro Trp Ser Leu Val
            250                 255                 260 aca gcg cta tgc gtg ctt tcg aat gtc acg ttc cca tgc gac aaa cca    992
Thr Ala Leu Cys Val Leu Ser Asn Val Thr Phe Pro Cys Asp Lys Pro
        265                 270                 275 ccc gtg tgc tat tca ctg acg cca gaa cga aca ctc gac gtg ctc gaa    1040
Pro Val Cys Tyr Ser Leu Thr Pro Glu Arg Thr Leu Asp Val Leu Glu
    280                 285                 290 gag aac gtc gac aat cca aat tac gac acg ctg ctg gag aac gtc ttg    1088
Glu Asn Val Asp Asn Pro Asn Tyr Asp Thr Leu Leu Glu Asn Val Leu
295                 300                 305                 310 aaa tgt cca tca cgc cgg ccc aaa cga agc att acc gat gac ttc aca    1136
Lys Cys Pro Ser Arg Arg Pro Lys Arg Ser Ile Thr Asp Asp Phe Thr
                315                 320                 325 ctg acc agt ccc tac ctg ggg ttc tgc ccg tat tgc aga cac tca acg    1184
Leu Thr Ser Pro Tyr Leu Gly Phe Cys Pro Tyr Cys Arg His Ser Thr
            330                 335                 340 ccg tgt ttc agc cca ata aaa att gag aac gtg tgg gac gaa tct gat    1232
Pro Cys Phe Ser Pro Ile Lys Ile Glu Asn Val Trp Asp Glu Ser Asp
        345                 350                 355 gat gga tcg att aga atc cag gtc tcg gca caa ttc ggc tac aat cag    1280
Asp Gly Ser Ile Arg Ile Gln Val Ser Ala Gln Phe Gly Tyr Asn Gln
    360                 365                 370 gca ggc act gcg gat gtc acc aaa ttc cgt tac atg tct ttc gac cac    1328
Ala Gly Thr Ala Asp Val Thr Lys Phe Arg Tyr Met Ser Phe Asp His
375                 380                 385                 390 gac cat gac atc aag gaa gac agt atg gag aaa ata gct atc agc aca    1376
Asp His Asp Ile Lys Glu Asp Ser Met Glu Lys Ile Ala Ile Ser Thr
                395                 400                 405 tct gga ccc tgc cgt cgt ctt ggc cac aaa ggg tac ttc ctg tta gct    1424
Ser Gly Pro Cys Arg Arg Leu Gly His Lys Gly Tyr Phe Leu Leu Ala
            410                 415                 420 caa tgt cct cca ggt gac agt gta acc gtc agt atc acg agc gga gca    1472
Gln Cys Pro Pro Gly Asp Ser Val Thr Val Ser Ile Thr Ser Gly Ala
        425                 430                 435 tct gag aat tca tgc acc gtg gag aaa aag atc agg agg aag ttt gtc    1520
```

-continued

```
Ser Glu Asn Ser Cys Thr Val Glu Lys Lys Ile Arg Arg Lys Phe Val
    440                 445                 450 ggt aga gag gag tac ttg ttc cca ccc gtc cat gga aag ctg gta aag      1568
Gly Arg Glu Glu Tyr Leu Phe Pro Pro Val His Gly Lys Leu Val Lys
455                 460                 465                 470 tgc cac gtt tac gat cac ttg aag gag acg tct gcc ggg tac ata acc      1616
Cys His Val Tyr Asp His Leu Lys Glu Thr Ser Ala Gly Tyr Ile Thr
                475                 480                 485 atg cac agg cca ggc cca cac gcg tat aag tcc tat ctg gag gaa gcg      1664
Met His Arg Pro Gly Pro His Ala Tyr Lys Ser Tyr Leu Glu Glu Ala
            490                 495                 500 tca ggc gaa gtg tac att aaa cca cct tct ggc aag aac gtc acc tac      1712
Ser Gly Glu Val Tyr Ile Lys Pro Pro Ser Gly Lys Asn Val Thr Tyr
        505                 510                 515 gaa tgt aag tgt ggc gac tac agc aca ggt atc gtg agc acg cga acg      1760
Glu Cys Lys Cys Gly Asp Tyr Ser Thr Gly Ile Val Ser Thr Arg Thr
    520                 525                 530 aag atg aac ggc tgc act aaa gca aaa cag tgc att gcc tac aag agc      1808
Lys Met Asn Gly Cys Thr Lys Ala Lys Gln Cys Ile Ala Tyr Lys Ser
535                 540                 545                 550 gac caa acg aaa tgg gtc ttc aac tcg ccg gat ctt att agg cac aca      1856
Asp Gln Thr Lys Trp Val Phe Asn Ser Pro Asp Leu Ile Arg His Thr
                555                 560                 565 gac cac tca gtg caa ggt aaa ttg cac att cca ttc cgc ttg aca ccg      1904
Asp His Ser Val Gln Gly Lys Leu His Ile Pro Phe Arg Leu Thr Pro
            570                 575                 580 aca gtc tgc ccg gtt ccg tta gct cac acg cct aca gtc acg aag tgg      1952
Thr Val Cys Pro Val Pro Leu Ala His Thr Pro Thr Val Thr Lys Trp
        585                 590                 595 ttc aaa ggc atc acc ctc cac ctg act gca atg cga cca aca ttg ctg      2000
Phe Lys Gly Ile Thr Leu His Leu Thr Ala Met Arg Pro Thr Leu Leu
    600                 605                 610 aca acg aga aaa ttg ggg ctg cga gca gac gca aca gca gaa tgg att      2048
Thr Thr Arg Lys Leu Gly Leu Arg Ala Asp Ala Thr Ala Glu Trp Ile
615                 620                 625                 630 aca ggg tct aca tcc agg aat ttt tct gtg ggg cga gaa ggg ctg gag      2096
Thr Gly Ser Thr Ser Arg Asn Phe Ser Val Gly Arg Glu Gly Leu Glu
                635                 640                 645 tac gta tgg ggt aac cat gaa cca gtc aga gtc tgg gcc cag gag tcg      2144
Tyr Val Trp Gly Asn His Glu Pro Val Arg Val Trp Ala Gln Glu Ser
            650                 655                 660 gca cca ggc gac cca cat gga tgg ccg cat gag atc atc atc cac tat      2192
Ala Pro Gly Asp Pro His Gly Trp Pro His Glu Ile Ile Ile His Tyr
        665                 670                 675 tat cat cgg cat cca gtc tac act gtc att gtg ctg tgt ggt gtc gct      2240
Tyr His Arg His Pro Val Tyr Thr Val Ile Val Leu Cys Gly Val Ala
    680                 685                 690 ctt gct atc ctg gta ggc act gca tca tca gca gct tgc atc gcc aaa      2288
Leu Ala Ile Leu Val Gly Thr Ala Ser Ser Ala Ala Cys Ile Ala Lys
695                 700                 705                 710 gca aga aga gac tgc ctg acg cca tac gcg ctt gca ccg aac gca acg      2336
Ala Arg Arg Asp Cys Leu Thr Pro Tyr Ala Leu Ala Pro Asn Ala Thr
                715                 720                 725 gta ccc aca gca tta gcg gtt ttg tgc tgc att cgg cca acc aac gct      2384
Val Pro Thr Ala Leu Ala Val Leu Cys Cys Ile Arg Pro Thr Asn Ala
            730                 735                 740 gaa aca ttt gga gaa act ttg aac cat ctg tgg ttt aac aac caa ccg      2432
Glu Thr Phe Gly Glu Thr Leu Asn His Leu Trp Phe Asn Asn Gln Pro
    745                 750                 755
```

-continued

| | |
|---|---|
| ttt ctc tgg gca cag ttg tgc att cct ctg gca gcg ctt gtt att ctg<br>Phe Leu Trp Ala Gln Leu Cys Ile Pro Leu Ala Ala Leu Val Ile Leu<br>760                           765                     770 | 2480 |
| ttc cgc tgc ttt tca tgc tgc atg cct ttt tta ttg gtt gca ggc gtc<br>Phe Arg Cys Phe Ser Cys Cys Met Pro Phe Leu Leu Val Ala Gly Val<br>775                           780                     785                     790 | 2528 |
| tgc ctg ggg aag gta gac gcc ttc gaa cat gcg acc act gtg cca aat<br>Cys Leu Gly Lys Val Asp Ala Phe Glu His Ala Thr Thr Val Pro Asn<br>                     795                     800                     805 | 2576 |
| gtt ccg ggg atc ccg tat aag gcg ttg gtc gaa cgc gca ggt tac gcg<br>Val Pro Gly Ile Pro Tyr Lys Ala Leu Val Glu Arg Ala Gly Tyr Ala<br>810                           815                     820 | 2624 |
| cca ctt aac ctg gag atc acg gtc gtc tca tcg gaa tta aca cct tca<br>Pro Leu Asn Leu Glu Ile Thr Val Val Ser Ser Glu Leu Thr Pro Ser<br>                     825                     830                     835 | 2672 |
| act aac aag gag tac gtg acc tgc aaa ttc cac aca gtc att cct tca<br>Thr Asn Lys Glu Tyr Val Thr Cys Lys Phe His Thr Val Ile Pro Ser<br>840                           845                     850 | 2720 |
| cca caa gtt aaa tgc tgc ggg tcc ctc gag tgc aag gca tcc tca aag<br>Pro Gln Val Lys Cys Cys Gly Ser Leu Glu Cys Lys Ala Ser Ser Lys<br>855                           860                     865                     870 | 2768 |
| gcg gat tac aca tgc cgc gtt ttt ggc ggt gtg tac cct ttc atg tgg<br>Ala Asp Tyr Thr Cys Arg Val Phe Gly Gly Val Tyr Pro Phe Met Trp<br>                     875                     880                     885 | 2816 |
| gga ggc gca caa tgc ttc tgt gac agt gag aac aca caa ctg agt gag<br>Gly Gly Ala Gln Cys Phe Cys Asp Ser Glu Asn Thr Gln Leu Ser Glu<br>                     890                     895                     900 | 2864 |
| gcg tac gtc gag ttc gct cca gac tgc act ata gat cac gca gtc gca<br>Ala Tyr Val Glu Phe Ala Pro Asp Cys Thr Ile Asp His Ala Val Ala<br>905                           910                     915 | 2912 |
| cta aaa gtt cac aca gct gct ctg aaa gtc ggc ctg cgt ata gta tac<br>Leu Lys Val His Thr Ala Ala Leu Lys Val Gly Leu Arg Ile Val Tyr<br>920                           925                     930 | 2960 |
| ggc aac acc acc gcg cac ctg gat acg ttt gtc aat ggc gtc acg cca<br>Gly Asn Thr Thr Ala His Leu Asp Thr Phe Val Asn Gly Val Thr Pro<br>935                           940                     945                     950 | 3008 |
| ggt tcc tca cgg gac ctg aag gtc ata gca ggg ccg ata tca gcc gct<br>Gly Ser Ser Arg Asp Leu Lys Val Ile Ala Gly Pro Ile Ser Ala Ala<br>                     955                     960                     965 | 3056 |
| ttt tca ccc ttt gac cat aag gtc gtc atc aga aag ggg ctt gtt tac<br>Phe Ser Pro Phe Asp His Lys Val Val Ile Arg Lys Gly Leu Val Tyr<br>970                           975                     980 | 3104 |
| aac tac gac ttc cct gag tat gga gct atg aaa cca gga gcg ttc ggc<br>Asn Tyr Asp Phe Pro Glu Tyr Gly Ala Met Lys Pro Gly Ala Phe Gly<br>                     985                     990                     995 | 3152 |
| gat att caa gca tcc tcg ctt    gat gct aca gac ata    gta gcc cgc<br>Asp Ile Gln Ala Ser Ser Leu    Asp Ala Thr Asp Ile    Val Ala Arg<br>        1000                     1005                      1010 | 3197 |
| act gac ata cgg ctg ctg aag    cct tct gtc aag aac    atc cac gtc<br>Thr Asp Ile Arg Leu Leu Lys    Pro Ser Val Lys Asn    Ile His Val<br>1015                     1020                      1025 | 3242 |
| ccc tac acc caa gca gta tca    ggg tat gaa atg tgg    aag aac aac<br>Pro Tyr Thr Gln Ala Val Ser    Gly Tyr Glu Met Trp    Lys Asn Asn<br>        1030                     1035                      1040 | 3287 |
| tca gga cga ccc ctg caa gaa    aca gca cca ttt gga    tgt aaa att<br>Ser Gly Arg Pro Leu Gln Glu    Thr Ala Pro Phe Gly    Cys Lys Ile<br>1045                     1050                      1055 | 3332 |
| gaa gtg gag cct ctg cga gcg    tct aac tgt gct tac    ggg cac atc<br>Glu Val Glu Pro Leu Arg Ala    Ser Asn Cys Ala Tyr    Gly His Ile<br>        1060                     1065                      1070 | 3377 |

```
cct atc tcg att gac atc cct gat gca gct ttt gtg aga tca tca      3422
Pro Ile Ser Ile Asp Ile Pro Asp Ala Ala Phe Val Arg Ser Ser
    1075                1080                1085 gaa tca cca aca att tta gaa gtt agc tgc aca gta gca gac tgc      3467
Glu Ser Pro Thr Ile Leu Glu Val Ser Cys Thr Val Ala Asp Cys
1090                1095                1100 att tat tct gca gac ttt ggt ggt tct cta aca tta cag tac aaa      3512
Ile Tyr Ser Ala Asp Phe Gly Gly Ser Leu Thr Leu Gln Tyr Lys
    1105                1110                1115 gct gac agg gag gga cat tgt cca gtt cac tcc cac tcc acg aca      3557
Ala Asp Arg Glu Gly His Cys Pro Val His Ser His Ser Thr Thr
1120                1125                1130 gct gtt ttg aag gaa gcg acc aca cat gtg act gcc gta ggc agc      3602
Ala Val Leu Lys Glu Ala Thr Thr His Val Thr Ala Val Gly Ser
    1135                1140                1145 ata aca cta cat ttt agc aca tcg agc cca caa gca aat ttt ata      3647
Ile Thr Leu His Phe Ser Thr Ser Ser Pro Gln Ala Asn Phe Ile
1150                1155                1160 gtt tcg cta tgc ggc aag aag tcc acc tgc aat gct gaa tgt aaa      3692
Val Ser Leu Cys Gly Lys Lys Ser Thr Cys Asn Ala Glu Cys Lys
    1165                1170                1175 cca ccg gcc gac cac ata att gga gaa cca cat aaa gtc gac caa      3737
Pro Pro Ala Asp His Ile Ile Gly Glu Pro His Lys Val Asp Gln
1180                1185                1190 gaa ttc cag gcg gca gtt tcc aaa aca tct tgg aac tgg ctg ctt      3782
Glu Phe Gln Ala Ala Val Ser Lys Thr Ser Trp Asn Trp Leu Leu
    1195                1200                1205 gca ctg ttt ggg gga gca tca tcc ctc att gtt gta gga ctt ata      3827
Ala Leu Phe Gly Gly Ala Ser Ser Leu Ile Val Val Gly Leu Ile
1210                1215                1220 gtg ttg gtc tgc agc tct atg ctt ata aac aca cgt aga tga          3869
Val Leu Val Cys Ser Ser Met Leu Ile Asn Thr Arg Arg
    1225                1230                1235 ctgagcgcgg acactgacat agcggtaaaa ctcgatgtac ttccgaggaa gcgtggtgca  3929
taatgccacg cgccgcttga cactaaaact cgatgtattt ccgaggaagc acagtgcata  3989
atgctgtgca gtgtcacatt aatcgtatat cacactacat attaacaaca ctatatcact  4049
tttatgagac tcactatggg tctctaatat acactacaca tattttactt aaaaacacta  4109
tacacacttt ataaattctc tcataatttc actttaggtt t                     4150

<210> SEQ ID NO 6
<211> LENGTH: 1236
<212> TYPE: PRT
<213> ORGANISM: Western equine encephalomyelitis virus - strain 71V-1658

<400> SEQUENCE: 6

Met Phe Pro Tyr Pro Gln Leu Asn Phe Pro Pro Val Tyr Pro Thr Asn
1               5                   10                  15

Pro Met Ala Tyr Arg Asp Pro Asn Pro Pro Arg Arg Arg Trp Arg Pro
            20                  25                  30

Phe Arg Pro Pro Leu Ala Ala Gln Ile Glu Asp Leu Arg Arg Ser Ile
        35                  40                  45

Val Asn Leu Thr Phe Lys Gln Arg Ser Pro Asn Pro Pro Gly Pro
    50                  55                  60

Pro Pro Lys Lys Lys Lys Ser Ala Pro Lys Pro Lys Pro Thr Gln Pro
65                  70                  75                  80

Lys Lys Lys Lys Gln Gln Ala Lys Arg Thr Lys Arg Lys Pro Lys Pro
```

-continued

```
                    85                  90                  95
Gly Lys Arg Gln Arg Met Cys Met Lys Leu Glu Ser Asp Lys Thr Phe
                100                 105                 110
Pro Ile Met Leu Asn Gly Gln Val Asn Gly Tyr Ala Cys Val Val Gly
            115                 120                 125
Gly Arg Leu Met Lys Pro Leu His Val Glu Gly Lys Ile Asp Asn Glu
        130                 135                 140
Gln Leu Ala Ala Val Lys Leu Lys Ala Ser Met Tyr Asp Leu Glu
145                 150                 155                 160
Tyr Gly Asp Val Pro Gln Asn Met Lys Ser Asp Thr Leu Gln Tyr Thr
                165                 170                 175
Ser Asp Lys Pro Pro Gly Phe Tyr Asn Trp His His Gly Ala Val Gln
                180                 185                 190
Tyr Glu Asn Gly Arg Phe Thr Val Pro Arg Gly Val Gly Lys Gly
            195                 200                 205
Asp Ser Gly Arg Pro Ile Leu Asp Asn Arg Gly Arg Val Val Ala Ile
        210                 215                 220
Val Leu Gly Gly Ala Asn Glu Gly Thr Arg Thr Ala Leu Ser Val Val
225                 230                 235                 240
Thr Trp Asn Gln Lys Gly Val Thr Ile Arg Asp Thr Pro Glu Gly Ser
                245                 250                 255
Glu Pro Trp Ser Leu Val Thr Ala Leu Cys Val Leu Ser Asn Val Thr
                260                 265                 270
Phe Pro Cys Asp Lys Pro Val Cys Tyr Ser Leu Thr Pro Glu Arg
            275                 280                 285
Thr Leu Asp Val Leu Glu Glu Asn Val Asp Asn Pro Asn Tyr Asp Thr
        290                 295                 300
Leu Leu Glu Asn Val Leu Lys Cys Pro Ser Arg Arg Pro Lys Arg Ser
305                 310                 315                 320
Ile Thr Asp Asp Phe Thr Leu Thr Ser Pro Tyr Leu Gly Phe Cys Pro
                325                 330                 335
Tyr Cys Arg His Ser Thr Pro Cys Phe Ser Pro Ile Lys Ile Glu Asn
                340                 345                 350
Val Trp Asp Glu Ser Asp Asp Gly Ser Ile Arg Ile Gln Val Ser Ala
            355                 360                 365
Gln Phe Gly Tyr Asn Gln Ala Gly Thr Ala Asp Val Thr Lys Phe Arg
        370                 375                 380
Tyr Met Ser Phe Asp His Asp His Asp Ile Lys Glu Asp Ser Met Glu
385                 390                 395                 400
Lys Ile Ala Ile Ser Thr Ser Gly Pro Cys Arg Arg Leu Gly His Lys
                405                 410                 415
Gly Tyr Phe Leu Leu Ala Gln Cys Pro Pro Gly Asp Ser Val Thr Val
                420                 425                 430
Ser Ile Thr Ser Gly Ala Ser Glu Asn Ser Cys Thr Val Glu Lys Lys
            435                 440                 445
Ile Arg Arg Lys Phe Val Gly Arg Glu Glu Tyr Leu Phe Pro Pro Val
        450                 455                 460
His Gly Lys Leu Val Lys Cys His Val Tyr Asp His Leu Lys Glu Thr
465                 470                 475                 480
Ser Ala Gly Tyr Ile Thr Met His Arg Pro Gly Pro His Ala Tyr Lys
                485                 490                 495
Ser Tyr Leu Glu Glu Ala Ser Gly Glu Val Tyr Ile Lys Pro Pro Ser
                500                 505                 510
```

-continued

```
Gly Lys Asn Val Thr Tyr Glu Cys Lys Cys Gly Asp Tyr Ser Thr Gly
            515                 520                 525
Ile Val Ser Thr Arg Thr Lys Met Asn Gly Cys Thr Lys Ala Lys Gln
        530                 535                 540
Cys Ile Ala Tyr Lys Ser Asp Gln Thr Lys Trp Val Phe Asn Ser Pro
545                 550                 555                 560
Asp Leu Ile Arg His Thr Asp His Ser Val Gln Gly Lys Leu His Ile
                565                 570                 575
Pro Phe Arg Leu Thr Pro Thr Val Cys Pro Val Pro Leu Ala His Thr
            580                 585                 590
Pro Thr Val Thr Lys Trp Phe Lys Gly Ile Thr Leu His Leu Thr Ala
        595                 600                 605
Met Arg Pro Thr Leu Leu Thr Arg Lys Leu Gly Leu Arg Ala Asp
610                 615                 620
Ala Thr Ala Glu Trp Ile Thr Gly Ser Thr Ser Arg Asn Phe Ser Val
625                 630                 635                 640
Gly Arg Glu Gly Leu Glu Tyr Val Trp Gly Asn His Glu Pro Val Arg
                645                 650                 655
Val Trp Ala Gln Glu Ser Ala Pro Gly Asp Pro His Gly Trp Pro His
            660                 665                 670
Glu Ile Ile Ile His Tyr Tyr His Arg His Pro Val Tyr Thr Val Ile
        675                 680                 685
Val Leu Cys Gly Val Ala Leu Ala Ile Leu Val Gly Thr Ala Ser Ser
        690                 695                 700
Ala Ala Cys Ile Ala Lys Ala Arg Arg Asp Cys Leu Thr Pro Tyr Ala
705                 710                 715                 720
Leu Ala Pro Asn Ala Thr Val Pro Thr Ala Leu Ala Val Leu Cys Cys
                725                 730                 735
Ile Arg Pro Thr Asn Ala Glu Thr Phe Gly Glu Thr Leu Asn His Leu
            740                 745                 750
Trp Phe Asn Asn Gln Pro Phe Leu Trp Ala Gln Leu Cys Ile Pro Leu
        755                 760                 765
Ala Ala Leu Val Ile Leu Phe Arg Cys Phe Ser Cys Cys Met Pro Phe
770                 775                 780
Leu Leu Val Ala Gly Val Cys Leu Gly Lys Val Asp Ala Phe Glu His
785                 790                 795                 800
Ala Thr Thr Val Pro Asn Val Pro Gly Ile Pro Tyr Lys Ala Leu Val
                805                 810                 815
Glu Arg Ala Gly Tyr Ala Pro Leu Asn Leu Glu Ile Thr Val Val Ser
            820                 825                 830
Ser Glu Leu Thr Pro Ser Thr Asn Lys Glu Tyr Val Thr Cys Lys Phe
        835                 840                 845
His Thr Val Ile Pro Ser Pro Gln Val Lys Cys Cys Gly Ser Leu Glu
        850                 855                 860
Cys Lys Ala Ser Ser Lys Ala Asp Tyr Thr Cys Arg Val Phe Gly Gly
865                 870                 875                 880
Val Tyr Pro Phe Met Trp Gly Gly Ala Gln Cys Phe Cys Asp Ser Glu
                885                 890                 895
Asn Thr Gln Leu Ser Glu Ala Tyr Val Glu Phe Ala Pro Asp Cys Thr
            900                 905                 910
Ile Asp His Ala Val Ala Leu Lys Val His Thr Ala Ala Leu Lys Val
        915                 920                 925
```

```
Gly Leu Arg Ile Val Tyr Gly Asn Thr Thr Ala His Leu Asp Thr Phe
    930                 935                 940

Val Asn Gly Val Thr Pro Gly Ser Ser Arg Asp Leu Lys Val Ile Ala
945                 950                 955                 960

Gly Pro Ile Ser Ala Ala Phe Ser Pro Phe Asp His Lys Val Val Ile
                965                 970                 975

Arg Lys Gly Leu Val Tyr Asn Tyr Asp Phe Pro Glu Tyr Gly Ala Met
            980                 985                 990

Lys Pro Gly Ala Phe Gly Asp Ile  Gln Ala Ser Ser Leu  Asp Ala Thr
        995                 1000                1005

Asp Ile  Val Ala Arg Thr Asp  Ile Arg Leu Leu Lys  Pro Ser Val
    1010                1015                1020

Lys Asn  Ile His Val Pro Tyr  Thr Gln Ala Val Ser  Gly Tyr Glu
    1025                1030                1035

Met Trp  Lys Asn Asn Ser Gly  Arg Pro Leu Gln Glu  Thr Ala Pro
    1040                1045                1050

Phe Gly  Cys Lys Ile Glu Val  Glu Pro Leu Arg Ala  Ser Asn Cys
    1055                1060                1065

Ala Tyr  Gly His Ile Pro Ile  Ser Ile Asp Ile Pro  Asp Ala Ala
    1070                1075                1080

Phe Val  Arg Ser Ser Glu Ser  Pro Thr Ile Leu Glu  Val Ser Cys
    1085                1090                1095

Thr Val  Ala Asp Cys Ile Tyr  Ser Ala Asp Phe Gly  Gly Ser Leu
    1100                1105                1110

Thr Leu  Gln Tyr Lys Ala Asp  Arg Glu Gly His Cys  Pro Val His
    1115                1120                1125

Ser His  Ser Thr Thr Ala Val  Leu Lys Glu Ala Thr  Thr His Val
    1130                1135                1140

Thr Ala  Val Gly Ser Ile Thr  Leu His Phe Ser Thr  Ser Ser Pro
    1145                1150                1155

Gln Ala  Asn Phe Ile Val Ser  Leu Cys Gly Lys Lys  Ser Thr Cys
    1160                1165                1170

Asn Ala  Glu Cys Lys Pro Pro  Ala Asp His Ile Ile  Gly Glu Pro
    1175                1180                1185

His Lys  Val Asp Gln Glu Phe  Gln Ala Ala Val Ser  Lys Thr Ser
    1190                1195                1200

Trp Asn  Trp Leu Leu Ala Leu  Phe Gly Gly Ala Ser  Ser Leu Ile
    1205                1210                1215

Val Val  Gly Leu Ile Val Leu  Val Cys Ser Ser Met  Leu Ile Asn
    1220                1225                1230

Thr Arg  Arg
    1235

<210> SEQ ID NO 7
<211> LENGTH: 4395
<212> TYPE: DNA
<213> ORGANISM: Western equine encephalomyelitis virus - STRAIN 71v-1658
<220> FEATURE:
<221> NAME/KEY: CMV promoter
<222> LOCATION: (1)..(1260)
<223> OTHER INFORMATION: Pvax vector sequence: 1-196; CMV promoter:
      1-115; CMV putative tr
         anscriptional start site: 125; T7 promoter: 48-167; pVAX multiclo
         ning region: 168-196; polypeptide (C-E3-E2-6K-E1): 214-4065; pcDW
         -HX45 nontranslated region: 4066-4348; pcDW-HX45 vector sequence:
         4349-4385; pVAX vector sequence: 4386

<400> SEQUENCE: 7
```

-continued

```
accaaaatca acgggacttt ccaaaatgtc gtaacaactc cgccccattg acgcaaatgg      60
gcggtaggcg tgtacggtgg gaggtcatat ataagcagag tctctctggc taactagaga     120
acccactgct tactggctta tcgaaattaa tacgactcac tatagggaga cccaagctgg     180
ctagcgttta aacttaagct tggtaccgag ctcatactgg caggcctgat catcacgtct     240
ctgtccacgt tagccgaaag cgttaagaac ttcaagagca taagagggag cccaatcacc     300
ctctacggct gacctaaata ggtgacgtag tagacacgca cctacccacc gccagaatgt     360
ttccataccc tcagctgaac tttccaccag tttaccctac aaatccgatg cttaccgag      420
atccaaaccc tcctaggcgc cgctggaggc cgtttcggcc cccgctggct gctcaaatcg     480
aagatcttag gaggtcgata gtcaacttga ctttcaaaca acgatcacct aatccgccgc     540
caggtccacc gccaaagaag aagaagagtg ctcctaagcc aaaacctact cagcctaaaa     600
agaagaagca gcaagccaag aggacgaaac gcaagcctaa accagggaaa cgacaacgta     660
tgtgtatgaa gttggagtcg acaagacat ttccgatcat gctgaacggc caagtgaatg      720
gatatgcctg cgttgtcgga ggaaggctga tgaaaccact ccacgttgaa ggaaaaattg     780
ataatgagca attagcggcc gtgaaattga agaaggctag catgtacgac ttggagtacg     840
gcgacgttcc ccagaacatg aaatcagaca cgctgcagta caccagcgac aaaccaccgg     900
gcttctacaa ctggcaccac ggcgcagtcc agtatgagaa tgggagattt accgtaccga     960
gaggagtggg cggaaaggc gacagcggaa gaccgatcct ggacaacaga ggcagagttg     1020
tggctattgt tctaggaggt gcaaatgagg gcacgcgtac ggcgctttca gtggtcactt     1080
ggaaccagaa aggggtgacc attagggata cccccgaagg ttctgaaccg tggtcactag     1140
ttacagcgct atgcgtgctt tcgaatgtca cgttcccatg cgacaaacca cccgtgtgct     1200
attcactgac gccagaacga acactcgacg tgctcgaaga aacgtcgac aatccaaatt      1260
acgacacgct gctggagaac gtcttgaaat gtccatcacg ccggcccaaa cgaagcatta     1320
ccgatgactt cacactgacc agtccctacc tggggttctg cccgtattgc agacactcaa     1380
cgccgtgttt cagcccaata aaaattgaga acgtgtggga cgaatctgat gatggatcga     1440
ttagaatcca ggtctcggca caattcggct acaatcaggc aggcactgcg gatgtcacca     1500
aattccgtta catgtctttc gaccacgacc atgacatcaa ggaagacagt atggagaaaa     1560
tagctatcag cacatctgga ccctgccgtc gtcttggcca caaagggtac ttcctgttag     1620
ctcaatgtcc tccaggtgac agtgtaaccg tcagtatcac gagcggagca tctgagaatt     1680
catgcaccgt ggagaaaaag atcaggagga agtttgtcgg tagagaggag tacttgttcc     1740
cacccgtcca tggaaagctg gtaaagtgcc acgtttacga tcacttgaag gagacgtctg     1800
ccgggtacat aaccatgcac aggccaggcc cacacgcgta taagtcctat ctggaggaag     1860
cgtcaggcga agtgtacatt aaaccaccctt ctggcaagaa cgtcacctac gaatgtaagt    1920
gtggcgacta cagcacaggt atcgtgagca cgcgaacgaa gatgaacggc tgcactaaag     1980
caaaacagtg cattgcctac aagagcgacc aaacgaaatg ggtcttcaac tcgccggatc     2040
ttattaggca cacagaccac tcagtgcaag gtaaattgca cattccattc cgcttgacac     2100
cgacagtctg cccggttccg ttagctcaca cgcctacagt cacgaagtgg ttcaaaggca     2160
tcaccctcca cctgactgca atgcgaccaa cattgctgac aacgagaaaa ttggggctgc     2220
gagcagacgc aacagcagaa tggattacag ggtctcatc caggaatttt tctgtggggc      2280
gagaagggct ggagtacgta tggggtaacc atgaaccagt cagagtctgg gcccaggagt     2340
```

-continued

```
cggcaccagg cgacccacat ggatggccgc atgagatcat catccactat tatcatcggc    2400
atccagtcta cactgtcatt gtgctgtgtg gtgtcgctct tgctatcctg gtaggcactg    2460
catcatcagc agcttgcatc gccaaagcaa gaagagactg cctgacgcca tacgcgcttg    2520
caccgaacgc aacggtaccc acagcattag cggttttgtg ctgcattcgg ccaaccaacg    2580
ctgaaacatt tggagaaact ttgaaccatc tgtggtttaa caaccaaccg tttctctggg    2640
cacagttgtg cattcctctg gcagcgcttg ttattctgtt ccgctgcttt tcatgctgca    2700 tgccttttt attggttgca ggcgtctgcc tggggaaggt agacgccttc gaacatgcga    2760
ccactgtgcc aaatgttccg gggatcccgt ataaggcgtt ggtcgaacgc gcaggttacg    2820
cgccacttaa cctggagatc acggtcgtct catcggaatt aacaccttca actaacaagg    2880
agtacgtgac ctgcaaattc cacacagtca ttccttcacc acaagttaaa tgctgcgggt    2940
ccctcgagtg caaggcatcc tcaaaggcgg attacacatg ccgcgttttt ggcggtgtgt    3000 acccttttcat gtggggaggc gcacaatgct tctgtgacag tgagaacaca caactgagtg    3060
aggcgtacgt cgagttcgct ccagactgca ctatagatca cgcagtcgca ctaaaagttc    3120
acacagctgc tctgaaagtc ggcctgcgta tagtatacgg caacaccacc gcgcacctgg    3180
atacgtttgt caatggcgtc acgccaggtt cctcacggga cctgaaggtc atagcagggc    3240
cgatatcagc cgcttttca ccctttgacc ataaggtcgt catcagaaag gggcttgttt    3300
acaactacga cttccctgag tatggagcta tgaaaccagg agcgttcggc gatattcaag    3360
catcctcgct tgatgctaca gacatagtag cccgcactga catacggctg ctgaagcctt    3420
ctgtcaagaa catccacgtc ccctacaccc aagcagtatc agggtatgaa atgtggaaga    3480
acaactcagg acgaccctg caagaaacag caccatttgg atgtaaaatt gaagtggagc    3540
ctctgcgagc gtctaactgt gcttacgggc acatccctat ctcgattgac atccctgatg    3600
cagcttttgt gagatcatca gaatcaccaa caatttaga agttagctgc acagtagcag    3660 actgcatta ttctgcagac tttggtggtt ctctaacatt acagtacaaa gctgacaggg    3720
agggacattg tccagttcac tcccactcca cgacagctgt tttgaaggaa gcgaccacac    3780
atgtgactgc cgtaggcagc ataacactac attttagcac atcgagccca caagcaaatt    3840
ttatagtttc gctatgcggc aagaagtcca cctgcaatgc tgaatgtaaa ccaccggccg    3900
accacataat tggagaacca cataaagtcg accaagaatt ccaggcggca gtttccaaaa    3960
catcttggaa ctggctgctt gcactgtttg ggggagcatc atccctcatt gttgtaggac    4020
ttatagtgtt ggtctgcagc tctatgctta taaacacacg tagatgactg agcgcggaca    4080
ctgacatagc ggtaaaactc gatgtacttc cgaggaagcg tggtgcataa tgccacgcgc    4140
cgcttgacac taaaactcga tgtatttccg aggaagcaca gtgcataatg ctgtgcagtg    4200
tcacattaat cgtatatcac actacatatt aacaacacta tatcacttt atgagactca    4260 ctatgggtct ctaatataca ctacacatat tttacttaaa aacactatac acactttata    4320
aattctttta taattttct tttgctttag agcacactgg cggccgttac tagtggatcc    4380
gagctctaga gggcc                                                     4395
```

<210> SEQ ID NO 8
<211> LENGTH: 23
<212> TYPE: DNA
<213> ORGANISM: Artificial
<220> FEATURE:
<223> OTHER INFORMATION: DNA Primer

<400> SEQUENCE: 8
ggtagattga tgtcggtgca tgg                                    23

<210> SEQ ID NO 9
<211> LENGTH: 30
<212> TYPE: DNA
<213> ORGANISM: Artificial
<220> FEATURE:
<223> OTHER INFORMATION: DNA Primer

<400> SEQUENCE: 9
gtacttgact gactgttttt tttttttttt                             30

<210> SEQ ID NO 10
<211> LENGTH: 30
<212> TYPE: DNA
<213> ORGANISM: Artificial
<220> FEATURE:
<223> OTHER INFORMATION: DNA Primer

<400> SEQUENCE: 10
aatcaccctc tacggctgac ctaaataggt                             30

<210> SEQ ID NO 11
<211> LENGTH: 24
<212> TYPE: DNA
<213> ORGANISM: Artificial
<220> FEATURE:
<223> OTHER INFORMATION: DNA Primer

<400> SEQUENCE: 11
ggctgagctc aataggtgac gtag                                   24

<210> SEQ ID NO 12
<211> LENGTH: 30
<212> TYPE: DNA
<213> ORGANISM: Artificial
<220> FEATURE:
<223> OTHER INFORMATION: DNA Primer

<400> SEQUENCE: 12
gtagtgtata ttagagaccc atagtgagtc                             30

<210> SEQ ID NO 13
<211> LENGTH: 20
<212> TYPE: DNA
<213> ORGANISM: Artificial
<220> FEATURE:
<223> OTHER INFORMATION: DNA Primer

<400> SEQUENCE: 13
tccagatacg agctcatact                                        20

<210> SEQ ID NO 14
<211> LENGTH: 20
<212> TYPE: DNA
<213> ORGANISM: Artificial
<220> FEATURE:
<223> OTHER INFORMATION: DNA Primer

<400> SEQUENCE: 14
ggtgccgctg gaggccgttt                                        20

<210> SEQ ID NO 15
<211> LENGTH: 20
<212> TYPE: DNA

<213> ORGANISM: Artificial
<220> FEATURE:
<223> OTHER INFORMATION: DNA Primer

<400> SEQUENCE: 15
gatcttagga ggtcgatagc                                                         20

<210> SEQ ID NO 16
<211> LENGTH: 20
<212> TYPE: DNA
<213> ORGANISM: Artificial
<220> FEATURE:
<223> OTHER INFORMATION: DNA Primer

<400> SEQUENCE: 16
ggctgatgaa accactccac                                                         20

<210> SEQ ID NO 17
<211> LENGTH: 20
<212> TYPE: DNA
<213> ORGANISM: Artificial
<220> FEATURE:
<223> OTHER INFORMATION: DNA Primer

<400> SEQUENCE: 17
ccacccgtgt gctattcact                                                         20

<210> SEQ ID NO 18
<211> LENGTH: 20
<212> TYPE: DNA
<213> ORGANISM: Artificial
<220> FEATURE:
<223> OTHER INFORMATION: DNA Primer

<400> SEQUENCE: 18
cgccgtgttt cagcccaata                                                         20

<210> SEQ ID NO 19
<211> LENGTH: 20
<212> TYPE: DNA
<213> ORGANISM: Artificial
<220> FEATURE:
<223> OTHER INFORMATION: DNA Primer

<400> SEQUENCE: 19
tcacgagcgg agcatctgag                                                         20

<210> SEQ ID NO 20
<211> LENGTH: 20
<212> TYPE: DNA
<213> ORGANISM: Artificial
<220> FEATURE:
<223> OTHER INFORMATION: DNA Primer

<400> SEQUENCE: 20
ggcatcaccc tccacctgac                                                         20

<210> SEQ ID NO 21
<211> LENGTH: 20
<212> TYPE: DNA
<213> ORGANISM: Artificial
<220> FEATURE:
<223> OTHER INFORMATION: DNA Primer

<400> SEQUENCE: 21
ttgttattct gttccgctgc                                                         20

<210> SEQ ID NO 22
<211> LENGTH: 20
<212> TYPE: DNA
<213> ORGANISM: Artificial
<220> FEATURE:
<223> OTHER INFORMATION: DNA Primer

<400> SEQUENCE: 22
ctattgatca tgcagtcgca                              20

<210> SEQ ID NO 23
<211> LENGTH: 20
<212> TYPE: DNA
<213> ORGANISM: Artificial
<220> FEATURE:
<223> OTHER INFORMATION: DNA Primer

<400> SEQUENCE: 23
agtggagcct ctgcgagcgt                              20

<210> SEQ ID NO 24
<211> LENGTH: 20
<212> TYPE: DNA
<213> ORGANISM: Artificial
<220> FEATURE:
<223> OTHER INFORMATION: DNA Primer

<400> SEQUENCE: 24
gaggagtggg cgggaaaggc                              20

<210> SEQ ID NO 25
<211> LENGTH: 20
<212> TYPE: DNA
<213> ORGANISM: Artificial
<220> FEATURE:
<223> OTHER INFORMATION: DNA Primer

<400> SEQUENCE: 25
ctaaaactcg atgtatttcc                              20

<210> SEQ ID NO 26
<211> LENGTH: 20
<212> TYPE: DNA
<213> ORGANISM: Artificial
<220> FEATURE:
<223> OTHER INFORMATION: DNA Primer

<400> SEQUENCE: 26
acgcgaacga agatgaacgg                              20

<210> SEQ ID NO 27
<211> LENGTH: 20
<212> TYPE: DNA
<213> ORGANISM: Artificial
<220> FEATURE:
<223> OTHER INFORMATION: DNA Primer

<400> SEQUENCE: 27
actgtcattg tgctgtgtgg                              20

<210> SEQ ID NO 28
<211> LENGTH: 20
<212> TYPE: DNA
<213> ORGANISM: Artificial
<220> FEATURE:

<223> OTHER INFORMATION: DNA Primer

<400> SEQUENCE: 28
cacagtcatt ccttcaccac                                                    20

<210> SEQ ID NO 29
<211> LENGTH: 20
<212> TYPE: DNA
<213> ORGANISM: Artificial
<220> FEATURE:
<223> OTHER INFORMATION: DNA Primer

<400> SEQUENCE: 29
cgtcatcaga aagggcttg                                                     20

<210> SEQ ID NO 30
<211> LENGTH: 20
<212> TYPE: DNA
<213> ORGANISM: Artificial
<220> FEATURE:
<223> OTHER INFORMATION: DNA Primer

<400> SEQUENCE: 30
caaagctgac agggagggac                                                    20

<210> SEQ ID NO 31
<211> LENGTH: 20
<212> TYPE: DNA
<213> ORGANISM: Artificial
<220> FEATURE:
<223> OTHER INFORMATION: DNA Primer

<400> SEQUENCE: 31
ggaaagctgg taaagtgcca                                                    20

<210> SEQ ID NO 32
<211> LENGTH: 20
<212> TYPE: DNA
<213> ORGANISM: Artificial
<220> FEATURE:
<223> OTHER INFORMATION: DNA Primer

<400> SEQUENCE: 32
ggagaaccac ataaagtcga                                                    20

<210> SEQ ID NO 33
<211> LENGTH: 25
<212> TYPE: DNA
<213> ORGANISM: Artificial
<220> FEATURE:
<223> OTHER INFORMATION: DNA Primer

<400> SEQUENCE: 33
ggctaacgtg gacagggacg tgatg                                              25

<210> SEQ ID NO 34
<211> LENGTH: 20
<212> TYPE: DNA
<213> ORGANISM: Artificial
<220> FEATURE:
<223> OTHER INFORMATION: DNA Primer

<400> SEQUENCE: 34
ggctatcgac ctcctaagat                                                    20

```
<210> SEQ ID NO 35
<211> LENGTH: 20
<212> TYPE: DNA
<213> ORGANISM: WEEP0A

<400> SEQUENCE: 35
ctgtcggttc cctggtttag                                          20

<210> SEQ ID NO 36
<211> LENGTH: 20
<212> TYPE: DNA
<213> ORGANISM: Artificial
<220> FEATURE:
<223> OTHER INFORMATION: DNA Primer

<400> SEQUENCE: 36
ctggggaacg tcgccatact                                          20

<210> SEQ ID NO 37
<211> LENGTH: 20
<212> TYPE: DNA
<213> ORGANISM: Artificial
<220> FEATURE:
<223> OTHER INFORMATION: DNA Primer

<400> SEQUENCE: 37
cgttctccag cagcgtgtcg                                          20

<210> SEQ ID NO 38
<211> LENGTH: 20
<212> TYPE: DNA
<213> ORGANISM: Artificial
<220> FEATURE:
<223> OTHER INFORMATION: DNA Primer

<400> SEQUENCE: 38
tattgggctg aaacacggcg                                          20

<210> SEQ ID NO 39
<211> LENGTH: 20
<212> TYPE: DNA
<213> ORGANISM: Artificial
<220> FEATURE:
<223> OTHER INFORMATION: DNA Primer

<400> SEQUENCE: 39
cttcaagtga tcgtaaacgt                                          20

<210> SEQ ID NO 40
<211> LENGTH: 20
<212> TYPE: DNA
<213> ORGANISM: Artificial
<220> FEATURE:
<223> OTHER INFORMATION: DNA Primer

<400> SEQUENCE: 40
actccagccc ttctcgcccc                                          20

<210> SEQ ID NO 41
<211> LENGTH: 20
<212> TYPE: DNA
<213> ORGANISM: Artificial
<220> FEATURE:
<223> OTHER INFORMATION: DNA Primer

<400> SEQUENCE: 41
```

-continued

| | |
|---|---|
| gttcgaccaa cgccttatac | 20 |

<210> SEQ ID NO 42
<211> LENGTH: 20
<212> TYPE: DNA
<213> ORGANISM: Artificial
<220> FEATURE:
<223> OTHER INFORMATION: DNA Primer
<400> SEQUENCE: 42

| | |
|---|---|
| aagggtgaaa aagcggctga | 20 |

<210> SEQ ID NO 43
<211> LENGTH: 20
<212> TYPE: DNA
<213> ORGANISM: Artificial
<220> FEATURE:
<223> OTHER INFORMATION: DNA Primer
<400> SEQUENCE: 43

| | |
|---|---|
| ggtgattctg atgatctcac | 20 |

<210> SEQ ID NO 44
<211> LENGTH: 20
<212> TYPE: DNA
<213> ORGANISM: Artificial
<220> FEATURE:
<223> OTHER INFORMATION: DNA Primer
<400> SEQUENCE: 44

| | |
|---|---|
| tggaaactgc cgcctggaat | 20 |

<210> SEQ ID NO 45
<211> LENGTH: 20
<212> TYPE: DNA
<213> ORGANISM: Artificial
<220> FEATURE:
<223> OTHER INFORMATION: DNA Primer
<400> SEQUENCE: 45

| | |
|---|---|
| ccttgatgtc atggtcgtgg | 20 |

<210> SEQ ID NO 46
<211> LENGTH: 20
<212> TYPE: DNA
<213> ORGANISM: Artificial
<220> FEATURE:
<223> OTHER INFORMATION: DNA Primer
<400> SEQUENCE: 46

| | |
|---|---|
| tgcactgagt ggtctgtgtg | 20 |

<210> SEQ ID NO 47
<211> LENGTH: 20
<212> TYPE: DNA
<213> ORGANISM: Artificial
<220> FEATURE:
<223> OTHER INFORMATION: DNA Primer
<400> SEQUENCE: 47

| | |
|---|---|
| atgtttcagc gttggttggc | 20 |

<210> SEQ ID NO 48
<211> LENGTH: 20
<212> TYPE: DNA
<213> ORGANISM: Artificial -continued

```
<220> FEATURE:
<223> OTHER INFORMATION: DNA Primer

<400> SEQUENCE: 48
gtgttctcac tgtcacagaa                                              20

<210> SEQ ID NO 49
<211> LENGTH: 20
<212> TYPE: DNA
<213> ORGANISM: Artificial
<220> FEATURE:
<223> OTHER INFORMATION: DNA Primer

<400> SEQUENCE: 49
atgtgtggtc gcttccttca                                              20
```

STRAIN OF THE WESTERN EQUINE ENCEPHALITIS VIRUS

REFERENCE TO RELATED APPLICATIONS

This application is a non-provisional application of provisional application No. 60/256,948 filed on Dec. 21, 2000.

FIELD OF THE INVENTION

This invention relates to the cloning, sequencing and expression of the structural genes of western equine encephalitis (WEE) virus strain 71V-1658 and the development and use of the DNA-based vaccine against WEE.

BACKGROUND OF THE INVENTION

LIST OF PRIOR ART LITERATURES

Ausubel, F. M., et al, editors. (1995). *Current Protocols in Molecular Biology*, New York: John Wiley & Sons.

Bell, J. R., Bond, M. W., Nukapiller, M. B., Strauss, E. G., Strauss, J. H., Yamamoto, K, & Simizu, B. (1983). Structural proteins of western equine encephalitis virus: amino acid compositions and N-terminal sequences. *Journal of Virology* 45, 708–714.

Bird, B. R. & Forrester, F. T. (1981). *Basic Laboratory Techniques In Cell Culture*. Atlanta: U.S. Department of Health and Human Services, Centers for Disease Control.

Calisher, C. H. & Karabatsos, N. (1988). Arbovirus serogroups: definition and geographic distribution. In *The Arboviruses: Epidemiology and Ecology*, Vol. I,.pp. 19–57. Edited by T. P Monath. CRC Press: Boca Raton, Fla.

Calisher, C. H., Shope, R. E, Brandt, W., Casals, J., Karabatsos, N., Murphy, F. A., Tesh, R. B., & Wiebe, M. E. (1980). Proposed antigenic classification of registered arbovirusess. *Intervirology* 14, 229–232.

Calisher, C. H., Karabatsos, N., Lazuick, J. S. Monath, T. P., & Wolff, K. L. (1988). Reevaluation of the western equine encephalitis antigenic complex of alphaviruses (family Togaviridae) as determined by neutralization tests. *American Journal of Tropical Medicine and Hygiene* 38, 447–452.

Cilnis, M. J., Kang, W. & Weaver, S. C. (1996). Genetic conservation of Highlands J viruses. *Virology* 218, 343–351.

Frohman, M. A., Dush, M. K & Martin, G. R. (1988). Rapid production of full-length cDNAs from rare transcripts: Amplification using a single gene-specific oligonucleotide primer. *Proceedings of the National Academy of Science USA* 85, 8998–9002.

Hahn, C. S., Lustig, S., Strauss, E. G. & Strauss, J. H. (1988). Western Equine Encephalitis virus is a recombinant virus. *Proceedings of the National Academy of Science USA* 85, 5997–6001.

Johnson, R. E. & Peters, C. J. (1996). Alphaviruses. In *Fields Virology*, 3rd edn, pp. 843–898. Edited by B. N. Fields, et al., New York: Raven Press.

Kuhn, R., Hong, Z. & Strauss, J. H. (1990). Mutagenesis of the 3' nontranslated region of Sindbis virus RNA. *Journal of Virology* 64, 1465–1476.

Kuhn, R. J., Niesters, H. G. M., Hong, Z. & Strauss, J. H. (1991). Infectious RNA transcripts from Ross River virus cDNA clones and the construction and characterization of defined chimeras with Sindbis. *Virology* 182, 430–441.

Krieg, A. M., Yi, A.-K., Schorr, J. and Davis, H. L. (1998). The role of CpG dinucleotides in DNA vaccines. *Trends Microbiol.* 6, 23–27.

McCluskie, M. J., Davies, H. L. (1999). Novel strategies using DNA for the induction of mucosal immunity. *Critic. Rev. in Immunol.* 19, 303–329.

Ou, J.-H., Trent, D. W. & Strauss, J. H. (1982). The 3' non-coding regions of alphavirus RNAs contain repeating sequences. *Journal of Molecular Biology* 156, 719–730.

Ou, J-H., Strauss, E. G. & Strauss, J. H. (1983). The 5' terminal sequences of the genomic RNAs of several alphaviruses. *Journal of Molecular Biology* 168, 1–15.

Pardoll, D R, Beckering, A M. (1997). Exposing the immunology of naked DNA vaccines. *Immunity* 3;165–169.

Pfeffer, M., Proebster, B., Kinney, R. M. & Kaaden, O-R. (1997). Genus-specific detection of alphaviruses by a semi-nested reverse transcription reaction. *American Journal of tropical Medicine and Hygiene* 57, 709–718.

Pfeffer, M., Kinney, R. M. & Kaaden, O-R. (1998). The alphavirus 3'-nontranslated region: Size heterogeneity and arrangement of repeated sequence elements. *Virology* 240, 100–108.

Prayaga, S. K., Fuller, D. H., Haynes, J. R. & Murphey-Corb, M. (1995). Particle-mediated nucleic acid immunization. *Vaccines* 95, 105–109.

Reisen, W. K & Monath, T. P. (1988). Western equine encephalomyelitis, pp. 89–137. In *The Arboviruses: Epidemiology and Ecology, Vol. V*. Edited by T. P. Monath. CRC Press: Boca Raton, Fla.

Robinson, H. L., Feltquate, D. M., Morin, M. J., Haynes, J. R., Webster, R. G. (1995). DNA vaccines: A new approach to immunization. *Vaccine* 95:69–75.

Sambrook, J., Fritsch, E. F., & Maniatis, T. (1989). *Molecular Cloning, a Laboratory Manual, 2nd edn*. Cold Spring Harbor: Cold Spring Harbor Laboratory.

Schlesinger, S. & Schlesinger, M. J. (1996). Togaviridae: The viruses and their replication, In *Fields Virology*, 3rd edn, pp. 825–841. Edited by B. N. Fields, et al. New York: Raven Press.

Strauss, J. H., & Strauss, E. G. (1988). Evolution of RNA viruses. *Annual Review of Microbiology* 42, 657–683.

Strauss, J. H., & Strauss, E. G. (1994). The alphaviruses: gene expression, replication, and evolution. *Microbiological Review* 58, 491–562.

Strauss, E. G., Rice, C. M. & Strauss, J. H. (1983). Sequence coding for the alphavirus nonstructural proteins is interrupted by an opal termination codon. *Proceedings of the National Academy of Science USA* 80, 5271–5275.

Strauss, E. G., Rice, C. M. & Strauss, J. H. (1984). Complete nucleotide sequence of the genomic RNA of Sindbis virus. *Virology* 133, 92–110.

Trent, D. W., & Grant, J. A. (1980). A comparison of new world alphaviruses in the western equine encephalomyelitis complex by immunochemical and oligonucleotide fingerprint techniques. *Journal or General Virology* 47:261–282.

Weaver, S. C., Hagenbaugh, A., Bellew, L. A., Netesov, S. V., Volchokov, V. I., Chang, G.-J J., Clarke, D. K., Gousset, L., Scott, T. W., Trent, D. W. & Holland, J. J. (1993). A comparison of the nucleotide seqeunces of eastern and western equine encephalomyelitis viruses with those of other alphaviruses and related RNA viruses. *Virology* 197, 375–390.

Weaver, S. C., Kang, W, Shirako, Y., Rumenapf, T., Strauss, E. G. & Strauss, J. H. (1997) Recombinational history and molecular evolution of western equine encephalomyelitis complex alphaviruses. *Journal of Virology* 71,613–623.

Wolff, J. A., Malone, R. W., Williams, P., Chong, W., Aesasi, G., Jani, A., Felgner, P. L. (1990). Direct gene transfer into mouse muscle in vivo. *Science* 247,1465–1468.

The alphaviruses are a group of about 27 enveloped viruses with a positive sense, nonsegmented single-stranded RNA genome (Calisher et al., 1980; Strauss and Strauss, 1988). The alphavirus disclosed in this invention, western equine encephalitis virus (WEE), is a member of the WEE antigenic complex and is serologically related to the Sindbis (SIN), Highlands J (HJ), Fort Morgan, Buggy Creek, and Aura viruses (Calisher & Karabatsos, 1988; Calisher et al., 1988). WEE is endemic in western North America and strains/varieties have been isolated from Argentina (AG80-646), Brazil (BeAr 102091) and the former Soviet Union (Y62-33) (Johnson and Peters, 1996; Weaver et al., 1997). In nature, WEE is transmitted from its amplifying hosts or reservoir in wild birds, to man and horses, by mosquitoes (*Culex tarsalis* being the principal vector). While the endemic cycle has resulted in only a limited number of human infections in recent years, in the past, major epidemics of WEE have been recorded. The most extensive epidemic, including 3,336 recognized human cases and 300,000 cases of encephalitis in horses and mules, occurred in the western United States and Canada in 1941 (Reisen & Monath, 1988; Johnson and Peters, 1996).

All alphaviruses share a number of structural, sequence, and functional similarities, including a genome with two polyprotein gene clusters (reviewed in Strauss & Strauss, 1994; Schlesinger & Schlesinger 1996). The genomic organization of these viruses is conserved (see FIG. 1), with the nonstructural proteins translated directly from the 5' two-thirds of the genomic RNA. A subgenomic positive-stranded RNA (the 26S RNA), is identical to the 3' one-third of the genomic RNA and serves as the translational template for the structural proteins (capsid, E3, E2,6K and E1).

The nonstructural proteins (nsP1, nsP2, nsP3 and nsP4) are also synthesized as a polyprotein and processed into the four nsPs by a nsP2 protease. Two versions of the nonstructural polyprotein are synthesized in alphavirus-infected cells, due to frequent readthrough of an opal codon between the nsP3 and nsP4 genes in several alphaviruses (Strauss et al., 1983). The nsPs function in a complex with host factors to replicate the genome and transcribe the subgenomic mRNA. Alphaviruses have characteristic conserved sequences at the extreme 5' and 3' domains and the intergenic region (Ou et al., 1982, 1983; Pfeffer et al., 1998). These conserved domains are required for viral growth and replication and are believed to be important in promotion of protein synthesis and the initiation of RNA-dependent RNA polymerase activity.

The relationship of different WEE isolates to each other has been demonstrated using neutralization tests (Calisher et al., 1988). Additionally, several strains of WEE were typed by oligonucleotide fingerprinting, and found to have greater than 90% nt homology (Trent & Grant, 1980). The N-terminal sequences of the nucleocapsid, and the E1 and E2 glycoproteins have been determined by Edman degradation, and the E1 and E2 proteins were found to have 82% and 71% homology, respectively, to SIN (Bell et al, 1983). Hahn et al. (1988) sequenced the 26S region of WEE strain BFS1703. They proposed that WEE originated as a hybrid virus, formed by recombination of an EEE and a Sindbis-like virus, most likely during a co-infection event. They suggested that two crossover events occurred, one within the E3 gene, the other within the 3' nontranslated terminal region (NTR), resulting in a virus whose nonstructural domain, intragenic region, and capsid protein are similar to EEE, with envelope proteins showing homology to SIN.

Weaver et al. (1993) sequenced part of the nonstructural domain (nsP2 and nsP3 genes) of strain 5614, demonstrating this area also shows homology to EEE. Short regions within the nsP4 gene and the E1 protein/3' NTR have been determined for many WEE strains, allowing a preliminary assessment of the nucleic acid phylogenetic relationships within the WEE antigenic complex (Weaver et al., 1997). Serological studies (Calisher et al., 1988) and preliminary sequence determination (Cilnis et al., 1996; Weaver et al., 1997) of the HJ genome suggests this is another closely related virus, and most likely a descendant of the same recombinant viral ancestor as modem WEE.

A highly conserved region of the alphavirus nsP1 gene has been identified, and proved suitable for use in a polymerase chain reaction (PCR)-based genetic assay for alphaviruses, including WEE (Pfeffer et al., 1997). Phylogenetic analysis of this PCR fragment yielded similar results to those obtained by Weaver et al., (1997) for a PCR fragment in the nsP4 gene.

In terms of therapy or prophylaxis, there are very limited possibilities. An inactivated vaccine to WEE is under investigational new drug (IND) status. The vaccine uses formalin-inactivation of cell culture supernatants from WEE-infected tissue culture. It requires a minimum of 3 doses, yearly monitoring of antibody titer and possible boosters. Its effectiveness in the protection against an aerosol challenge of WEE has yet to be established. A WEE live attenuated vaccine based on an infectious clone is under development (J. Smith, personnel communication). The area of DNA immunization is relatively new, and has been reviewed in Hassett and Whitton, 1996; Donnelly et al, 1997. Similar to live, attenuated vaccines, DNA vaccines are known to stimulate both humoral and cellular immune responses (Pardoll and Backering, 1997; McCuskie and Davies, 1999). Much of the focus has been on methods to deliver and efficiently express the cloned products. Intramuscular administration of DNA has been one of the original methods used (Wolff et al, 1990). A second method uses ballistic delivery of DNA coated gold particles, using high pressure helium gas to propel the particles into the epidermis and dermis of animals (Prayaga et al, 1995, reviewed by Robinson et al, 1995).

The Applicant identified a number of related areas of research, including the development of subunit vaccines to WEE. In the present invention, the Applicant disclosed the cloning, sequencing and expression of the structural genes of a WEE virus (strain 71V-1658), as described in Netolitzky et al., (2000) "Complete genomic RNA sequence of western equine encephalitis virus and expression of the structural genes." *Journal of General Virology* 81, 151–159, which is herein incorporated by reference. The DNA construct (pCXH-3), and a second construct (pVHX-6) were used in DNA immunization studies in a mouse model for protection against intranasal administered WEE.

SUMMARY OF THE INVENTION

The present invention is directed to the development of a DNA-subunit vaccine to the WEE virus and its use against such virus. More specifically, DNA to structural components of the WEE virus are expressed and used as the subunit vaccine.

The present invention provides for the complete nucleotide sequence of WEE strain 71V-1658. Two novel cDNA clones, pCXH-3 and pVHX-6 are also disclosed as effective vectors for gene expression.

The present invention also provides the complete nucleotide sequence for the structural gene pcDWXH-7.

It further provides for a process for preparing a recombinant DNA vaccine against WEE virus, comprising cloning and sequencing of 26S region of a WEE virus strain 71V-1658 under conditions suitable to effect in vitro transcription and translation of the functional recombinant DNA expression vector pCXH-3 and pVHX-6.

BRIEF DESCRIPTION OF THE DRAWINGS

FIG. 1. Diagram showing the WEE 71V-1658 sequencing strategy. The location of PCR probe sequences used to screen the WEE cDNA library are also indicated, along with the genomic organization of the virus.

FIG. 2. Multiple sequence alignment.

FIG. 3. Stem loop structures in the 5' NTR.

FIG. 4. Stem loop structures in the 3' NTR.

FIG. 5. Phylogenetic relationship of the WEE nonstructural region compared to other alphaviruses.

FIG. 6. Expression of WEE structural genes in cell culture.

FIG. 7. In vitro transcription and translation of WEE expression vectors.

FIG. 8. WEE mouse infectivity model.

FIG. 9. Protection using ballistic delivery of pCXH-3.

FIG. 10. Protection using ballistic delivery of pVHX-6

FIG. 11. Protection using ballistic delivery of pVHX-6.

DETAILED DESCRIPTION OF THE INVENTION

The complete nucleotide sequence of the 71V-1658 strain of western equine encephalitis (WEE) virus was determined (minus twenty-five nucleotides from the 5' end) and shown in SEQ ID NO: 1. A 5' RACE reaction was used to sequence the 5' terminus from WEE strain CBA87. The deduced WEE genome was 11,508 nucleotides in length, excluding the 5' cap nucleotide and 3' poly(A) tail. The nucleotide composition was 28% A, 25% C, 25% G and 22% U residues. Comparison with partial WEE sequences of strain 5614 (nsP2–nsP3 of the nonstructural region) and strain BFS 1703 (26S structural region) revealed comparatively little variation; a total of 149 nucleotide differences in 8624 bases (1.7% divergence), of which only 28% of these changes (42 nucleotides) altered the encoded amino acids. Comparison of deduced nsP1 and nsP4 amino acid sequences from WEE with the corresponding proteins from eastern equine encephalitis (EEE) yielded identities of 84.9% and 83.8%, respectively. Previously uncharacterized stem loop structures were identified in the nontranslated terminal regions.

A 3100 bp clone was identified (pcDNA-12) from the 3' end of the structural genes. A 1500 bp fragment was PCR amplified and cloned into the 5' end of pcDNA-12 to produce a complete clone of the structural genes (XH-7) as shown in SEQ ID NO: 2. A cDNA clone (pCXH-3) in which the structural genes of WEE strain 71V-1658 were placed under the control of a cytomegalovirus promoter was made, and transfected into tissue culture cells. The viral envelope proteins were functionally expressed in tissue culture, as determined by histochemical staining with monoclonal antibodies which recognize WEE antigens. The construct was used to immunize mice ballistically and intramuscularly. Mice protected ballistically had a significantly reduced risk of infection, against a subsequent intranasal challenge with WEE virus. A new vector was constructed to determine if increased levels of expression could be obtained. The construct used a pVAX vector to express the WEE structural genes (pVHX-6). Upstream portion of the pVHX-6 vector to where it becomes the XH-7 sequence is shown as SEQ ID NO: 3. The remaining nucleotide sequence of pVHX-6 from the point of divergence is identical to that of structural gene pcDWXH-7 of SEQ ID NO: 2.

Materials and Methods

Virus Culture and Purification

Tissue culture was maintained in accordance with established methods (Bird & Forrester, 1981). Minimal essential media containing 5% fetal calf serum (5% DMEM) was used to grow Vero (CRL 1586) and Chinese hamster ovary (CHO) K1 (CCL 61) cells obtained from American Type Culture Collections. A 10% suckling mouse brain (SMB) suspension of WEE strain 71V-1658 was kindly provided by Dr. Nick Karabatsos, Centers for Disease Control, Fort Collins, Colo. WEE Fleming and California strains were purchased from ATCC (Mannanas, Va.). WEE B11 and CBA87 strains were kindly provided by Dr. George Ludwig, United States Army Medical Research Institute of Infectious Disease (Frederick, Md.). Seed stocks of WEE strains were made by inoculation of Vero cells with virus suspensions at a multiplicity of infection (MOI) of less than 0.1. For RNA isolation, virus stocks were prepared by infecting Vero cells at a MOI of 10. The virus was precipitated from cleared supernatant by the addition of polyethylene glycol MW 6000 to 7%(w/v) and NaCl to 2.3%(w/v). It was subsequently purified on a 20–60%(w/w) continuous sucrose gradient, followed by resuspension in PBS.

Nucleic Acid Preparation

Viral RNA used in WEE strain 71V-1658 library construction was prepared by the lysis of virus in 0.5%(w/v) sodium dodecyl sulfate (SDS), and RNA extracted using the cesium chloride/guanidium isothiocyanate method previously described (Sambrook et al., 1989). RNA was precipitated using sodium acetate and ethanol, then stored at −70° C. Prior to use, RNA was washed with 80%(v/v) ethanol, dried and dissolved in nuclease-free water (Promega, Madison, Wis.). Integrity of the RNA was checked on formaldehyde agarose gels (Sambrook et al., 1989). A cDNA library of WEE strain 71V-1658 was made by Invitrogen (San Diego, Calif.), by the ligation of cDNA into the BstXI site of prepared pcDNAII vector, and electroporation into electrocompetent DH1 F' *Escherichia coli* cells. Manipulation of RNA and DNA followed established procedures (Sambrook et al, 1989; Ausubel et al., 1995). Rapid plasmid preparations were made using the Wizard™ plasmid purification kit (Promega, Madison, Wis.). Large-scale plasmid preparations used the alkali lysis protocol as modified by Qiagen (Chatsworth, Calif.). For PCR, RT-PCR and DNA sequencing, oligonucleotide primer design was guided by information from WEE strain BFS1703 and other partially sequenced WEE strains (Hahn et al., 1988; Weaver et al., 1993), and from regions of sequence conservation (Ou et al., 1982 &1983). Oligonucleotides were synthesized and gel purified either at the Regional DNA Synthesis Laboratory (Calgary, Alberta), or on a Beckman Oligo 1000 DNA synthesizer. A catalog with the sequences of primers used is listed in Table 1.

Construction of pCXH-3

The Invitrogen WEE library was screened by dot blot hybridization (Sambrook et al., 1989) with [$^{32}$P]-labeled, random primed RT-PCR fragments as probes (Amersham, Oakville, ON). A 3100 bp insert, pcDW-12, was identified, and corresponded to the 3' end of the 26 S RNA. The missing 5' end of the 26S region was generated by RT-PCR using the primers WEE5'Sst1 and WEEP3 (Table 1). The 1500 bp SstI/NcoI restricted fragment was inserted into the plasmid, phT3T7BM+(Boehringer Mannheim, Laval, PQ), to generate a XbaI site on the 5' end. The 1500 bp XbaI/NcoI fragment was excised, gel purified and inserted into the XbaI and NcoI restriction sites of pcDW-12. The resulting clone, pcDWXH-7, encoded the complete 26S region of WEE 71V-1658. The structural gene insert from pcDWXH-7 was cloned into the mammalian expression vector, pCI (Promega, Madison, Wis.). The pcDWXH-7 plasmid was first linearized using HindIII, followed by a Klenow fragment reaction to fill in the 5' overhang. The insert was then excised using XbaI, gel purified and ligated into the XbaI/SmaI digested pCI vector. The isolated recombinant plasmid, pCXH-3, was characterized as having the correct insert by restriction mapping.

Construction of pVHX-6

The clone, pcDWXH-7, encoded the complete 26S region of WEE 71V-1658 was digested with Sac I, and religated in the reverse orientation. The isolate, pcDWHX-45, contained the complete 26S of WEE, with the reverse cloning sites (HindIII on the 5' end and XbaI on the 3' end). The WEE 26S gene segment was excised from pcDWHX-45, and cloned into the HindIII and XbaI sites of the mammalian expression vector, pVAX (Invitrogen, La Jolla, Calif.). After transformation into *E. coli* DH10α (Life Sciences, Burlington, ON) and screening of inserts by restriction analysis, a resulting isolate, pVHX-6 was identified. SEQ ID NO: 3 shows the upstream portion of the pVHX-6 vector to where it becomes the XH-7 sequence. The remaining nucleotide sequence of pVHX-6 from the point of divergence is identical to that of structural gene pcDWXH-7 of SEQ ID NO: 2.

Expression of the Structural Genes of WEE

The pCXH-3 expression vector was transfected into Vero or CHO K1 cells using the cationic lipid, Lipofectamine™ (Gibco/BRL, Burlington, ON). Briefly, Vero or CHO K1 cells were grown to 30–50% confluency in Costar 6-well plates. The monolayers were transfected with pCXH-3 in accordance with the manufacturer's directions, for a period of 5 hrs, followed by a further 29 hr incubation after the addition of 5% DMEM. The monolayers were fixed in methanol:acetone (1:1) for 5 min and washed with PBS containing 0.1%(v/v) Tween 20 and 3% BSA (PBS-TB). The cells were incubated 45 min at 37° C. with a 1/100 dilution (in PBS-TB) of concentrated cell supernatant from hybridoma cell lines expressing monoclonal antibodies to the WEE E1 (clone 11D2) or E2 (clone 3F3) proteins, followed by washing with PBS-TB. Monolayers were incubated with a 1/4000 dilution of goat anti-mouse IgG/IgM (H & L) horse radish peroxidase conjugate (Caltag, So. San Francisco, Calif.) for 45 min at 37° C. After washing with PBS-T, 2 mL of TruBlue™ HRP substrate (Kirkegaard & Perry Laboratories, Gaitherburg, Md.) was added, and plates were incubated a further 30 min at room temperature, followed by microscopic examination.

In a second method, one-step in vitro transcription and translation reactions using the TNT coupled system (Promega Corporation, Madison, Wis.) was used to express the gene products from both pCXH-3 and pVHX-6, as both have an upstream T7 promoter which can be used for in vitro expression of inserts. The RNA was translated in the presence of [$^{35}$S]methionine to produce radiolabeled WEE proteins, which were further processed with canine pancreatic microsomal membranes. All components of the in vitro transcription and translation reactions were incubated together for 90 min at 30° C. Results were analyzed by SDS-PAGE or radioimmunoprecipitation.

Radioimmunoprecipitation

The TNT reactions were diluted to a volume of 500 ml with RIP buffer consisting of 0.15 M sodium chloride, 0.1% SDS, 50 mM Tris-HCl pH 7.4, and 1% Triton X-100. They were then preabsorbed by incubating with 75 L of protein G-agarose (Gibco BRL) for 30 min at room temperature. The samples were centrifuged at 13,000 rpm for 1 min, and the supernatants were then immunoprecipitated with either 100 µL of supernatants from anti-WEE hybridoma cells or 20 µg of purified anti-WEE antibodies. The reactions were incubated for 1.5 hr at room temperature, after which 75 µL of protein G-agarose was added. The reactions were incubated for an additional 30 min at room temperature. Immunoprecipitated proteins were collected by centrifuging at 13,000 rpm for 1 min. The pellets were washed with 500 µL of RIP buffer and centrifuged at 13,000 rpm for 1 min; this step was repeated three additional times. The pellets were resuspended in 2× Laemmli sample buffer (Bio-Rad Laboratories) containing fresh 2% b-mercaptoethanol and heated at 100° C. for 10 min. The samples were centrifuged at 13,000 rpm for 1 min, and the supernatants were collected. The immunoprecipitated [$^{35}$S]labeled WEE proteins were further analyzed by SDS-PAGE and autoradiography. Radiolabelled [$^{14}$C]molecular weight markers from Amersham Pharmacia Biotech were also run on the polyacrylamide gels.

DNA Sequencing

Automated sequencing of the 26S region was performed using the ABI Prism Dye Terminator Cycle Sequencing or Big-Dye.TM. Terminator Cycle Sequencing Kite or plasmid templates according to the manufacturer's instructions (PE-Applied Biosystems, Foster City, Calif.). Sequencing reactions were purified on Centri-Sep.TM. columns (Princeton Separations, Adelphia, N.J.), dried and analyzed on an ABI 373 or 310 automated sequencer. For the nonstructural region, template cDNAs were generated in a single-step integrated RT-PCR procedure using the Titan.TM. RT-PCR kit (Boehringer Mannheim, Laval, PQ), following the manufacturer's suggested protocols. RT-PCR products were purified using the QIAquick.TM. PCR Purification kit (Qiagen, Chatsworth, Calif.) and sequenced (50–100 ng DNA per reaction). The extreme 5' end of the genome was not sequenced in WEE 71V-1658. However, a 5' RACE reaction (Frohman et al., 1988) was used to obtain a cDNA fragment from the 5' terminus of WEE strain CBA87. Briefly, primer WEE559(GGTAGATIGATGTCGGTGCATGG-SEQ ID NO: 8) was used to prime reverse transcription of the 5' terminus of the viral RNA. After poly(A) tailing of the cDNA with terminal transferase, a plus sense primer (GTACTTGACTGACTGTTTTTTTTTTTTTT-SEQ ID NO: 9) was used in conjunction with WEE559 for amplification of the 5' terminus.

Nucleotide Sequence Analysis and Assembly

Sequence traces were edited manually and assembled using the Seqman component of the Lasergene DNA analysis software (DNASTAR, Madison, Wis.). Codon preferences and patterns were assessed using the CodonUse and CodonFrequency programs, while the overall frequency of mononucleotide and dinucleotides was calculated using the Composition program (Wisconsin Package, Version 9.0, Genetics Computer Group, Madison, Wis.). Quantitative assessments of sequence similarities (nucleotide and amino acid), were calculated by preliminary alignment using the Pileup program, followed by manual alignment adjustment, and analysis with the Distances program (GCG). Amino acid sequences aligned as described, were used as the basis for generating phylogenetic trees (GCG). The GeneQuest module of the Lasergene program (DNASTAR, Madison, Wis.) was used to predict and calculate RNA secondary structures at the ends of the genomic RNA using minimal energy calculations. Multiple sequence alignments were accomplished using the Clustal component of MegAlign (DNASTAR). The complete WEE genomic nucleotide sequence has been submitted to GenBank (Accession Number AF143811).

Administration of DNA or Inactivated Virus

DNA solutions or an inactivated WEE virus vaccine in PBS, were administered to the mice by ballistic or intramuscular (IM) routes. For IM route of administration, a 27 g needle was used to deliver 50 µg of DNA (pCXH-3 or pCI-negative control) or 50 µL of inactivated WEE vaccine (SALK WEE inactivated vaccine). The volume of inoculum used was 100 µL, diluted in PBS. Fifty µL was administered IM to each of the hind leg muscles of a mouse. When boosters were given, they were administered 14–28 days apart. For ballistic administration, mice were shaved in the abdominal area with electric hair clippers. The mouse was subjected to ballistic delivery of DNA coated onto gold particles following the manufacturer's standard specifications. The Helios Gene Gun (Biorad, Mississauga, ON) was used as directed, at a pressure setting of 400 psi. Mice were given 1.25 µg DNA and 0.5 mg gold, 1 µm diameter, per shot, and up to three shots for one dose time. Boosters were given 14–28 days apart. The mice were challenged 14–28 days after the final booster.

Mouse Infectivity with WEE

Female BALB/c mice, 17–25 g, were obtained from the mouse breeding colony at Defence Research Establishment Suffield (DRES), with the original breeding pairs purchased from Charles River Canada (St. Constant, Quebec, Canada). The use of these animals was reviewed and approved by Animal Care Committee at DRES. Care and handling of the mice followed guidelines set out by the Canadian Council on Animal Care. Virus was administered to the mice by intranasal (IN) or intraperitoneal (IP) routes. The volumes of inoculum used were 50 µL for IN and 100 µL for IP. For IN administration, mice were anaesthetized with sodium pentobarbital (50 mg/kg body weight, intraperitoneal). When the animals were unconscious, they were carefully supported by hands with their nose up, and the virus suspension in PBS was gently applied with a micropipette into the nostrils. The applied volume was naturally inhaled into the lungs. For IP infection, the mouse was manually restrained, and a 1 ml tuberculin syringe fitted with a 27 g needle was used to administer approximately 100 µL of the virus suspension in PBS. Infected animals were observed daily, for up to 14 days post infection.

Results

Complete Nucleotide Sequence of WEE Genome and Deduced Amino Acids

The nucleotide sequence of WEE strain 71V-1658 (SEQ ID NO: 1) was determined via several distinct sequencing strategies, as summarized in FIG. 1. The 5' terminus of 25 nt was not determined for this strain. However, it was determined by sequencing a 5' RACE product from strain CBA87. Excluding the terminal 5' cap structure and the 3' poly(A) tail, the genomic sequence of WEE was found to be 11,508 bases long. The base composition was 28% A, 25% C, 25% G, and 22% U. The dinucleotide usage of the WEE genome was compared with those values anticipated from the base composition. Several dinucleotides were found in lower proportions than anticipated, notably UpA (81%), CpG (83%) and CpC (85%) (data not shown). Codons containing the CpG dinucleotide were present at 82% of the anticipated value, including codons for serine (78%), proline (80%) and arginine (78%).

The WEE 71V-1658 sequence was used to conduct a variety of phylogenetic analyses with previously determined alphavirus sequences. The alphaviruses used in the analyses included EEE strain North American variant (Genbank Acc. No. X67111), O'Nyong Nyong (ONN) strain Gulu (Genbank Acc. No. M33999), Ross River (RR) strain NB5092 (Genbank Acc. No. M20162), Semliki Forest (SFV) (Genbank Acc. No. J02361), SIN strain HR (Genbank Acc. No. J02363) and VEE ID (Genbank Acc. No. L04653). The degree of conservation among the various sequences (nucleotide and amino acid) through the stereotypical alphavirus genome is shown in Table 2. The carboxyterminal domain of nsP3, which consistently fails to exhibit homology among sequenced alphaviruses, was excluded from this comparison as it has been adjusted for in previous analysis (Weaver et al., 1993). The deduced amino acid sequences for nsP1–4 of WEE 71V-1658 demonstrated closest identity to the corresponding proteins from EEE (Table 1), reflecting similar observations made for nsP2 and nsP3 of WEE 5614 and EEE (Weaver et al., 1993).

Nontranslated Terminal Regions

Alignment of the 5' terminal nucleotide sequences of WEE CBA87 and WEE 71V-1658 is shown in FIG. 2a, along with a comparison of the 5' termini from EEE and VEE. The close similarity between WEE and EEE, has been verified experimentally, in that a EEE/Highlands J degenerate primer, EHJ5', was able to PCR amplify the 5' end of the WEE genome, while an analogous SIN primer could not (data not shown).

Potential stem loop structures were found in WEE 71V-1658, including a stem loop at the extreme 5' terminus (2–30) and a pair of stem loops (137–189) (FIG. 3a). The homologous structures for EEE are also shown (FIG. 3b) (Ou et al., 1983). Minimal energy values calculated for the stem loops were similar between WEE and EEE. Further analysis of the region between the structures described above, indicated a large, highly base-paired stem loop structure (39–131), that had not been previously described, and was observed in SIN and EEE in a similar location (data not shown).

The sequence of WEE 71V-1658 3' NTR, overall, shared little homology with any of the alphaviruses examined, but included the highly conserved 19 nt region at the 3' end (11490–11508), which was identical to that determined for WEE BFS1703 by Hahn et al., 1988. Two copies of the characteristic 40 base Sindbis-like terminal repeats as previously reported (On et al., 1982) were found in WEE 71V-1658 (11234–11273 and 11292–11331). However, the 3' NTR of WEE showed some surprising results that had not been previously described. The first 40 nt terminal repeat formed the backbone for the formation of a 57 nt double stem loop structure (11228–11284) (FIG. 4b), consisting of an α and β loop. The second 40 nt repeat of WEE formed a nearly identical 59 nt double stem loop structure (11285–11343), directly adjacent to the first structure. SIN with three 40 nt repeats, forms three double stem loops (FIG. 4a) while EEE, which does not contain a SIN-like 40 nt repeat, contains the α and β loops (FIG. 4c).

Nonstructural Region

Comparisons within the nonstructural regions (4475 nt) of WEE strains 71V-1658 and 5614 (Weaver et al., 1993), yielded 94 nt changes resulting in 26 amino acid substitutions (1.8% difference) as summarized in Table 2. The most notable variation, a three-base deletion (4530) within the nsP3 gene of WEE 71V-1658 constitutes the only insertion/deletion observed within the polypeptide encoding regions. A short hypervariable region was observed (1421–1449), where 11 of 28 nt were different between the two WEE strains (FIG. 2b). The presence of an opal termination codon and partial read-through site at the junction of nsP3 and nsP4 is consistent with WEE 5614. Extending previous phylogenetic analyses of WEE (Weaver et al., 1993, 1997), phylogenetic trees depicting viral relatedness were constructed with the Distances program (GCG), for the unexamined genes (nsP1, nsP4) and the entire nonstructural polypeptide encoding region (FIG. 5). The data reveals the close relationship of WEE to EEE, relative to the other alphaviruses analyzed.

Structural Genes

The largest WEE cDNA clone isolated, pcDW-12, was 3100 bp in size, but missing 5 nt and the poly(A) tract from the 3' end as determined by restriction mapping and DNS sequence analysis. The missing 5' 1500 bp fragment was synthesized using PCR (primers WEE5'Sst1 and WEEP3) and subsequently cloned into pcDW-12 to yield a full-length clone of the structural genes (pcDWXH-7) (SEQ ID NO: 2). Comparison of the structural region of WEE 71V-1658 with WEE BFS 1703 (Hahn et al., 1988), indicated 53 nt changes, resulting in only 11 amino acid differences, of which two were nonconserved. One difference in residue was observed from the amino acid sequence of the N-terminus of the E2 protein of the WEE MacMillan strain (Bell et al., 1983), when this was compared to the deduced protein sequence of 71V-1658. A short fragment (802 nucleotides) of the WEE 71V-1658 E1 protein gene, and the 3' NTR had been published previously (Weaver et al., 1997); comparison with the sequence reported herein indicated no differences.

Expression of Structural Gene

Expression of the insert from the cytomegalovirus (CMV) promoter was accomplished by transfection of the pCXH-3 plasmid into either Vero or CHO K1 cells. Cells expressing the E1 or E2 proteins were detected through the use of specific E1 or E2 monoclonal antibodies to WEE, followed by histochemical staining with the HRP substrate, Tru-Blue as demonstrated in FIG. 6a. The control cells transfected with pCI alone showed no staining (FIG. 6b), thus, demonstrating the fidelity of the proteins translated from the cloned 26S region. In vitro translation of the insert using TNT T7 rabbit reticulysate and canine microsome system demonstrated synthesis of $^{35}$S-methionine-labelled proteins of the correct size as indicated by immunoprecipitation with monoclonal antibodies to the NC, E1 and E2 proteins (data not shown). Similarly, the construct pVHX-6 was along demonstrated to produce the correct MW proteins as determined by in vitro transcription/translation. The level of expression for pVHX-6 was significantly higher then for pCXH-3 (FIG. 7).

Protection Against WEE Infection Using DNA Immunization

Different strains of WEE were shown vary in their virulence in BALB/c mice. When similar amounts of WEE were given intranasally to BALB/c mice, time to death varied from 4 to 8 days. The California and Fleming strains were the most virulent (FIG. 8), and the Fleming strain was chosen as the challenge strain in protection studies. IP administration of the virus did not kill adult mice (data not shown). Intramuscular administration of pCXH-3 did not show any protection, using one or two doses of 50 µg, followed by challenge 30 to 90 days after the final dose (data not shown). Intramuscular administration did result in an increase in antibody titre to WEE as determined by ELISA using a monoclonal antibody to the E1 protein of WEE (data not shown). Expression and protection of pCXH-3 DNA when delivered ballistically. pCI was used as a control DNA. When two doses of pCXH-3 was given, protection of 50% was demonstrated as compared to no protection for pCI (FIG. 9) or PBS controls (data not shown). IM injection showed marginal protection (one group 25% survival-data not shown). The dose of WEE Fleming strain (challenge strain) was $1.25 \times 10^4$ PFU for 100% killing via an intranasal route of infection. Preliminary studies examining protection using the pVHX-6 vector, indicated promise with this construct using the Gene Gun, and ballistic delivery. With the pVHX-6 vector, one mouse succumbed immediately to the effects of the sodium pentabarbital (anaesthetic). The remaining three mice showed no signs of coming down with a WEE infection, and remained completely heathy (FIG. 10). Of the four pVAX control mice, all showed signs on WEE infection, and two of the four mice died, while two did recover. A repeat of this experiment using 3 or 4 doses of pVHX-6, given 2 weeks apart, showed complete protection of the mice, similar to 3 doses of WEE inactivated vaccine (FIG. 11). Three or 4 doses of pVAX showed results similar to the saline control, with only about 60% of the mice surviving FIG. 11.

Discussion

The WEE 71V-1658 genomic sequence of 11,508 bases was determined directly from cDNA clones of WEE or via sequencing RT-PCR products. The first 25 bases of the WEE genome was determined indirectly, through the use of a 5' RACE reaction in WEE CBA87. Noting the relatively high conservation in the WEE sequences overall (1.7% divergence) and in the overlap region between the two WEE sequences (see FIG. 2a), it appears that the 5' ends of 71V-1658 and CBA87 are of similar size and sequence.

Comparison of WEE 71V-1658 to other partial sequences of WEE (Hahn et al., 1988; Weaver et al., 1993) suggests little variation at the nucleotide level among these viruses (Table 2), showing an overall nt sequence difference of 1.7% over 8624 nt. Given a calculated rate of divergence of 0.028% per year for the WEE E1 protein (Weaver et al., 1997), the expected nt divergence for a difference in isolation of 18 years between the strains, should be 0.5% (71V-1658 isolated in 1971 and BFS 1703 in 1953). The E1 protein itself showed a rate of divergence of 1.5% in nt sequence between 71V-1658 and BFS1703. The lower rate observed by Weaver et al., (1997) could be due to greater conservation of structure at the C terminus of E1, from where the rates of divergence were calculated. Areas with high rates of divergence were observed between WEE strains 71V-1658 and 5614 at the 3' end of nsP1 and the 5'end of nsP4 (Table 2). The relatively high interstrain value for nsP1 (4.5% difference) may be due to the presence of a small hypervariable region, with 11 of 28 nt changed in strain 5614 (FIG. 2b). Variation in nsP4 occurred in a stretch of 21 nt at the 3' end of the 5614 sequence, and were left out of subsequent homology comparisons (similarity with the EEE sequence was maintained in this region). Discounting the carboxy-terminal region of nsP3 also gives a more accurate picture of the homology of the nsP1–4 nonstructural region (Weaver et al., 1993). The results for comparison of nt and protein sequences of WEE to other alphaviruses is shown in Table 2, and are similar to those obtained with nsP2 and nsP3 of 5614, when compared to other alphavirus sequences. Phylogenetic analysis of the WEE 71V-1658 deduced protein sequences of nsP1, nsP4 and the nsP1–4 region, as related to other alphaviruses (FIG. 5), illustrates the close relationship to EEE (HJ sequences were very limited for comparative purposes and were not included).

Assessments of codon usage frequencies and the frequency at which certain dinucleotides are found throughout the genome identified a number of statistical anomalies. The slight CpG dinucleotide deficiency previously described within other alphaviruses, and WEE itself, was confirmed in this study, at levels comparable to those reported (Weaver et al., 1993). The CpG under representation is a typical feature of vertebrate genomes, and is not seen in invertebrates. Viruses which infect dual hosts, such as the arboviruses, might be expected to utilize an intermediate nucleotide bias, as indicated by the slight CpG under-utilization observed in alphaviruses (Weaver et al., 1993). A pronounced under-representation of two other dinucleotides was also observed within the WEE genome, UpA, and CpC, a phenomenon noted throughout the genome, though the role of these codon preferences is unclear.

The 5' NTR sequence of WEE shows a close phylogenetic affiliation to EEE, and to HJ, although the HJ sequence information is more limited. Ou et al., (1983) had previously predicted (based on minimal free energy calculations) two hairpin structures at the 5' NTR of several alphaviruses including SIN and EEE. Both structures are present in WEE, the first of which is a 5' terminal hairpin structure (2-30), similar to that calculated for EEE (FIGS. 3a and b). The second is a dual hairpin structure (137-162, 165–189) which is almost identical to that identified for EEE. The region between the terminal and dual hairpins can itself form a long hairpin structure, and includes highly conserved stretches of 92 nt (data not shown). The significance of these structures is currently unknown.

Previous reports (Hahn et al., 1988; Pfeffer et al., 1998) suggested WEE virus arose as a result of two recombination events between alphavirus-like ancestral viruses. The first recombination occurred near the junction of the E3 and capsid genes. The second recombination occurred 80 nucleotides from the 3' end of the genome. Evidence for the occurrence of the second recombination event is inferred from sequence similarities of the 3' NTR between WEE, EEE and SIN, in which WEE shows greater similarity to EEE (65%) than to SIN (50%) in the last 100 nt of the 3' end. However, the apparent plasticity of the 3' NTR may only be reflecting the selective pressures under which the nascent WEE virus evolved, resulting in rapid selection of 3' sequences which are more similar to EEE, and may not represent an actual recombination event as previously postulated.

The 3' NTRs of alphaviruses are characterized by widespread sequence divergence and yet contain small, strongly conserved motifs (reviewed in Strauss & Strauss, 1994; Pfeffer et al., 1998). Analysis of the 3' NTR indicated the presence of double stem loop structures among SIN and WEE (FIGS. 4a and b). Interestingly, the 40 bp repeat found in SIN and WEE is contained within the double stem loop structure. SIN was found to contain 3 double stem loop structures and WEE was found to contain two. In SIN, the spacing between the three double stem loop structures was around 30 nucleotides, while in WEE the distance was zero nt separating the structures. Additional alphaviruses were assessed and it is interesting to note that double stem loop structures were found in many of the WEE- and SIN-related viruses (SIN, Aura, Babanki, Ockelbo, Kyzylagach, Whataroa, WEE and HJ). The double stem loop structures found in SIN and WEE viruses consisted of the α loop (AUGUA[U/C]UU) and the β loop (GCAUAAU) (FIG. 4b). Surprisingly, while EEE does not have the 40 bp repeat element found in SIN and WEE, it contains the α and β loop structures (FIG. 4c). The significance of these conserved loop structures between SIN, WEE and EEE viruses has yet to be elucidated, although previous studies suggest a role in viral replication and/or host specificity (Kuhn et al., 1990; Kuhn et al., 1991). For example a deletion of 26-318 nt from 3' end of SIN, resulted in reduced viral replication in mosquito cells but not in chicken cells (Kuhn et al., 1990). In contrast, substitution of the SIN 3' NTR with the substantially different RR 3' NTR (which lacks the 40 bp repeat and double stem loop structures), had no effect on the growth of the chimeric virus in mosquito cells, suggesting that host proteins interact with the 3' NTRs to cause differential host effects (Kuhn et al., 1991).

The 26S region of 71V-1658 was placed under the control of the CMV promoter of pCI. To test for functional expression of the pCXH-3 vector and for a functional product in cell culture, the pCXH-3 vector was transiently transfected into Vero cells. WEE proteins were detected on the cell using specific monoclonal antibodies to both the E1 (FIG. 6a) and E2 proteins (data not shown). The binding specificity of these monoclonals has been previously determined by western blot analysis and immunoprecipitation analysis (data not shown). The use of pCXH-3 in DNA immunization experiments indicated that the construct could partially protect against WEE intranasal challenge using ballistic delivery. Preliminary results do indicate that WEE reactive antibodies can be detected by ELISA when the pCXH-3 plasmid is given intramuscularly (unpublished results). However, this afforded no protection to the mice, as there were no survivors. Intranasal (data not shown) delivery of the pCXH-3, with and without liposome encapsulation did not demonstrate any protection under the conditions used. Mice immunized with the pCI control plasmid did not show any signs of protection in these studies.

Expression of the WEE structural proteins in the pCI-based vector (pCHX-3) gave moderate to poor levels of expression in vitro, using the TNT expression kit. A new vector, pVAX (Invitrogen) was designed for DNA immunization and was basically the same as pCI, but lacked the intron found in the pCI vector. Initial restriction mapping of pCXH-3 indicated the plasmid was the expected size, but later analysis indicated a extra 4 kb fragment was present (data not shown). The WEE structural proteins were cloned and expressed in pVHX-6, indicating the correct sized proteins by SDS-PAGE, and producing higher levels of WEE product in vitro (FIG. 7). Preliminary results with pVHX-6 indicated it could completely protect mice against an intranasal challenge of WEE. While 50% of the pVAX mice did survive, they all demonstrated at least moderate to severe infection with WEE. It is possible that pVAX contains CpG motifs that show some protective effect, through a nonspecific adjuvant like effect (Kreig et al, 1998). However, there was a dramatic difference between the pVAX and the pVHX-6 group, in the protection afforded the two groups of mice.

The plasmids, pCXH-3 and pVHX-6 show promise as vaccine candidates for WEE. This is especially important for protection against an aerosol challenge of WEE, and event that would be envisioned in a potential biological warfare attack using WEE as a biological warfare agent. This agent is difficult to protect against if delivered aerosolly, as the agent is purported to travel up the nerves directly into the brain. The research is applicable to VEE and EEE, as these viruses can also cause encephalitis following a similar route of infection (equines and potentially human).

It is to be understood that the embodiments and variations shown and described herein are merely illustrative of the principles of this invention and that various modifications may be implemented by those skilled in the art without departing from the scope and spirit of the invention.

TABLE 1

WEE 26S Region Primers

| Name | Length | Sequence |
|---|---|---|
| WEEPRO | 30 | AATCACCCTCTACGGCTGACCTAAATAGGT |
| WEEPR-SST | 24 | GGCTGAGCTCAATAGGTGACGTAG |
| WEE3' | 30 | GTAGTGTATATTAGAGACCCATAGTGAGTC |
| WEE5'SST | 20 | TCCAGATACGAGCTCATACT |
| WEEN1 | 20 | GGTGCCGCTGGAGGCCGTTT |
| WEEN1A | 20 | GATCTTAGGAGGTCGATAGC |
| WEEN2 | 20 | GGCTGATGAAACCACTCCAC |
| WEEN3 | 20 | CCACCCGTGTGCTATTCACT |
| WEEN3A | 20 | CGCCGTGTTTCAGCCCAATA |
| WEEN4 | 20 | TCACGAGCGGAGCATCTGAG |
| WEEN5 | 20 | GGCATCACCCTCCACCTGAC |
| WEEN6 | 20 | TTGTTATTCTGTTCCGCTGC |
| WEEN7 | 20 | CTATTGATCATGCAGTCGCA |
| WEEN8 | 20 | AGTGGAGCCTCTGCGAGCGT |
| WEEN9 | 20 | GAGGAGTGGGCGGGAAAGGC |
| WEEN10 | 20 | CTAAAACTCGATGTATTTCC |
| WEEN11 | 20 | ACGCGAACGAAGATGAACGG |
| WEEN12 | 20 | ACTGTCATTGTGCTGTGTGG |
| WEEN13 | 20 | CACAGTCATTCCTTCACCAC |
| WEEN14 | 20 | CGTCATCAGAAAGGGGCTTG |
| WEEN15 | 20 | CAAAGCTGACAGGGAGGGAC |
| WEEN16 | 20 | GGAAAGCTGGTAAAGTGCCA |

TABLE 1-continued

WEE 26S Region Primers

| Name | Length | Sequence |
|---|---|---|
| WEEN0 | 20 | GGAGAACCACATAAAGTCGA |
| WNSP1 | 25 | GGCTAACGTGGACAGGGACGTGATG |
| WEEP0 | 20 | GGCTATCGACCTCCTAAGAT |
| WEEP0A | 20 | CTGTCGGTTCCCTGGTTTAG |
| WEEP1 | 20 | CTGGGGAACGTCGCCATACT |
| WEEP2 | 20 | CGTTCTCCAGCAGCGTGTCG |
| WEEP2A | 20 | TATTGGGCTGAAACACGGCG |
| WEEP3 | 20 | CTTCAAGTGATCGTAAACGT |
| WEEP4 | 20 | ACTCCAGCCCTTCTCGCCCC |
| WEEP5 | 20 | GTTCGACCAACGCCTTATAC |
| WEEP6 | 20 | AAGGGTGAAAAAGCGGCTGA |
| WEEP7 | 20 | GGTGATTCTGATGATCTCAC |
| WEEP8 | 20 | TGGAAACTGCCGCCTGGAAT |
| WEEP10 | 20 | CCTTGATGTCATGGTCGTGG |
| WEEP11 | 20 | TGCACTGAGTGGTCTGTGTG |
| WEEP12 | 20 | ATGTTTCAGCGTTGGTTGGC |
| WEEP13 | 20 | GTGTTCTCACTGTCACAGAA |
| WEEP14 | 20 | ATGTGTGGTCGCTTCCTTCA |

The nucleotide sequences disclosed in Table 1 from-top to bottom are represented in the Sequence Listing as SEQ ID NOs. 10–49, respectively.

TABLE 2

Percentage Variation in Nucleotide and Encoded Amino Acid Sequences Between WEE 71V-1658 and Other Alphaviruses

| | WEE (BFS1703) | WEE (5614) | EEE | VEE | SIN | RR | ONN | SF |
|---|---|---|---|---|---|---|---|---|
| 5'NTR | — | — | | | | | | |
| nsP1 (nt) | — | (4.5) | 25.1 | 34.8 | 40.9 | 37.8 | 39.7 | 39.1 |
| nsP1 (aa) | — | (6.3) | 15.1 | 32.1 | 40.3 | 35.5 | 37.2 | 33.3 |
| nsP2 (nt) | — | 1.8 | 28.2 | 34.6 | 43.9 | 42.1 | 42.9 | 42.8 |
| nsP2 (aa) | — | 0.6 | 16.2 | 26.5 | 44.9 | 43.2 | 44.9 | 44.4 |
| nsP3 (nt)* | — | 1.8 | 30.2 | 36.7 | 45.8 | 39.3 | 42.6 | 42.2 |
| nsP3 (aa)* | — | 2.1 | 18.8 | 32.4 | 46.3 | 38.7 | 40.9 | 43.5 |
| nsP4 (nt) | (1.8) | (2.4) | 25.6 | 31.4 | 34.7 | 35.3 | 36.0 | 37.0 |
| nsP4 (aa) | (2.6) | (4.3) | 11.7 | 21.4 | 26.8 | 27.3 | 25.8 | 27.4 |
| intervening (nt) | 4.3 | — | 56.6 | 51.5 | 47.6 | 44.7 | 60.0 | 47.7 |
| Capsid (nt) | 2.1 | — | 26.3 | 40.8 | 47.7 | 46.3 | 47.5 | 48.2 |
| Capsid (aa) | 1.5 | — | 16.8 | 43.5 | 52.8 | 53.3 | 54.6 | 54.3 |
| E3 (nt) | 1.1 | — | 45.6 | 40.7 | 38.3 | 51.7 | 7.5 | 46.7 |
| E3 (aa) | 1.7 | — | 38.0 | 39.6 | 39.4 | 46.0 | 45.8 | 43.9 |
| E2 (nt) | 1.2 | — | 51.2 | 52.3 | 36.2 | 51.7 | 55.3 | 52.8 |
| E2 (aa) | 1.0 | — | 59.0 | 60.0 | 31.7 | 63.5 | 65.7 | 64.7 |
| 6K (nt) | 0.6 | — | 53.3 | 46.3 | 26.1 | 51.9 | 50.3 | 54.3 |
| 6K (aa) | 1.8 | — | 65.6 | 59.3 | 32.7 | 72.2 | 69.1 | 75.9 |

TABLE 2-continued

Percentage Variation in Nucleotide and Encoded Amino
Acid Sequences Between WEE 71V-1658 and Other Alphaviruses

|          | WEE (BFS1703) | WEE (5614) | EEE  | VEE  | SIN  | RR   | ONN  | SF   |
|----------|---------------|------------|------|------|------|------|------|------|
| E1 (nt)  | 1.5           | —          | 43.8 | 45.8 | 29.6 | 47.2 | 48.5 | 44.4 |
| E1 (aa)  | 0.5           | —          | 49.0 | 51.0 | 23.4 | 51.5 | 54.8 | 50.3 |
| 3'NTR (nt)| 0.7          | —          | 57.8 | 55.0 | 53.2 | 69.1 | 65.8 | 60.3 |

*based on N terminal domain, C terminal domain discarded due to lack of homology between alphaviruses
( ) based on incomplete sequence data: nsP1 (289 nt) and nsP4 (207 nt for BFS1703, 113 nt for 5614)
— no data

What is claimed is:

1. A western equine encephalitis ("WEE") virus strain comprising the nucleotide sequence shown in SEQ ID NO: 1.

* * * * *